US012649722B2

(12) United States Patent
Dale et al.

(10) Patent No.: US 12,649,722 B2
(45) Date of Patent: Jun. 9, 2026

(54) HERBICIDAL CINNOLINE DERIVATIVES

(71) Applicant: SYNGENTA CROP PROTECTION AG, Basel (CH)

(72) Inventors: Suzanna Jane Dale, Bracknell (GB); Zoe Jane Anderson, Bracknell (GB); Louisa Whalley, Bracknell (GB); Gordon Richard Munns, Bracknell (GB); James Alan Morris, Bracknell (GB); Paul Matthew Burton, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 479 days.

(21) Appl. No.: 17/999,249

(22) PCT Filed: May 14, 2021

(86) PCT No.: PCT/EP2021/062884

§ 371 (c)(1),
(2) Date: Nov. 18, 2022

(87) PCT Pub. No.: WO2021/233786

PCT Pub. Date: Nov. 25, 2021

(65) Prior Publication Data

US 2023/0303498 A1 Sep. 28, 2023

(30) Foreign Application Priority Data

May 19, 2020 (GB) ..................................... 2007419

(51) Int. Cl.

| | |
|---|---|
| ***C07D 237/28*** | (2006.01) |
| ***A01N 25/32*** | (2006.01) |
| ***A01N 43/58*** | (2006.01) |
| ***A01N 43/647*** | (2006.01) |
| ***A01N 43/76*** | (2006.01) |
| ***A01N 43/80*** | (2006.01) |
| ***A01N 43/84*** | (2006.01) |
| ***A01P 13/00*** | (2006.01) |
| ***C07D 403/04*** | (2006.01) |
| ***C07D 405/04*** | (2006.01) |
| ***C07D 413/04*** | (2006.01) |

(52) U.S. Cl.

CPC ........... *C07D 237/28* (2013.01); *A01N 25/32* (2013.01); *A01N 43/58* (2013.01); *A01N 43/647* (2013.01); *A01N 43/76* (2013.01); *A01N 43/80* (2013.01); *A01N 43/84* (2013.01); *A01P 13/00* (2021.08); *C07D 403/04* (2013.01); *C07D 405/04* (2013.01); *C07D 413/04* (2013.01)

(58) Field of Classification Search

None

See application file for complete search history.

(56) References Cited

U.S. PATENT DOCUMENTS

| | | | | |
|---|---|---|---|---|
| 4,729,782 A | | 3/1988 | Labovitz et al. | |
| 4,756,740 A | * | 7/1988 | Labovitz .............. | C07D 495/04 504/238 |
| 4,915,727 A | * | 4/1990 | Mizutani ................ | A01H 1/026 562/439 |
| 5,129,939 A | | 7/1992 | Labovitz et al. | |
| 5,183,891 A | | 2/1993 | Labovitz et al. | |
| 5,696,055 A | | 12/1997 | Labovitz et al. | |

FOREIGN PATENT DOCUMENTS

| | | |
|---|---|---|
| CN | 1041087 A | 4/1990 |
| EP | 0138661 A2 | 4/1985 |
| EP | 0 197 226 A1 | 10/1986 |
| EP | 0273325 A2 | 7/1988 |
| EP | 0274717 A2 | 7/1988 |
| EP | 0320793 A2 | 6/1989 |
| EP | 1044688 A1 | 10/2000 |

OTHER PUBLICATIONS

Guilford, et al., “Synthesis and pollen suppressant activity of phenylcinnoline-3-carboxylic acids”, J. Agric. Food Chem., vol. 40, No. 10, pp. 2026-2032, 1992.

Prudchenko, et al., “Reactions of ethyl pentafluorobenzoylacetate”, Zhurnal Obshchei Khimii, vol. 37, No. 11, pp. 2487-2493, 1967, with partial English translation.

UKIPO; App. No. GB2007419.1; Search Report under Section 17 dated Oct. 27, 2020; p. 1.

WIPO; App. No. PCT/EP2021/062884; International Search Report and Written Opinion dated Jul. 26, 2021; pp. 1-9.

* cited by examiner

*Primary Examiner* — Erin E Hirt

(74) *Attorney, Agent, or Firm* — BakerHostetler; Toni-Junell Herbert

(57) ABSTRACT

Compounds of the Formula (I) wherein the substituents are as defined in claim 1. The invention further relates to herbicidal compositions which comprise a compound of Formula (I) and to the use of compounds of Formula (I) for controlling weeds, in particular in crops of useful plants.

(I)

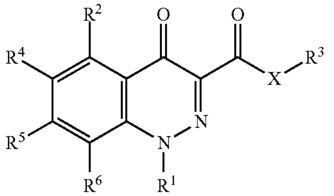

20 Claims, No Drawings

HERBICIDAL CINNOLINE DERIVATIVES

CROSS-REFERENCE TO RELATED APPLICATIONS

This application is a 371 National Stage Application of International Application No. PCT/EP2021/062884, filed May 14, 2021, which claims priority to GB 2007419.1, filed May 19, 2020, the entire contents of which are incorporated by reference herein.

The present invention relates to herbicidal cinnoline derivatives, e.g., as active ingredients, which have herbicidal activity. The invention also relates to agrochemical compositions which comprise at least one of the cinnoline derivatives, to processes of preparation of these compounds and to uses of the cinnoline derivatives or compositions in agriculture or horticulture for controlling weeds, in particular in crops of useful plants.

EP0273325, EP0274717, and US5183891 describe cinnoline derivatives as herbicidal agents.

According to the present invention, there is provided a compound of formula (I):

(I)

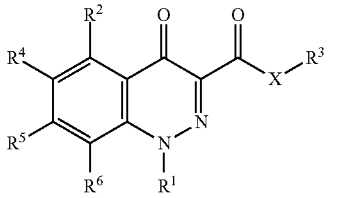

wherein

X is O, $NR^{13}$ or S;

$R^1$ is phenyl optionally substituted with 1, 2, 3, or 4 groups, which may be the same or different, represented by $R^7$;

$R^2$ is halogen, cyano, cyano$C_1$-$C_6$alkyl, $C_1$-$C_6$haloalkyl, $C_1$-$C_6$alkylcarbonyl, $C_2$-$C_6$alkenyl, $C_2$-$C_6$alkynyl, $C_1$-$C_6$alkoxy$C_2$-$C_6$alkenyl, $C_2$-$C_6$alkenyloxy$C_1$-$C_6$alkyl, $—CR^{11}═N—PR^{10}$, oxo-$C_1$-$C_6$alkyl, nitro, phenyl, phenoxy, heteroaryl, wherein the heteroaryl moiety is a 5- or 6-membered aromatic monocyclic ring comprising 1, 2, or 3 heteroatoms individually selected from N, O and S, heterocyclyl, or heterocyclyloxy, wherein the heterocyclyl moieties are a 4-, 5- or 6-membered non-aromatic monocyclic ring comprising 1 or 2 heteroatoms individually selected from N, O and S and wherein the phenyl, phenoxy, heteroaryl, heterocyclyl, and heterocyclyloxy moieties may each be optionally substituted with 1, 2 or 3 groups, which may be the same or different, represented by $R^8$, and wherein the heteroaryl and heterocyclyl moieties may be linked to the rest of the molecule through a carbon or nitrogen atom;

$R^3$ is hydrogen, $C_1$-$C_6$alkyl, $C_1$-$C_3$haloalkyl, $C_3$-$C_6$cycloalkyl, $C_3$-$C_6$cycloalkyl$C_1$-$C_6$alkyl, $C_1$-$C_6$alkoxy$C_1$-$C_6$alkyl, $C_2$-$C_6$alkenyl, $C_2$-$C_6$alkynyl, phenyl, or phenyl$C_1$-$C_3$alkyl, wherein the phenyl moieties may be optionally substituted with 1, 2, 3 or 4 groups, which may be the same or different, represented by $R^{12}$;

$R^4$, $R^5$, and $R^6$ are each independently selected from hydrogen, halogen, cyano, $C_1$-$C_6$alkyl, $C_1$-$C_6$alkoxy, $C_1$-$C_6$haloalkyl, $C_1$-$C_6$haloalkoxy, $C_1$-$C_6$alkylsulfanyl, $C_1$-$C_6$alkylsulfinyl, and $C_1$-$C_6$alkylsulfonyl;

$R^7$ is halogen, cyano, $C_1$-$C_6$alkyl, $C_1$-$C_6$alkoxy, $C_1$-$C_6$haloalkyl, $C_1$-$C_6$haloalkoxy, $C_1$-$C_6$alkylsulfanyl, or $C_1$-$C_6$alkylsulfonyl; or any two adjacent $R^7$ groups together with the carbon atoms to which they are attached, may form a 5- or 6-membered heterocyclyl ring, comprising 1 or 2 heteroatoms selected from O and N, or any two adjacent $R^7$ groups together with the carbon atoms to which they are attached, may form a 5- or 6-membered heteroaryl ring, comprising 1 or 2 heteroatoms selected from O and N, and wherein the heterocyclyl or heteroaryl rings may be optionally substituted with 1, 2, 3 or 4 groups, which may be the same or different, represented by $R^9$;

$R^8$ and $R^9$ are each independently selected from halogen, $C_1$-$C_3$alkyl, $C_1$-$C_3$haloalkyl, and $C_1$-$C_3$alkoxy;

$R^{10}$ and $R^{11}$ are each independently selected from hydrogen and $C_1$-$C_3$alkyl;

$R^{12}$ is halogen, cyano, $C_1$-$C_3$alkyl, or $C_1$-$C_3$alkoxy; $R^{13}$ is hydrogen, $C_1$-$C_3$alkyl, or $C_1$-$C_3$alkoxy;

or a salt or an N-oxide thereof.

Surprisingly, it has been found that the novel compounds of Formula (I) have, for practical purposes, a very advantageous level of herbicidal activity.

According to a second aspect of the invention, there is provided an agrochemical composition comprising a herbicidally effective amount of a compound of Formula (I) according to the present invention. Such an agricultural composition may further comprise at least one additional active ingredient and/or an agrochemically-acceptable diluent or carrier.

According to a third aspect of the invention, there is provided a method of controlling weeds at a locus comprising applying to the locus a weed controlling amount of a composition comprising a compound of Formula (I).

According to a fourth aspect of the invention, there is provided the use of a compound of Formula (I) as a herbicide.

Where substituents are indicated as being "optionally substituted", this means that they may or may not carry one or more identical or different substituents, e.g., one, two or three $R^8$ substituents. For example, $C_1$-$C_6$alkyl substituted by 1, 2 or 3 halogens, may include, but not be limited to, $—CH_2Cl$, $—CHCl_2$, $—CCl_3$, $—CH_2F$, $—CHF_2$, $—CF_3$, $—CH_2CF_3$ or $—CF_2CH_3$ groups. As another example, $C_1$-$C_6$alkoxy substituted by 1, 2 or 3 halogens, may include, but not limited to, $CH_2ClO—$, $CHCl_2O—$, $CCl_3O—$, $CH_2FO—$, $CHF_2O—$, $CF_3O—$, $CF_3CH_2O—$ or $CH_3CF_2O—$ groups.

As used herein, the term "cyano" means a —CN group.

As used herein, the term "halogen" refers to fluorine (fluoro), chlorine (chloro), bromine (bromo) or iodine (iodo).

As used herein, the term "hydroxy" means an —OH group.

As used herein, the term "acetyl" means a $—C(O)CH_3$ group.

As used herein, the term "nitro" means an $NO_2$ group.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. "$C_1$-$C_4$alkyl" and "$C_1$-$C_3$alkyl" are to be construed accordingly. Examples of $C_1$-$C_6$alkyl include, but are not limited to, methyl, ethyl, n-propyl, and the isomers thereof, for example, iso-propyl.

A "$C_1$-$C_6$alkylene" group refers to the corresponding definition of $C_1$-$C_3$alkyl, except that such radical is attached to the rest of the molecule by two single bonds. The term "$C_1$-$C_2$alkylene" is to be construed accordingly. Examples of $C_1$-$C_6$alkylene, include, but are not limited to, —$CH_2$—, —$CH_2CH_2$— and —$(CH_2)_3$—.

As used herein, the term "$C_1$-$C_6$haloalkyl" refers a $C_1$-$C_6$alkyl radical as generally defined above substituted by one or more of the same or different halogen atoms. The terms "$C_1$-$C_4$haloalkyl" and "$C_1$-$C_3$haloalkyl", are to be construed accordingly. Examples of $C_1$-$C_6$haloalkyl include, but are not limited to trifluoromethyl.

As used herein, the term "$C_1$-$C_6$di-haloalkyl" refers a $C_1$-$C_6$alkyl radical as generally defined above substituted by two of the same or different halogen atoms. The terms "$C_1$-$C_4$di-haloalkyl" and "$C_1$-$C_3$di-haloalkyl", are to be construed accordingly. Examples of $C_1$-$C_6$di-haloalkyl include, but are not limited to difluoromethyl.

As used herein, the term "cyano$C_1$-$C_6$alkyl" refers to a $C_1$-$C_6$alkyl radical as generally defined above substituted by one or more cyano groups, as defined above. Examples of cyano$C_1$-$C_3$alkyl include, but are not limited to 2-cyanomethyl and 2-cyanoethyl.

As used herein, the term "$C_1$-$C_3$haloalkoxy" refers to a $C_1$-$C_3$alkoxy radical as generally defined above substituted by one or more of the same or different halogen atoms. The terms "$C_1$-$C_4$haloalkoxy" and "$C_1$-$C_3$haloalkoxy", are to be construed accordingly. Examples of $C_1$-$C_6$haloalkoxy include, but are not limited to trifluoromethoxy.

As used herein, the term "$C_1$-$C_6$alkoxy" refers to a radical of the formula —$OR^a$ where $R^a$ is a $C_1$-$C_3$alkyl radical as generally defined above. The terms "$C_1$-$C_4$alkoxy" and "$C_1$-$C_3$alkoxy" are to be construed accordingly. Examples of $C_1$-$C_6$alkoxy include, but are not limited to, methoxy, ethoxy, 1-methylethoxy (iso-propoxy), and propoxy.

As used herein, the term "$C_2$-$C_6$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. The term "$C_2$-$C_3$alkenyl" is to be construed accordingly. Examples of $C_2$-$C_6$alkenyl include, but are not limited to, ethenyl (vinyl), prop-1-enyl, prop-2-enyl (allyl), but-1-enyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_3$alkynyl" is to be construed accordingly. Examples of $C_2$-$C_6$alkynyl include, but are not limited to, ethynyl, prop-1-ynyl, but-1-ynyl.

As used herein, the term "$C_1$-$C_6$alko$C_1$-$C_6$alkyl" refers to a radical of the formula $R^bOR^a$— wherein $R^b$ is a $C_1$-$C_6$alkyl radical as generally defined above, and $R^a$ is a $C_1$-$C_6$alkylene radical as generally defined above.

As used herein, the term "cyano$C_1$-$C_6$alkyl" refers to a $C_1$-$C_6$alkyl radical as generally defined above substituted by one or more cyano groups, as defined above. Examples of cyano$C_1$-$C_6$alkyl include, but are not limited to 2-cyanoethyl.

As used herein, the term "$C_2$-$C_6$cycloalkyl" refers to a radical which is a monocyclic saturated ring system and which contains 3 to 6 carbon atoms. The terms "$C_3$-$C_5$cycloalkyl" and "$C_3$-$C_4$cycloalkyl" are to be construed accordingly. Examples of $C_3$-$C_6$cycloalkyl include, but are not limited to, cyclopropyl, cyclobutyl, cyclopentyl and cyclohexyl.

As used herein, the term "$C_3$-$C_6$cycloalkyl$C_1$-$C_6$alkyl" refers to a $C_3$-$C_5$cycloalkyl ring attached to the rest of the molecule by a $C_1$-$C_6$alkylene linker as defined above.

As used herein, the term "$C_1$-$C_6$alkoxy$C_2$-$C_6$alkenyl" refers to a a radical of the formula $R^bOR^a$— wherein $R^b$ is a $C_1$-$C_6$alkyl radical as generally defined above, and $R^a$ is a $C_1$-$C_6$alkene radical as generally defined above. Examples of $C_1$-$C_6$alkoxy$C_2$-$C_6$alkenyl include, but are not limited to 1-methoxyvinyl and 1-ethoxyvinyl.

As used herein, the term "$C_2$-$C_6$alkenyloxy$C_1$-$C_6$alkyl" refers to a radical of the formula $R^bOR^a$— wherein $R^b$ is a $C_2$-$C_6$alkenyl radical as generally defined above, and $R^a$ is a $C_1$-$C_6$alkylene radical as generally defined above.

As used herein, the term "oxo-$C_1$-$C_6$alkyl" refers to a radical of the formula —$R^a$CHO, wherein $R^a$ is a $C_1$-$C_6$alkene radical as generally defined above. Examples of "oxo-$C_1$-$C_6$alkyl" include, but are not limited to 2-oxo-ethyl.

As used herein, the term "phenoxy" refers to a phenyl ring attached to the rest of the molecule through an oxygen atom.

As used herein, the term "phenyl$C_1$-$C_3$alkyl" refers to a phenyl ring attached to the rest of the molecule by a $C_1$-$C_3$alkylene linker as defined above.

As used herein, the term "heterocyclyl" refers to a stable 4-, 5- or 6-membered non-aromatic monocyclic ring which comprises 1 or 2 heteroatoms, wherein the heteroatoms are individually selected from nitrogen, oxygen, and sulfur. The heterocyclyl radical may be bonded to the rest of the molecule via a carbon atom or heteroatom. Examples of heterocyclyl include, but are not limited to, azetidinyl, oxetanyl, thietanyl, tetrahydrofuranyl, pyrrolidinyl, pyrazolidinyl, imidazolidnyl, piperidinyl, piperazinyl, morpholinyl, dioxolanyl, dithiolanyl and thiazolidinyl.

As used herein, the term "heterocyclyloxy" refers to a heterocyclyl ring attached to the rest of the molecule through an oxygen atom.

As used herein, the term "heteroaryl" refers to a 5- or 6-membered aromatic monocyclic ring radical which comprises 1, 2, 3 or 4 heteroatoms individually selected from nitrogen, oxygen, and sulfur. Examples of heteroaryl include, but are not limited to, furanyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "$C_1$-$C_6$alkylcarbonyl" refers to a radical of the formula —C(O)$R^a$, where $R^a$ is a $C_1$-$C_6$alkyl radical as generally defined above.

As used herein, the term "$C_1$-$C_6$alkylsulfanyl" refers to a radical of the formula —$SR_a$, where $R^a$ is a $C_1$-$C_6$alkyl radical as generally defined above. The terms "$C_1$-$C_4$alkylsulfonyl" and "$C_1$-$C_3$alkylsulfanyl", are to be construed accordingly. Examples of $C_1$-$C_6$alkylsulfanyl include, but are not limited to methylsulfanyl.

As used herein, the term "$C_1$-$C_6$alkylsulfinyl" refers to a radical of the formula —S(O)$R^a$, where $R^a$ is a $C_1$-$C_6$alkyl radical as generally defined above. The terms "$C_1$-$C_4$alkylsulfinyl" and "$C_1$-$C_3$alkylsulfinyl", are to be construed accordingly. Examples of $C_1$-$C_6$alkylsulfinyl include, but are not limited to methylsulfinyl.

As used herein, the term "$C_1$-$C_6$alkylsulfonyl" refers to a radical of the formula —$S(O)_2R^a$, where $R^a$ is a $C_1$-$C_6$alkyl radical as generally defined above. The terms "$C_1$-$C_4$alkylsulfonyl" and "$C_1$-$C_3$alkylsulfonyl", are to be construed accordingly. Examples of $C_1$-$C_6$alkylsulfanyl include, but are not limited to methylsulfonyl.

The presence of one or more possible stereogenic elements in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof fora compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form. Salts that the compounds of Formula (I) may form with amines, including primary, secondary and tertiary amines (for example ammonia, dimethylamine and triethylamine), alkali metal and alkaline earth metal bases, transition metals or quaternary ammonium bases are preferred.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents X, $R^1$, $R^2$, $R^3$, $R^4$, $R^5$, $R^6$, $R^7$, $R^8$, $R^9$, $R^{10}$, $R^{11}$, $R^{12}$, and $R^{13}$, with reference to compounds of formula (D. For any one of these substituents, any of the definitions given below may be combined with any definition of any other substituent given below or elsewhere in this document.

X is O, N or S. In one set of embodiments, X is O. In another set of embodiments, X is S, in a further set of embodiments, X is N.

$R^1$ is phenyl optionally substituted with 1, 2, 3, or 4 groups, which may be the same or different, represented by $R^7$. Preferably, $R^1$ is phenyl optionally substituted with 1, 2, or 3 groups, which may be the same or different, represented by $R^7$. More preferably, $R^1$ is phenyl optionally substituted with 1 or 2 groups, which may be the same or different, represented by $R^7$. More preferably still, $R^1$ is phenyl optionally substituted with a single group represented by $R^7$. Even more preferably, $R^1$ is phenyl substituted in the para position by a single group represented by $R^7$.

In one set of embodiments, $R^1$ is 4-(trifluoromethoxy)phenyl, 4-chlorophenyl, 3,4-dimethoxyphenyl, 4-methylsulfanylphenyl, 3-chloro-5-methyl-phenyl, 4-(trifluoromethyl)phenyl, 4-cyanophenyl, 7-quinolyl, 2,2-difluoro-1,3-benzodioxol-5-yl, 1-methylindazol-6-yl, 2,2,3,3-tetrafluoro-1,4-benzodioxin-6-yl, 3-chloro-4-methyl-phenyl, 3,4-dichlorophenyl, 3-cyanophenyl, 3-chlorophenyl, or 3-chloro-4-fluoro-phenyl.

In another set of embodiments, $R^1$ is 4-(trifluoromethoxy)phenyl, 4-chlorophenyl, or 3,4-dimethoxyphenyl. In a further set of embodiments, $R^1$ is 4-(trifluoromethoxy)phenyl, or 4-chlorophenyl.

$R^2$ is halogen, cyano, cyano$C_1$-$C_4$alkyl, $C_1$-$C_4$haloalkyl, $C_1$-$C_4$alkylcarbonyl, $C_2$-$C_6$alkenyl, $C_2$-$C_4$alkynyl, $C_1$-$C_4$alkoxy$C_2$-$C_4$alkenyl, $C_2$-$C_4$alkenyloxy$C_1$-$C_3$alkyl, —CR$^{11}$═—OR$^{10}$, oxo-$C_1$-$C_4$alkyl, nitro, phenyl, phenoxy, heteroaryl, wherein the heteroaryl moiety is a 5- or 6-membered aromatic monocyclic ring comprising 1, 2, or 3 heteroatoms individually selected from N and O, heterocyclyl, or heterocyclyloxy, wherein the heterocyclyl moieties are a 4-, 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1, 2 or 3 groups, which may be the same or different, represented by $R^8$.

Preferably, $R^2$ is halogen, cyano, cyano$C_1$-$C_3$alkyl, $C_1$-$C_3$haloalkyl, $C_1$-$C_3$alkylcarbonyl, $C_2$-$C_4$alkenyl, $C_2$-$C_4$alkynyl, $C_1$-$C_3$alkoxy$C_2$-$C_3$alkenyl, $C_2$-$C_3$alkenyloxy$C_1$-$C_3$alkyl, —CR$^{11}$═—OR$^{10}$, oxo-$C_1$-$C_3$alkyl, nitro, phenyl, phenoxy, heteroaryl, wherein the heteroaryl moiety is a 5- or 6-membered aromatic monocyclic ring comprising 1, 2, or 3 heteroatoms individually selected from N and O, heterocyclyl, or heterocyclyloxy, wherein the heterocyclyl moieties are a 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1, 2 or 3 groups, which may be the same or different, represented by $R^8$.

More preferably, $R^2$ is halogen, cyano, cyano$C_1$-$C_3$alkyl, $C_1$-$C_3$haloalkyl, $C_1$-$C_3$alkylcarbonyl, $C_2$-$C_4$alkenyl, $C_1$-$C_3$alkoxy$C_2$-$C_6$alkenyl, —CR$^{11}$═N—OR$^{10}$, oxo-$C_1$-$C_3$alkyl, nitro, phenyl, phenoxy, heteroaryl, wherein the heteroaryl moiety is a 5- or 6-membered aromatic monocyclic ring comprising 1, 2, or 3 heteroatoms individually selected from N and O, heterocyclyl, or heterocyclyloxy, wherein the heterocyclyl moieties are a 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1, 2 or 3 groups, which may be the same or different, represented by $R^8$.

Even more preferably, $R^2$ is halogen (preferably bromo), cyano, cyanomethyl, difluoromethyl, acetyl, vinyl, 1-methoxyvinyl, 1-ethoxyvinyl, —CR$^{11}$═—OR$^{10}$, 2-oxo-ethyl, nitro, phenyl, phenoxy, heteroaryl, wherein the heteroaryl moiety is a 5-membered aromatic monocyclic ring comprising 1, 2, or 3 heteroatoms individually selected from N and O, heterocyclyl, or heterocyclyloxy, wherein the heterocyclyl moieties are a 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1 or 2 groups, which may be the same or different, represented by $R^8$.

More preferably still, $R^2$ is cyano, cyanomethyl, difluoromethyl, acetyl, vinyl, 1-methoxyvinyl, 1-ethoxyvinyl, N-methoxy-C-methylcarbonimidoyl, N-hydroxy-C-methylcarbonimidoyl, 2-oxo-ethyl, nitro, phenyl, phenoxy, oxazolyl, isoxazolyl, pyrazolyl, triazolyl, pyrrolidinyl, piperidinyl, morpholino, and wherein the phenyl, phenoxy, oxazolyl, isoxazolyl, pyrazolyl, and triazolyl, moieties may each be optionally substituted with a single substituent represented by $R^8$.

In a further preferable embodiment, $R^2$ is cyano, cyanomethyl, difluoromethyl, acetyl, vinyl, 1-methoxyvinyl, 1-ethoxyvinyl, N-methoxy-C-methylcarbonimidoyl, N-hydroxy-C-methyl-carbonimidoyl, 2-oxo-ethyl, nitro, phenoxy, 5-oxazol-2-yl, isoxazol-3-yl, pyrazol-1-yl, triazol-1-yl, triazol-2-yl, 1-piperidinyl, morpholino, and wherein the phenoxy, isoxazolyl, pyrazolyl, and triazolyl, moieties may each be optionally substituted with a single substituent represented by R.

In another preferable embodiment, $R^2$ is cyano, cyanomethyl, difluoromethyl, acetyl, vinyl, 1-methoxyvinyl, 1-ethoxyvinyl, N-methoxy-C-methylcarbonimidoyl, N-hydroxy-C-methyl-carbonimidoyl, 2-oxo-ethyl, nitro, phenoxy, 5-oxazol-2-yl, 5-(difluoromethyl)isoxazol-3-yl, 4-chloropyrazol-1-yl, 4-(trifluoromethyl)triazol-1-yl, 4-(trifluoromethyl)triazol-2-yl, 1-piperidinyl, or morpholino.

$R^2$ is cyano, $C_1$-$C_6$alkylcarbonyl, $C_2$-$C_6$alkenyl, $C_2$-$C_6$alkynyl, $C_1$-$C_6$alkoxy$C_2$-$C_6$alkenyl, $C_2$-$C_6$ alkenyloxy$C_1$-$C_6$alkyl, —$CR^{11}$=—$OR^{10}$, phenyl, phenoxy, heteroaryl, wherein the heteroaryl moiety is a 5- or 6-membered aromatic monocyclic ring comprising 1, 2, or 3 heteroatoms individually selected from N, O and S, heterocyclyl, or heterocyclyloxy, wherein the heterocyclyl moieties are a 4-, 5- or 6-membered non-aromatic monocyclic ring comprising 1 or 2 heteroatoms individually selected from N, O and S, wherein the phenyl, phenoxy, heteroaryl, heterocyclyl, and heterocyclyloxy moieties may each be optionally substituted with 1, 2 or 3 groups, which may be the same or different, represented by $R^8$.

Preferably, $R^2$ is cyano, $C_1$-$C_6$alkylcarbonyl, $C_3$-$C_6$alkenyl, $C_3$-$C_6$alkynyl, $C_1$-$C_6$alkoxy$C_2$-$C_6$alkenyl, $C_3$-$C_6$alkenyloxy$C_1$-$C_4$alkyl, —$CR^{11}$=—$OR^{10}$, phenyl, phenoxy, heteroaryl, wherein the heteroaryl moiety is a 5- or 6-membered aromatic monocyclic ring comprising 1 or 2 heteroatoms individually selected from N, O and 5, heterocyclyl, or heterocyclyloxy, and wherein the heterocyclyl moieties are a 4-, 5- or 6-membered non-aromatic monocyclic ring comprising 1 or 2 heteroatoms individually selected from N, O and S, wherein the phenyl, phenoxy, heteroaryl, heterocyclyl, and heterocyclyloxy moieties may each be optionally substituted with 1, 2 or 3 groups, which may be the same or different, represented by $R^8$.

More preferably, $R^2$ is cyano, $C_1$-$C_4$alkylcarbonyl, $C_3$-$C_6$alkenyl, $C_3$-$C_6$alkynyl, $C_1$-$C_4$alkoxy$C_2$-$C_4$alkenyl, $C_3$-$C_4$alkenyloxy$C_1$-$C_3$alkyl, —$C_4$alkyl, —$CR^{11}$=—$OR^{10}$, phenyl, phenoxy, heteroaryl, wherein the heteroaryl moiety is a 5- or 6-membered aromatic monocyclic ring comprising 1 or 2 heteroatoms individually selected from N and O, heterocyclyl, or heterocyclyloxy, wherein the heterocyclyl moieties are a 5- or 6-membered non-aromatic monocyclic ring comprising 1 or 2 heteroatoms individually selected from N, O and 5, and wherein the phenyl, phenoxy, heteroaryl, heterocyclyl, and heterocyclyloxy moieties may each be optionally substituted with 1 or 2 groups, which may be the same or different, represented by $R^8$.

More preferably still, $R^2$ is cyano, $C_1$-$C_3$alkylcarbonyl, $C_1$-$C_3$alkoxy$C_2$-$C_3$alkenyl, —$C_4$alkyl, —$CR^{11}$=—$OR^{10}$, phenyl, phenoxy, heteroaryl, wherein the heteroaryl moiety is a 5-membered aromatic monocyclic ring comprising 1 or 2 heteroatoms individually selected from N and O, or heterocyclyl, wherein the heterocyclyl moiety is a 5- or 6-membered non-aromatic monocyclic ring comprising 1 or 2 heteroatoms individually selected from N and O, and wherein the phenyl, phenoxy, heteroaryl, and heterocyclyl moieties may each be optionally substituted with 1 or 2 groups, which may be the same or different, represented by $R^8$.

Even more preferably, $R^2$ is cyano, acetyl, propanoyl, 2-methylpropanoyl, 1-methoxyvinyl, 1-ethoxyvinyl, N-methoxy-C-methylcarbonimidoyl, N-ethoxy-C-methylcarbonimidoyl, phenyl, phenoxy, heteroaryl, wherein the heteroaryl moiety is a 5-membered aromatic monocyclic ring comprising 1 or 2 heteroatoms individually selected from N and O, or heterocyclyl, wherein the heterocyclyl moiety is a 5- or 6-membered non-aromatic monocyclic ring comprising 1 or 2 heteroatoms individually selected from N and O, and wherein the phenyl and phenoxy moieties may each be optionally substituted with a single group represented by $R^8$.

Even more preferably still, $R^2$ is cyano, acetyl, 1-methoxyvinyl, 1-ethoxyvinyl, N-methoxy-C-methylcarbonimidoyl, 4-fluorophenyl, 4-fluorophenoxy, or oxazol-2-yl.

In another preferred set of embodiments, $R^2$ is cyano$C_1$-$C_4$alkyl, $C_1$-$C_4$di-haloalkyl, $C_2$-$C_6$alkenyl, $C_2$-$C_4$alkynyl, $C_1$-$C_4$alkoxy$C_2$-$C_4$alkenyl, $C_2$-$C_4$alkenyloxy$C_1$-$C_3$alkyl, —$C_4$alkyl, —$CR^{11}$=—$OR^{10}$, oxo-$C_1$-$C_4$alkyl, nitro, phenyl, phenoxy, heteroaryl, wherein the heteroaryl moiety is a 5- or 6-membered aromatic monocyclic ring comprising 1, 2, or 3 heteroatoms individually selected from N and O, heterocyclyl, or heterocyclyloxy, wherein the heterocyclyl moieties are a 4-, 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1, 2 or 3 groups, which may be the same or different, represented by $R^8$.

In a further set of preferred embodiments, $R^2$ is cyano$C_1$-$C_3$alkyl, $C_1$-$C_3$di-haloalkyl, $C_2$-$C_3$alkenyl, $C_2$-$C_3$alkynyl, $C_1$-$C_3$alkoxy$C_2$-$C_4$alkenyl, $C_2$-$C_3$alkenyloxy$C_1$-$C_3$alkyl, —$CR^{11}$=—$OR^{10}$, oxo-$C_1$-$C_3$alkyl, nitro, phenyl, phenoxy, heteroaryl, wherein the heteroaryl moiety is a 5- or 6-membered aromatic monocyclic ring comprising 1, 2, or 3 heteroatoms individually selected from N and O, heterocyclyl, or heterocyclyloxy, wherein the heterocyclyl moieties are a 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1, 2 or 3 groups, which may be the same or different, represented by $R^8$.

In a still further set of preferred embodiments, $R^2$ is cyanomethyl, difluoromethyl, vinyl, 1-methoxyvinyl, 1-ethoxyvinyl, N-methoxy-C-methylcarbonimidoyl, N-hydroxy-C-methyl-carbonimidoyl, 2-oxo-ethyl, phenoxy, 5-oxazol-2-yl, 5-(difluoromethyl)isoxazol-3-yl, 4-chloropyrazol-1-yl, 4-(trifluoromethyl)triazol-1-yl, 4-(trifluoromethyl)triazol-2-yl, 1-piperidinyl, or morpholino.

$R^3$ is hydrogen, $C_1$-$C_6$alkyl, $C_1$-$C_6$haloalkyl, $C_1$-$C_6$cycloalkyl, $C_1$-$C_6$cycloalkyl$C_1$-$C_6$alkyl, $C_1$-$C_6$ alkoxy$C_1$-$C_6$alkyl, $C_2$-$C_6$alkenyl, $C_2$-$C_6$alkynyl, phenyl, or phenyl$C_1$-$C_3$alkyl, wherein the phenyl moieties may be optionally substituted with 1, 2, 3 or 4 groups, which may be the same or different, represented by $R^{12}$. Preferably, $R^3$ is hydrogen, $C_1$-$C_6$alkyl, $C_1$-$C_6$haloalkyl, $C_3$-$C_6$cycloalkyl, $C_3$-$C_5$cycloalkyl$C_1$-$C_3$alkyl, $C_1$-$C_4$alkoxy$C_1$-$C_3$alkyl, $C_2$-$C_6$alkenyl, $C_2$-$C_6$alkynyl, phenyl, or phenyl$C_1$-$C_2$alkyl, wherein the phenyl moieties may be optionally substituted with 1, 2, 3 or 4 groups, which may be the same or different, represented by $R^{12}$. More preferably, $R^3$ is hydrogen, $C_1$-$C_6$alkyl, $C_1$-$C_4$haloalkyl, $C_1$-$C_4$cycloalkyl, $C_3$-$C_6$ cycloalkyl$C_1$-$C_3$alkyl, $C_1$-$C_4$alkoxy$C_1$-$C_3$alkyl, $C_2$-$C_6$ alkenyl, $C_2$-$C_6$alkynyl, phenyl, or benzyl, wherein the phenyl moieties may be optionally substituted with 1, 2, or 3 groups, which may be the same or different, represented by $R^{12}$. More preferably still, $R^3$ is hydrogen, $C_1$-$C_6$alkyl, $C_1$-$C_4$haloalkyl, $C_3$-$C_6$cycloalkyl, $C_3$-$C_6$cycloalkyl$C_1$-$C_3$alkyl, $C_1$-$C_6$alkoxy$C_1$-$C_6$alkyl, phenyl, or benzyl, wherein the phenyl moieties may be optionally substituted with 1 or 2 groups, which may be the same or different, represented by $R^{12}$. In one set of embodiments, $R^3$ is hydrogen or $C_1$-$C_6$alkyl. Preferably, $R^3$ is hydrogen or $C_1$-$C_4$alkyl, more preferably, hydrogen or $C_1$-$C_3$alkyl. Even more preferably, $R^3$ is hydrogen, methyl, or ethyl. More preferably still, $R^3$ is hydrogen or methyl.

$R^4$ and $R^6$ are each independently selected from hydrogen, halogen, cyano, $C_1$-$C_6$alkyl, $C_1$-$C_6$alkoxy, $C_1$-$C_6$haloalkyl, $C_1$-$C_6$haloalkoxy, $C_1$-$C_6$alkylsulfanyl, $C_1$-$C_6$alkylsulfinyl, and $C_1$-$C_6$alkylsulfonyl, and $R^6$ is hydrogen.

Preferably, $R^4$ and $R^5$ are each independently selected from hydrogen, halogen, cyano, $C_1$-$C_4$alkyl, $C_1$-$C_4$alkoxy, $C_1$-$C_4$haloalkyl, $C_1$-$C_4$haloalkoxy, $C_1$-$C_6$alkylsulfanyl, $C_1$-$C_4$alkylsulfinyl, and $C_1$-$C_4$alkylsulfonyl, and $R^6$ is hydrogen.

More preferably, $R^4$ and $R^5$ are each independently selected from hydrogen, halogen, cyano, $C_1$-$C_4$alkyl, $C_1$-$C_3$alkoxy, $C_1$-$C_3$haloalkyl, $C_1$-$C_3$haloalkoxy, $C_1$-$C_3$alkylsulfanyl, $C_1$-$C_3$alkylsulfinyl, and $C_1$-$C_3$alkysulfonyl, and $R^6$ is hydrogen.

More preferably still, $R^4$ and $R^5$ are each independently selected from hydrogen, fluoro, bronco, cyano, $C_1$-$C_4$alkyl, methoxy, ethoxy, trifluoromethyl, trifluoromethoxy, methylsulfanyl, and methylsulfanyl, and $R^5$ is hydrogen.

Even more preferably, $R^4$ and $R^5$ are each independently selected from hydrogen, fluoro, bromo, cyano, methyl, isobutyl, methoxy, and trifluoromethyl, and $R^6$ is hydrogen.

In one embodiment, $R^4$, $R^5$, and $R^6$ are each independently selected from hydrogen, halogen; cyano, $C_1$-$C_6$alkyl, $C_1$-$C_6$alkoxy, $C_1$-$C_6$haloalkyl, $C_1$-$C_6$haloalkoxy, $C_1$-$C_6$alkylsulfanyl, $C_1$-$C_6$alkylsulfinyl, and $C_1$-$C_6$alkylsulfonyl. Preferably, $R^4$, $R^5$, and $R^6$ are each independently selected from hydrogen, halogen, cyano, $C_1$-$C_6$alkyl, $C_1$-$C_4$alkoxy, $C_1$-$C_4$haloalkyl, $C_1$-$C_4$haloalkoxy, $C_1$-$C_4$alkylsulfanyl, $C_1$-$C_4$alkylsulfinyl, and $C_1$-$C_4$alkylsulfonyl. More preferably, $R^4$, $R^5$, and $R^6$ are each independently selected from hydrogen, halogen, cyano, $C_1$-$C_4$alkyl, $C_1$-$C_3$alkoxy, $C_1$-$C_3$haloalkyl, $C_1$-$C_3$haloalkoxy, $C_1$-$C_3$alkylsulfanyl, $C_1$-$C_3$alkylsulfinyl, and $C_1$-$C_3$alkylsufonyl. More preferably still, $R^4$, $R^5$, and $R^6$ are each independently selected from hydrogen, fluoro, bromo; cyano, $C_1$-$C_4$alkyl, methoxy, ethoxy, trifluoromethyl, trifluoromethoxy, methylsulfanyl, and methylsulfanyl. Even more preferably, $R^4$; $R^5$; and $R^6$ are each independently selected from hydrogen, fluoro, bromo, cyano, methyl, isobutyl, methoxy, and trifluoromethyl.

In one set of embodiments, $R^4$ and $R^5$ are each independently selected from hydrogen, fluoro, bromo, cyano, methyl, isobutyl, methoxy, and trifluoromethyl, and $R^6$ is hydrogen. In a further set of embodiments, $R^4$, $R^5$, and $R^6$ are all hydrogen.

$R^7$ is halogen, cyano, $C_1$-$C_6$alkyl, $C_1$-$C_6$alkoxy, $C_1$-$C_6$haloalkyl, $C_1$-$C_6$haloalkoxy, $C_1$-$C_3$alkylsulfanyl, or $C_1$-$C_6$alkylsulfonyl; or any two adjacent $R^7$ groups together with the carbon atoms to which they are attached, may form a 5- or 6-membered heterocyclyl ring, comprising 1 or 2 heteroatoms selected from O and N, or any two adjacent $R^7$ groups together with the carbon atoms to which they are attached, may form a 5- or 6-membered heteroaryl ring, comprising 1 or 2 heteroatoms selected from O and N, and wherein the heterocyclyl or heteroaryl rings may be optionally substituted with 1, 2, 3 or 4 groups, which may be the same or different; represented by $R^9$.

Preferably, $R^7$ is halogen, cyano, $C_1$-$C_6$alkyl, $C_1$-$C_3$alkoxy, $C_1$-$C_3$haloalkyl, $C_1$-$C_3$haloalkoxy, $C_1$-$C_3$alkylsulfanyl, or $C_1$-$C_3$alkylsulfonyl; or any two adjacent $R^7$ groups together with the carbon atoms to which they are attached, may form a 5- or 6-membered heterocyclyl ring, comprising 1 or 2 heteroatoms selected from O and N, or any two adjacent $R^7$ groups together with the carbon atoms to which they are attached, may form a 5- or 6-membered heteroaryl ring, comprising 1 or 2 heteroatoms selected from O and N, and wherein the heterocyclyl or heteroaryl rings may be optionally substituted with 1, 2; 3 or 4 groups, which may be the same or different; represented by $R^9$.

More preferably, $R^7$ is halogen, cyano, $C_1$-$C_3$alkyl, $C_1$-$C_3$alkoxy, $C_1$-$C_3$haloalkyl, $C_1$-$C_3$haloalkoxy, or $C_1$-$C_3$alkylsulfanyl; or any two adjacent $R^7$ groups together with the carbon atoms to which they are attached, may form a 5- or 6-membered heterocyclyl ring, comprising 1 or 2 oxygen atoms, or any two adjacent $R^7$ groups together with the carbon atoms to which they are attached, may form a 5- or 6-membered heteroaryl ring, comprising 1 or 2 nitrogen atoms; and wherein the heterocyclyl or heteroaryl rings may be optionally substituted with 1, 2, 3 or 4 groups, which may be the same or different, represented by $R^9$.

Even more preferably, $R^7$ is chloro, cyano, methyl, methoxy, trifluoroalkyl, trifluoromethoxy, methylsulfanyl, or any two adjacent $R^7$ groups together with the carbon atoms to which they are attached form a quinolyl, indazolyl, 1,3-benzoxadiazolyl, or 1,4-benzodioxinyl group, and wherein the quinolyl, indazolyl, 1,3-benzoxadiazolyl, or 1,4-benzodioxinyl groups may be optionally substituted with 1 2, 3 or 4 groups, which may be the same or different, represented by $R^9$.

In one set of embodiments, $R^7$ is halogen, cyano, $C_1$-$C_6$alkyl, $C_1$-$C_6$alkoxy, $C_1$-$C_3$haloalkyl, $C_1$-$C_6$haloalkoxy, $C_1$-$C_6$alkylsulfanyl, or $C_1$-$C_3$alkylsulfonyl; or any two adjacent $R^7$ groups together with the carbon atoms to which they are attached, may form a 5- or 6-membered heterocyclyl ring, comprising 1 or 2 heteroatoms selected from O and N, and wherein the heterocyclyl ring may be optionally substituted with 1, 2, 3 or 4 groups, which may be the same or different, represented by $R^9$.

Preferably, $R^7$ is halogen, cyano, $C_1$-$C_3$alkyl, $C_1$-$C_3$alkoxy, $C_1$-$C_3$haloalkyl; $C_1$-$C_3$haloalkoxy, $C_1$-$C_3$alkylsulfinyl, $C_1$-$C_3$alkylsulfinyl, or $C_1$-$C_3$alkylsulfonyl; or any two adjacent $R^7$ groups together with the carbon atoms to which they are attached, may form a 5- or 6-membered heterocyclyl ring, comprising 1 or 2 heteroatoms selected from O and N, and wherein the heterocyclyl ring may be optionally substituted with 1, 2 or 3 groups, which may be the same or different, represented by $R^9$.

More preferably, $R^7$ is halogen, cyano, $C_1$-$C_3$alkyl, $C_1$-$C_3$alkoxy, $C_1$-$C_3$haloalkyl, $C_1$-$C_3$haloalkoxy, $C_1$-$C_3$alkylsulfanyl, $C_1$-$C_3$alkylsulfinyl, or $C_1$-$C_3$alkylsulfonyl.

Even more preferably, $R^7$ is fluoro, bromo, chloro, cyano, methyl, ethyl, isopropyl, methoxy, ethoxy, trifluoromethyl, trifluoromethoxy, methylsulfanyl, methylsulfinyl, or methylsulfonyl; or any two adjacent $R^7$ groups together with the carbon atoms to which they are attached; may form a 5- or 6-membered heterocyclyl ring; comprising 1 or 2 heteroatoms selected from O and N, and wherein the heterocyclyl ring may be optionally substituted with 1 or 2 groups, which may be the same or different, represented by $R^9$. Even more preferably, $R^7$ is fluoro, bromo, chloro, cyano, methyl, methoxy, trifluoromethyl, or trifluoromethoxy. More preferably still, $R^7$ is chloro, methoxy, or trifluoromethoxy. Even more preferably still, $R^7$ is chloro or trifluoromethoxy.

In a further set of embodiments, $R^7$ is $C_1$-$C_6$haloalkoxy. Preferably, $R^7$ is $C_1$-$C_4$haloalkoxy, more preferably, $R^7$ is $C_1$-$C_3$haloalkoxy. Even more preferably, $R^7$ is $C_1$-$C_3$fluoroalkoxy; and more preferably still, $R^7$ is trifluoromethoxy.

$R^8$ and $R^9$ are each independently selected from halogen, $C_1$-$C_3$alkyl, $C_1$-$C_3$haloalkyl, and $C_1$-$C_3$alkoxy.

Preferably, each $R^8$ is independently selected from halogen and $C_1$-$C_3$haloalkyl. More preferably, each $R^8$ is independently selected from halogen and $C_1$-$C_3$fluoroalkyl. Even more preferably, each $R^8$ is independently selected from fluoro, chloro, difluoromethyl, and trifluoromethyl.

Preferably, each $R^9$ is independently selected from halogen and $C_1$-$C_3$alkyl. More preferably, each $R^9$ is independently selected from halogen and methyl. Even more preferably, each $R^9$ is independently selected from fluoro and methyl.

In one set of embodiments, $R^8$ and $R^9$ are each independently selected from halogen, $C_1$-$C_3$alkyl, and $C_1$-$C_3$alkoxy. Preferably, $R^8$ and $R^9$ are each independently selected from halogen, methyl, ethyl, n-propyl, isopropyl, methoxy, ethoxy, or isopropoxy. More preferably, $R^8$ and $R^9$ are each independently selected from halogen, methyl, or methoxy. More preferably still, $R^8$ and $R^9$ are each independently selected from fluoro, chloro, methyl, or methoxy. In one set of embodiments, $R^8$ is fluoro.

$R^{10}$ and $R^{11}$ are each independently selected from hydrogen and $C_1$-$C_3$alkyl. Preferably, $R^{10}$ and $R^{11}$ are each independently selected from hydrogen, methyl and ethyl. In one set of embodiments, $R^{10}$ and $R^{11}$ are both methyl.

$R^{12}$ is halogen, cyano, $C_1$-$C_3$alkyl, or $C_1$-$C_3$alkoxy. Preferably, $R^{12}$ is bromo, chloro, fluoro, cyano, methyl or methoxy.

$R^{13}$ is hydrogen, $C_1$-$C_3$alkyl, or $C_1$-$C_3$alkoxy. Preferably, $R^{13}$ is hydrogen, methyl, or methoxy. More preferably, $R^{13}$ is hydrogen.

In a compound of formula (I) according to the present invention, preferably:

X is O, N or S;

$R^1$ is phenyl optionally substituted with 1 or 2 groups, which may be the same or different, represented by $R^7$;

$R^2$ is cyano, acetyl, propanoyl, 2-methylpropanoyl, 1-methoxyvinyl, 1-ethoxyvinyl, N-methoxy-C-methylcarbonimidoyl, N-ethoxy-C-methylcarbonimidoyl, phenyl, phenoxy, heteroaryl, wherein the heteroaryl moiety is a 5- or 6-membered aromatic monocyclic ring comprising 1 or 2 heteroatoms individually selected from N and O, or heterocyclyl, wherein the heterocyclyl moiety is a 5- or 6-membered non-aromatic monocyclic ring comprising 1 or 2 heteroatoms individually selected from N and O, and wherein the phenyl and phenoxy moieties may each be optionally substituted with a single group represented by $R^8$;

$R^3$ is hydrogen or $C_1$-$C_3$alkyl;

$R^4$, $R^5$, and $R^6$ are all hydrogen;

$R^7$ is halogen or $C_1$-$C_3$haloalkoxy; and $R^8$ is halogen.

In another set of embodiments, X is O;

$R^1$ is phenyl optionally substituted with a single group represented by $R^1$;

$R^2$ is cyano, $C_1$-$C_6$alkylcarbonyl, $C_2$-$C_6$alkenyl, $C_2$-$C_6$alkynyl, $C_1$-$C_6$alkoxy$C_2$-$C_6$alkenyl, $C_1$-$C_6$alkenyloxy$C_1$-$C_6$alkyl, —$CR^{11}$=—$OR^{10}$, phenyl, phenoxy, heteroaryl, wherein the heteroaryl moiety is a 5- or 6-membered aromatic monocyclic ring comprising 1, 2, or 3 heteroatoms individually selected from N, O and S, heterocyclyl, or heteracyclyloxy, wherein the heterocyclyl moieties are a 4-, 5- or 6-membered non-aromatic monocyclic ring comprising 1 or 2 heteroatoms individually selected from N, O and S, wherein the phenyl, phenoxy, heteroaryl, heterocyclyl, and heterocyclyloxy moieties may each be optionally substituted with 1, 2 or 3 groups, which may be the same or different, represented by $R^8$;

$R^3$ is hydrogen, methyl, or ethyl;

$R^4$, $R^5$, and $R^3$ are all hydrogen;

$R^7$ is halogen or $C_1$-$C_3$haloalkoxy; and $R^3$ is halogen.

In a further set of embodiments, X is O;

$R^1$ is phenyl optionally substituted with a single group represented by $R^7$;

$R^2$ is cyano, acetyl, 1-methoxyvinyl, 1-ethoxyvinyl, N-methoxy-C-methylcarbonimidoyl, 4-fluorophenyl, 4-fluorophenoxy, or oxazol-2-yl;

$R^3$ is hydrogen, methyl, or ethyl;

$R^4$, $R^5$, and $R^6$ are all hydrogen; and $R^7$ is halogen or $C_1$-$C_3$haloalkoxy.

In a further set of embodiments, X is O;

$R^1$ is phenyl optionally substituted with a single group represented by $R^7$;

$R^2$ is halogen, cyano, cyano$C_1$-$C_6$alkyl, $C_1$-$C_6$haloalkyl, $C_1$-$C_6$alkylcarbonyl, $C_2$-$C_6$alkenyl, $C_1$-$C_6$alkynyl, $C_1$-$C_6$alkoxy$C_2$-$C_6$alkenyl, $C_2$-$C_6$alkenyloxy$C_1$-$C_6$alkyl, —$CR^{11}$=—$OR^{10}$, oxo-$C_1$-$C_6$alkyl, nitro, phenyl, phenoxy, heteroaryl, wherein the heteroaryl moiety is a 5- or 6-membered aromatic monocyclic ring comprising 1, 2, or 3 heteroatoms individually selected from N, O and 8, heterocyclyl, or heterocyclyloxy, wherein the heterocyclyl moieties are a 4-, 5- or 6-membered non-aromatic monocyclic ring comprising 1 or 2 heteroatoms individually selected from N, O and S, and wherein the phenyl, phenoxy, heteroaryl, heterocyclyl, and heterocyclyloxy moieties may each be optionally substituted with 1, 2 or 3 groups, which may be the same or different, represented by R. and wherein the heteroaryl and heterocyclyl moieties may be linked to the rest of the molecule through a carbon or nitrogen atom;

$R^3$ is hydrogen, methyl, or ethyl;

$R^4$, $R^5$, and $R^6$ are all hydrogen;

$R^7$ is $C_1$-$C_3$haloalkoxy;

$R^8$ is fluoro, chloro, difluoromethyl, and trifluoromethyl.

$R^{16}$ is hydrogen or methyl; and $R^{11}$ is methyl.

In a still further set of embodiments, X is O;

$R^1$ is phenyl optionally substituted with a single group represented by $R^7$;

$R^2$ is cyano$C_1$-$C_4$alkyl, $C_1$-$C_4$alkenyl, $C_2$-$C_6$alkynyl, $C_1$-$C_4$alkoxy$C_2$-$C_4$alkenyl, $C_2$-$C_4$alkenyloxy$C_1$-$C_6$alkyl, —$CR^{11}$=—$OR^{10}$, oxo-$C_1$-$C_4$alkyl, nitro, phenyl, phenoxy, heteroaryl, wherein the heteroaryl moiety is a 5- or 6-membered aromatic monocyclic ring comprising 1, 2, or 3 heteroatoms individually selected from N and O, heterocyclyl, or heterocyclyloxy, wherein the heterocyclyl moieties are a 4-, 5- or 6-membered non-aromatic monocyclic ring comprising 1 or 2 heteroatoms individually selected from N and O, and wherein the phenyl, phenoxy, heteroaryl, heterocyclyl, and heterocyclyloxy moieties may each be optionally substituted with 1, 2 or 3 groups, which may be the same or different, represented by $R^8$, $R^3$ is hydrogen, methyl, or ethyl;

$R^4$, $R^5$, and $R^6$ are all hydrogen;

$R^7$ is chloro, methoxy, or trifluoromethoxy;

$R^8$ is fluoro, chloro, difluoromethyl, and trifluoromethyl.

$R^{10}$ is hydrogen or methyl; and $R^{11}$ is methyl.

In a particularly preferred embodiment, the compound of Formula (I) is selected from;

methyl 5-[(E)-N-methoxy-C-methyl-carbonimidoyl]-4-oxo-1-[4-(trifluoromethoxy)phenyl]cinnoline-3-carboxylate (P1), 5-[(E)-N-methoxy-C-methyl-carbonimidoyl]-4-oxo-1-[4-(trifluoromethoxy)phenyl]cinnoline-3-carboxylic acid (P2), methyl 5-(1-ethoxyvinyl)-4-oxo-1-[4-(trifluoromethoxy)phenyl]cinnoline-3-carboxylate (P3), methyl 5-(1-methoxyvinyl)-4-oxo-1-[4-(trifluoromethoxy)phenyl]cinnoline-3-carboxylate (P4), 5-oxazol-2-yl-4-oxo-1-[4-(trifluoromethoxy)phenyl]cinnoline-3-carboxylic acid (P5), methyl 5-(4-fluorophenyl)-4-oxo-1-[4-(trifluoromethoxy)phenyl]cinnoline-3-carboxylate (P6), methyl 5-cyano-4-oxo-[4-(trifluoromethoxy)phenyl]cinnoline-3-carboxylate (P7), 5-cyano-4-oxo-1-[4-(trifluoromethoxy)phenyl] cinnoline-3-carboxylic acid (P3), methyl 5-acetyl-4-oxo-1-[4-(trifluoromethoxy)phenyl]cinnoline-3-carboxylate (P9), 5-acetyl-4-oxo-1-[4-(trifluoromethoxy) phenyl]cinnoline-3-carboxylic acid (P10), 1-(4-chlorophenyl)- 5-(4-fluorophenoxy)-4-oxo-cinnoline-3-carboxylic acid (P11), ethyl 5-[5-(difluoromethyl) isoxazol-3-yl]-4-oxo-1-[4-(trifluoromethoxy)phenyl] cinnoline-3-carboxylate (P12), 5-[5-(difluoromethyl) isoxazol-3-yl]-4-oxo-1-[4-(trifluoromethoxy)phenyl] cinnoline-3-carboxylic acid (P13), ethyl 5-[(E)-N-hydroxy-C-methyl- carbonimidoyl]-4-oxo-1-[4-(trifluoromethoxy)phenyl]cinnoline-3-carboxylate (P14), 5-[(E)-N-hydroxy-C-methyl-carbonimidoyl]-4-oxo-1-[4-(trifluoromethoxy)phenyl]cinnoline-3- carboxylic acid (P15), ethyl 4-oxo-1-[4-(trifluoromethoxy)phenyl]-5-vinyl-cinnoline-3-carboxylate (P16), 4-oxo-1-[4-(trifluoromethoxy)phenyl]-5-vinyl-cinnoline-3-carboxylic acid (P17), ethyl 4-oxo-5-(2-oxoethyl)-[4-(trifluoromethoxy)phenyl]cinnoline-3-carboxylate (P17), 5-(4-chloropyrazol-1-oxo-4-oxo-1-[4-(trifluoromethoxy)phenyl]cinnoline-3-carboxylic acid (P19), 4-oxo-1-[4-(trifluoromethoxy)phenyl]-5-[4-(trifluoromethyl)triazol-2-yl]cinnoline-3-carboxylic acid (P20), 4-oxo-1-[4-(trifluoromethoxy)phenyl]-5-[4-(trifluoromethyl)triazol-1-yl]cinnoline-3-carboxylic acid (P21), 4-oxo-1-[4-(trifluoromethoxy)phenyl]-5-[4-(trifluoromethyl)pyrazol-1-yl]cinnoline-3-carboxylic acid (P22), 4-oxo-5-pyrrolidin-1-yl-1-[4-(trifluoromethoxy)phenyl]cinnoline-3-carboxylic acid (P23), 4-oxo-5-(1-piperidyl)-1-[4-(trifluoromethoxy)phenyl] cinnoline-3-carboxylic acid (P24), 5-morpholino-4-oxo-1-[4-(trifluoromethoxy)phenyl]cinnoline-3-carboxylic acid (P25), ethyl 5-morpholino-4-oxo-1-[4-(trifluoromethoxy)phenyl]cinnoline-3-carboxylate (P26), ethyl 4-oxo-5-(1-piperidyl)-1-[4-(trifluoromethoxy)phenyl]cinnoline-3-carboxylate (P27), ethyl 4-oxo-5-pyrrolidin-1-yl-1-[4-(trifluoromethoxy) phenyl]cinnoline-3-carboxylate (P26), ethyl 5-(1-ethoxyvinyl)-4-oxo-1-[4-(trifluoromethoxy)phenyl] cinnoline-3-carboxylate (P29), ethyl 5-acetyl-4-oxo-1-[4-(trifluoromethoxy)phenyl]cinnoline-3-carboxylate (P30), ethyl 4-oxo-1-[4-(trifluoromethoxy)phenyl]-5-[4-(trifluoromethyl)pyrazol-1-yl]cinnoline-3-carboxylate (P31), ethyl 5-(4-chloropyrazol-1-yl)-4-oxo-1-[4-(trifluoromethoxy)phenyl]cinnoline-3-carboxylate (P32), ethyl 4-oxo-1-[4-(trifluoromethoxy)phenyl]-5-[4-(trifluoromethyl)triazol-1-yl]cinnoline-3-carboxylate (P33), ethyl 4-oxo-1-[4-(trifluoromethoxy)phenyl]-5-[4-(trifluoromethyl)triazol-2-yl]cinnoline-3-carboxylate (P34), ethyl 5-(cyanomethyl)-4-oxo-1-[4-(trifluoromethoxy)phenyl]cinnoline-3-carboxylate (P35), ethyl 5-(difluoroethyl)-4-oxo-1-[4-(trifluoromethoxy)phenyl]cinnoline-3-carboxylate (P36), 5-(difluoromethyl)-4-oxo-1-[4-(trifluoromethoxy)phenyl]cinnoline-3- carboxylic acid (P37), ethyl 5-cyano-4-oxo-1-[4-(trifluoromethoxy)phenyl]cinnoline-3-carboxylate (P36), ethyl 5-nitro-4-oxo-1-[4-(trifluoromethoxy)phenyl]cinnoline-3-carboxylate (P39), 5-nitro-4-oxo-1-[4-(trifluoromethoxy)phenyl] cinnoline-3-carboxylic acid (P40), 5-cyano-1-(3,4-dimethoxyphenyl)-4-oxo-cinnoline-3-carboxylic acid (P41), and ethyl 5-cyano-1-(3,4-dimethoxyphenyl)-4-oxo-cinnoline-3-carboxylate (P42).

In another particularly preferred embodiment, the compound of Formula (I) is selected from:

methyl 5-RE)-N-methoxy-C-methyl-carbonimidoyl-4-oxo-1-[4-(trifluoromethoxy)phenyl]cinnoline-3-carboxylate (P1), 5-[(E)-N-methoxy-C-methyl-carbonimidoyl]-4-oxo-1-[4-(trifluoromethoxy)phenyl]cinnoline-3-carboxylic acid (P2), methyl 5-(1-ethoxyvinyl)-4-oxo-1-[4-(trifluoromethoxy)phenyl]cinnoline-3-carboxylate (P3), methyl 5-(1-methoxyvinyl)-4-oxo-1-[4-(trifluoromethoxy)phenyl]cinnoline-3-carboxylate (P4). 5-oxazol-2-yl-4-oxo-1-[4-(trifluoromethoxy)phenyl]cinnoline-3-carboxylic acid (P5), methyl 5-cyano-4- oxo-1-[4-(trifluoromethoxy)phenyl]cinnoline-3-carboxylate (P7), 5-cyano-4-oxo-1-[4-(trifluoromethoxy) phenyl]cinnoline-3-carboxylic acid (P8), methyl 5-acetyl-4-oxo-1-[4-(trifluoromethoxy)phenyl]cinnoline-3-carboxylate (P9), 5-acetyl-4-oxo-1-[4-(trifluoromethoxy)phenyl]cinnoline-3-carboxylic acid (P10), 1-(4-chlorophenyl)-5-(4-fluorophenoxy)-4-oxo-cinnoline-3-carboxylic acid (P11), ethyl 5-[5-(difluoromethyl)isoxazol-3-yl]-4-oxo-[4-(trifluoromethoxy)phenyl]cinnoline-3-carboxylate (P12), 5-[5-(difluoromethyl)isoxazol-3-yl]-4-oxo-1-[4-(trifluoromethoxy)phenyl]cinnoline-3-carboxylic acid (P13), ethyl 5-[(E)-N-hydroxy-C-methyl- carbonimidoyl]-4-oxo-1-[4-(trifluoromethoxy)phenyl]cinnoline-3-carboxylate (P14), 5-[(E)-N-hydroxy-C-methyl-carbonimidoyl]-4-oxo-1-[4-(trifluoromethoxy)phenyl] cinnoline-3-carboxylic acid (P15), ethyl 4-oxo-1-[4-(trifluoromethoxy)phenyl]-5-vinyl-cinnoline-3-carboxylate (P16), 4-oxo-1-[4-(trifluoromethoxy) phenyl]-5-vinyl-cinnoline-3-carboxylic acid (P17), ethyl 4-oxo-5-(2-oxoethyl)-1-[4-(trifluoromethoxy) phenyl]cinnoline-3-carboxylate (P18), 5-(4-chloropyrazol-1-oxo-4-oxo-1-[4-(trifluoromethoxy)phenyl]cinnoline-3-carboxylic acid (P19), 4-oxo-1-[4-(trifluoromethoxy)phenyl]-5-[4-(trifluoromethyl) triazol-2-yl]cinnoline-3-carboxylic acid (P20), 4-oxo-1-[4-(trifluoromethoxy)phenyl]-5-[4-(trifluoromethyl) triazol-1-yl]cinnoline-3-carboxylic acid (P21), 4-oxo-1-[4-(trifluoromethoxy)phenyl]-5-[4-(trifluoromethyl) pyrazol-1-yl]cinnoline-3-carboxylic acid (P22), 4-oxo-5-(1-piperidyl)-1-[4-(trifluoromethoxy)phenyl] cinnoline-3-carboxylic acid (P24), ethyl 5-morpholino-4-oxo-1-[4-(trifluoromethoxy)phenyl]cinnoline-3-carboxylate (P26), ethyl 5-(1-ethoxyvinyl)-4-oxo-1-[4-(trifluoromethoxy)phenyl]cinnoline-3-carboxylate (P29), ethyl 5-acetyl-4-oxo-1-[4-(trifluoromethoxy) phenyl]cinnoline-3-carboxylate (P30), ethyl 5-(4-chloropyrazol-1-yl)-4-oxo-1-[4-(trifluoromethoxy)phenyl]cinnoline-3-carboxylate (P32), ethyl 4-oxo-1-[4-(trifluoromethoxy)phenyl]-5-[4-(trifluoromethyl)triazol-1-yl]cinnoline-3-carboxylate (P33), ethyl 4-oxo-1-[4-(trifluoromethoxy)phenyl]-5-[4-(trifluoromethyl)triazol-2-yl]cinnoline-3-carboxylate (P34), ethyl 5-(cyanomethyl)-4-oxo-1-[4-(trifluoromethoxy)phenyl]cinnoline-3-carboxylate (P35), ethyl 5-(difluoromethyl)-4-oxo-1-[4-(trifluoromethoxy)phenyl]cinnoline-3-carboxylate (P36), 5-(difluoromethyl)-4-oxo-1-[4-(trifluoromethoxy)phenyl]cinnoline-3-carboxylic acid (P37), ethyl 5-cyano-4-oxo-1-[4-(trifluoromethoxy)phenyl]cinnoline-3-carboxylate (P35), ethyl 5-nitro-4-oxo-1-[4-(trifluoromethoxy)phenyl]cinnoline-3-carboxylate (P39), 5-nitro-4-oxo-1-[4-(trifluoromethoxy)phenyl]cinnoline-3-carboxylic acid (P40), and 5-cyano-1-(3,4-dimethoxyphenyl)-4-oxo-cinnoline-3-carboxylic acid (P41).

In a further particularly preferred embodiment, the compound of Formula (I) is selected from;

methyl 5-[(E)-N-methoxy-C-methyl-carbonimidoyl]-4-oxo-1-[4-(trifluoromethoxy)phenyl]cinnoline-3-carboxylate (P1), 5-[(E)-N-methoxy-C-methyl-carbon imidoyl]-4-oxo-1-[4-(trifluoromethoxy)phenyl]cinnoline-3-carboxylic acid (P2), methyl 5-(1-ethoxyvinyl)-4-oxo-1-[4-(trifluoromethoxy)phenyl]cinnoline-3-carboxylate (P3), methyl 5-(1-methoxyvinyl)-4-oxo-1-[4-(trifluoromethoxy)phenyl]cinnoline-3-carboxylate (P4). 5-oxazol-2-yl-4-oxo-1-[4-(trifluoroethoxy)phenyl]cinnoline-3-carboxylic acid (P5), methyl 5-cyano-4-oxo-1-[4-(trifluoromethoxy)phenyl]cinnoline-3- carboxylate (P7), 5-cyano-4-oxo-1-[4-(trifluoromethoxy)phenyl]cinnoline-3-carboxylic acid (P3), methyl 5-acetyl-4-oxo-1-[4-(trifluoromethoxy)phenyl]cinnoline-3-carboxylate (P9), 5-acetyl-4-oxo-1-[4-(trinitroethoxy)phenyl]cinnoline-3-carboxylic acid (P10), 1-(4-chlorophenyl)-5-(4-fluorophenoxy)-4-oxo-cinnoline-3-carboxylic acid (P11), ethyl 5-[(E)-N-hydroxy-C-methyl-carbonimidoyl]-4-oxo-1-[4-(trifluoromethoxy)phenyl]cinnoline-3-carboxylate (P14), 5-[(E)-N-hydroxy-C-methyl- carbonimidoyl]-4-oxo-1-[4-(trifluoromethoxy)phenyl]cinnoline-3-carboxylic acid (P15), ethyl 4-oxo-1-[4-(trifluoromethoxy)phenyl]-5-vinyl-cinnoline-3-carboxylate (P16), 4-oxo-1-[4-(trifluoromethoxy)phenyl]-5-vinyl-cinnoline-3-carboxylic acid (P17), ethyl 4-oxo-5-(2-oxoethyl)-1-[4-(trifluoromethoxy)phenyl]cinnoline-3-carboxylate (P16), 5-(4-chloropyrazol-1-oxo-4-oxo-1-[4-(trifluoromethoxy)phenyl]cinnoline-3-carboxylic acid (P19), 4-oxo-1-[4-(trifluoromethoxy)phenyl]-5-[4-(trifluoromethyl)triazol-1-yl]cinnoline-3-carboxylic acid (P21), 4-oxo-1-[4-(trifluoromethoxy)phenyl]-5-[4-(trifluoromethyl)pyrazol-1-yl]cinnoline-3-carboxylic acid (P22), 4-oxo-5-(1-piperidyl)-1-[4-(trifluoromethoxy)phenyl]cinnoline-3-carboxylic acid (P24), ethyl 5-(1-ethoxyvinyl)-4-oxo-1-[4-(trifluoromethoxy)phenyl]cinnoline-3-carboxylate (P29), ethyl 5-acetyl-4-oxo-1-[4-(trifluoromethoxy)phenyl]cinnoline-3- carboxylate (P30), ethyl 5-(4-chloropyrazol-1-yl)-4-oxo-1-[4-(trifluoromethoxy)phenyl]cinnoline-3-carboxylate (P32), ethyl 4-oxo-1-[4-(trifluoromethoxy)phenyl]-5-[4-(trifluoromethyl)triazol-1-yl]cinnoline-3-carboxylate (P33), ethyl 5-(cyanomethyl)-4-oxo-1-[4-(trifluoromethoxy)phenyl]cinnoline-3-carboxylate (P35), ethyl 5-(difluoromethyl)-4-oxo-1-[4-(trifluoromethoxy)phenyl]cinnoline-3-carboxylate (P36), ethyl 5-cyano-4-oxo-1-[4-(trifluoromethoxy)phenyl]cinnoline-3-carboxylate (P38), ethyl 5-nitro-4-oxo-1-[4-(trifluoromethoxy)phenyl]cinnoline-3-carboxylate (P39), 5-nitro-4-oxo-1-[4-(trifluoromethoxy)phenyl]cinnoline-3-carboxylic acid (P40), and 5- cyano-1-(3,4-dimethoxyphenyl)-4-oxo-cinnoline-3-carboxylic acid (P41).

Compounds of the invention can be made as shown in the following schemes, in which, unless otherwise stated, the definition of each variable is as defined above for a compound of Formula (I). General methods for the production of compounds of Formula (I) are described below. Unless otherwise stated in the text, X, $R^1$, $R^2$, $R^3$, $R^4$, $R^5$, and $R^6$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallisation, distillation and filtration.

Scheme 1

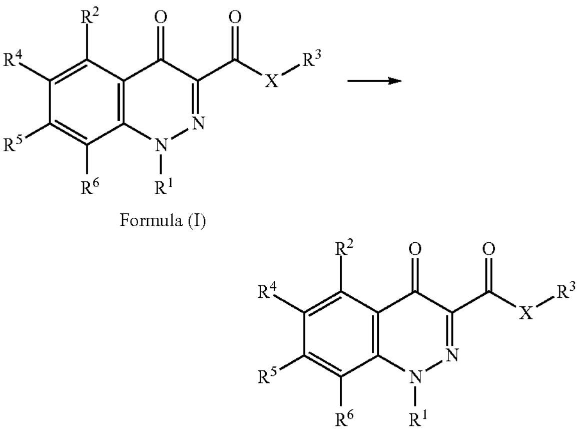

Formula (I)

Formula (I)

A compound of Formula (I) wherein X is oxygen and $R^3$ is hydrogen may be prepared by hydrolysis of a compound of Formula (I) wherein X is oxygen and $R^3$ is not hydrogen, but any other $R^3$ group as defined above, with a suitable base (such as sodium hydroxide or lithium hydroxide), or with a suitable acid (such as trifluoroacetic acid, hydrochloric acid, formic acid or sulfuric acid), in a suitable solvent (such as methanol, ethanol, dichloromethane, chloroform, ethyl acetate or tetrahydrofuran), with an optional co-solvent (such as water). Compounds of Formula (I) may additionally be prepared by methods as described below.

Scheme 2

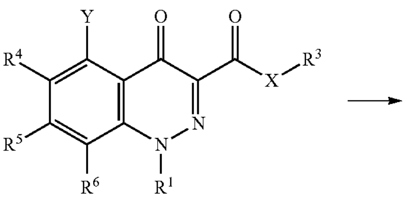

Formula (B)

-continued

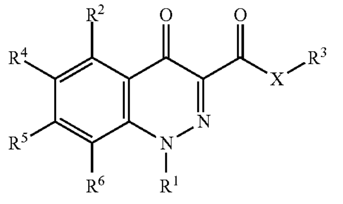

Formula (I)

Compounds of Formula (I) may be prepared from a compound Formula (B) wherein Y is F, Cl, Br or I. In embodiments of the invention when $R^2$ is phenoxy or heterocyclyloxy, and Y is F, compounds of Formula (I) may be prepared by reaction with an appropriately substituted phenol or heterocyclyl alcohol under $S_NAr$ conditions in analogy to literature conditions. Typically the reaction is performed in the presence of a base (such as potassium carbonate), in an organic solvent (such as dimethylacetamide or N,N-dimethylformamide), at elevated temperature (such as 100° C. to 170° C.). This is shown in Scheme 2 above. Compounds of Formula (B) can be prepared by methods described below.

Scheme 3

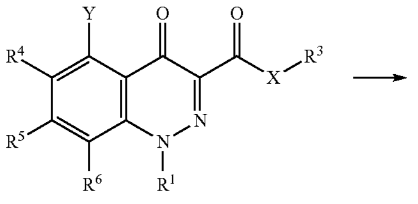

Formula (B)

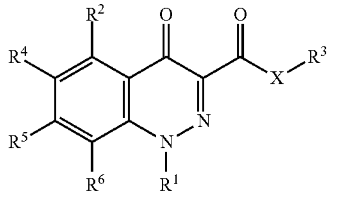

Formula (I)

Compounds of Formula (I) maybe additionally be prepared from a compound of Formula (B) wherein Y is Cl, Br or I. In embodiments of the invention when $R^2$ is $C_2$-$C_6$alkenyloxy and Y is Br, compounds of Formula (I) may be prepared in a Stille reaction by reaction with a stannane reagent in the presence of a palladium catalyst (such as dichlorobis(triphenylphosphine)palladium(II), tetrakis(triphenylphosphine)palladium) or dichloro(1,1'-bis(diphenylphosphanyl)ferrocene)palladium(II) dichloromethane adduct), with or without a base (such as triethylamine), in a suitable organic solvent (such as toluene, 1,4-dioxane or N,N-dimethylformamide), at an elevated reaction temperature (e.g. 120° C.). This is shown in Scheme 3 above.

Scheme 4

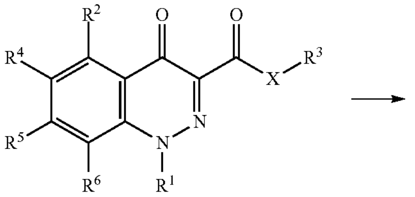

Formula (I)

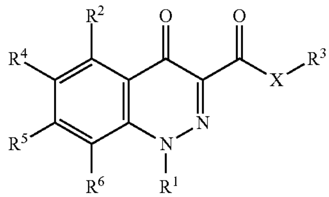

Formula (I)

In a subsequent transformation, compounds of Formula (I) wherein $R^2$ is $C_1$-$C_6$alkylcarbonyl may be prepared from compounds of Formula (I) wherein $R^2$ is $C_2$-$C_6$alkenyloxy by a hydrolysis reaction. Typically, the reaction is performed by treatment with aqueous acid (such as hydrochloric acid), optionally in a suitable organic solvent (such as acetone, 1,4-dioxane or tetrahydrofuran), and at a suitable temperature (20° C. to 60° C.). This is shown in Scheme 4 above.

Scheme 5

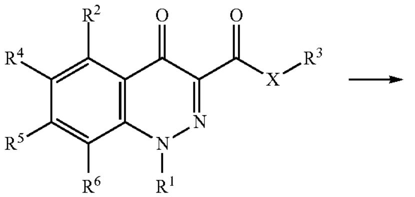

Formula (I)

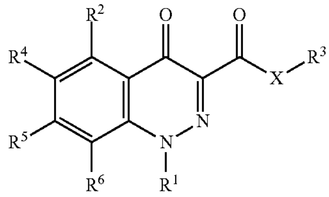

Formula (I)

In a further transformation, compounds of Formula (I) wherein $R^2$ is $-CR^{11}=-OR^{10}$ may be prepared from compounds of Formula (I) wherein $R^2$ is $C_1$-$C_6$alkylcarbonyl by a condensation reaction with a suitable hydroxylamine compound. Typically the reaction is performed with a compound with the formula $H_2NOR^{10}$ as either the freebase or the hydrochloride salt, with or without the addition of a base (such as sodium acetate, pyridine or aqueous potassium hydroxide), in a suitable organic solvent (such as ethanol, dimethylsulfoxide, tetrahydrofuran, dimethylether or methanol) with or without additional water at elevated temperature. This is shown in Scheme 5 above.

Scheme 6

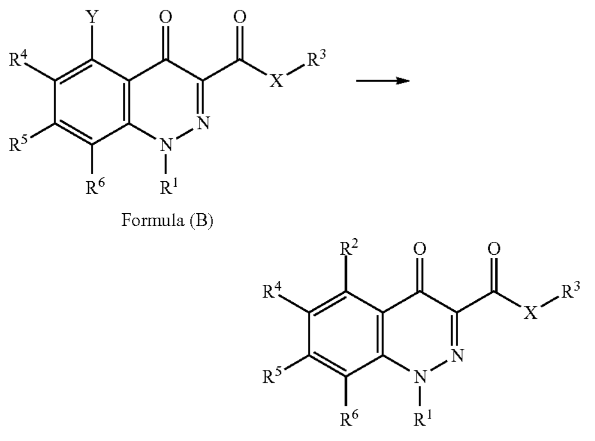
Formula (B)
Formula (I)

In an alternative transformation, a compound of Formula (B) wherein Y is Br may be converted to a compound of Formula (I) wherein $R^2$ is a C-linked heterocycle (such as oxazol-2-yl), by reaction under Stille conditions with, for instance, a heterocyclic stannane in the presence of a catalyst (such as Pd-PEPPSI IPent), and a base (such as cesium fluoride), in a suitable solvent (such as 1,4-dioxane), at elevated temperature (for example 150° C.). This is shown in Scheme 6 above.

Scheme 7

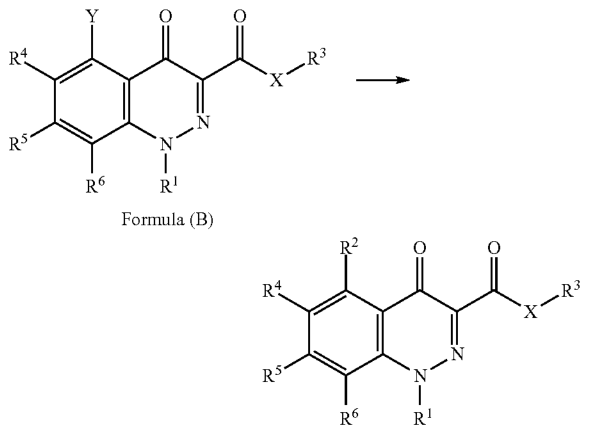
Formula (B)
Formula (I)

In another transformation, a compound of Formula (B) wherein Y is Br may be converted to a compound of Formula (I) wherein $R^2$ is alkyl or phenyl under Suzuki-Miyaura cross-coupling conditions in analogy to literature conditions. Typically the reaction is performed by reaction of a compound of Formula (B) with $R^2$-boronic acid or boroxine in the presence of a suitable catalyst (such as dichlorobis (triphenylphosphine)palladium(II), tetrakis(triphenylphosphine)palladium), tris(dibenzylideneacetone)dipalladium, or dichloro(1,1'-bis(diphenylphosphanyl)ferrocene)palladium (II) dichloromethane adduct), or palladium diacetate optionally with a ligand (such as 2-dicyclohexylphosphino-2',6'-dimethoxybiphenyl) in the presence of a base (such as potassium or cesium carbonate or tripotassium phosphate) in a suitable organic solvent (such as 1,4-dioxane, toluene or tetrahydrofuran) optionally in the presence of water at elevated temperature. This is shown in Scheme 7 above.

Scheme 8

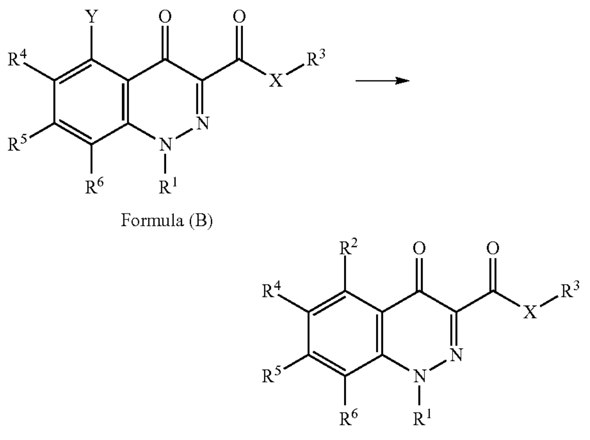
Formula (B)
Formula (I)

In another transformation, a compound of Formula (B) wherein Y is Br may be converted to a compound of Formula (I) wherein $R^2$ is nitrile under Negishi cross-coupling conditions in analogy to literature conditions. Typically the reaction is performed by reaction of a compound of Formula (B) with dicyanozinc in the presence of a suitable catalyst (such as dichlorobis(triphenylphosphine)palladium(II), tetrakis(triphenylphosphine)palladium), tris(dibenzylideneacetone)dipalladium, or dichloro(1,1'-bis(diphenylphosphanyl)ferrocene)palladium(II) dichloromethane adduct), or palladium diacetate optionally with a ligand (such as 2-dicyclohexylphosphino-2',6'-dimethoxybiphenyl) in a suitable organic solvent (such as dimethylformamide), at elevated temperature. This is shown in Scheme 8 above.

Scheme 9

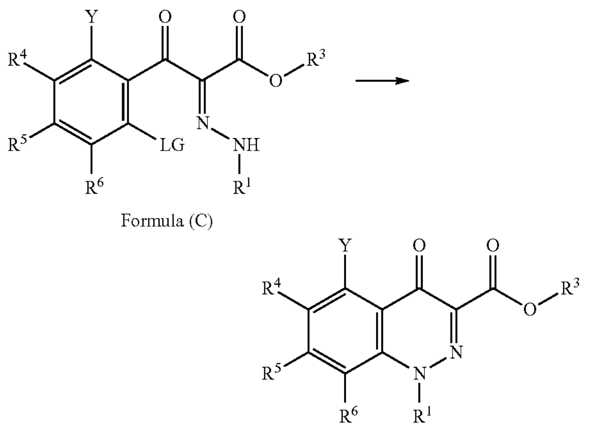
Formula (C)
Formula (B)

A compound of Formula (B) wherein Y is Br, X═O and LG is a suitable leaving group (such as F, Cl or Br), may be prepared from a compound of Formula (C) by treatment with a base (such as a metal hydride e.g. sodium hydride, or potassium carbonate), in a suitable solvent (such as 1,4- dioxane, tetrahydrofuran or N,N-dimethylformamide), at an elevated temperature (for example 100° C.). This is shown in Scheme 9 above.

Scheme 10

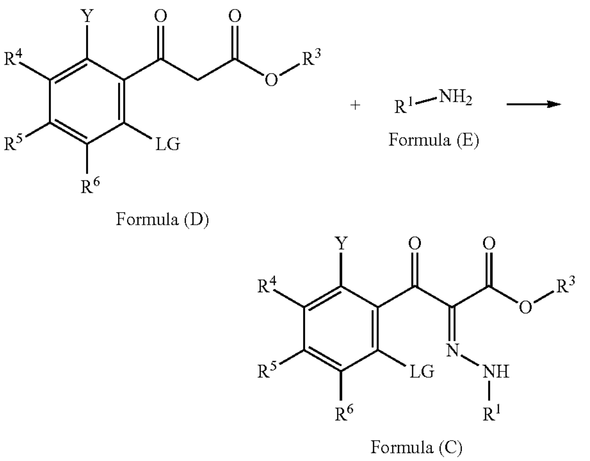

Formula (D) Formula (E) Formula (C)

A compound of Formula (C), wherein Y is Br and wherein LG is a suitable leaving group (such as F, Cl or Br), may be prepared from reaction of 6-keto esters of Formula (D) with an arene diazonium salt. The arene diazonium salts can be prepared in situ by diazotisation of anilines of Formula (E) with sodium nitrite in the presence of acid (such as hydrochloric acid), in water followed by reaction with compounds of Formula (D) in the presence of a suitable base (such as sodium or potassium acetate or potassium carbonate), in a suitable solvent (such as water, methanol or ethanol), at temperatures between 0° C. and 25° C. Compounds of Formula (E) are commercially available or may be prepared by methods familiar to persons skilled in the art. This is shown in Scheme 10 above.

Scheme 11

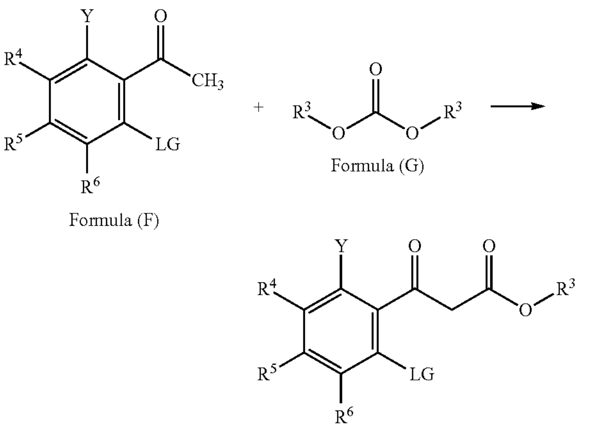

Formula (F) Formula (G) Formula (D)

A dicarbonyl compound of Formula (D) wherein Y is Br and wherein LG is a suitable leaving group (such as F, Cl or Br), may be prepared from a methyl ketone compound of Formula (F) and a diester of Formula (G) via a Claisen condensation by treatment of the methyl ketone with a suitable base (such as potassium t-butoxide or sodium hydride), in a suitable solvent (such as tetrahydrofuran, N,N-dimethylformamide, toluene or 1,4-dioxane), followed by reaction of the mixture with a carbonate ester (such as dimethylcarbonate or diethylcarbonate), at temperatures between 0° C. to 110° C. Compounds of Formula (F) and of Formula (G) are commercially available or may be prepared by methods familiar to persons skilled in the art. This is shown in Scheme 11 above.

The present invention still further provides a method of controlling weeds at a locus said method comprising application to the locus of a weed controlling amount of a composition comprising a compound of Formula (I). Moreover, the present invention may further provide a method of selectively controlling weeds at a locus comprising useful (crop) plants and weeds, wherein the method comprises application to the locus of a weed controlling amount of a composition according to the present invention. ‘Controlling’ means killing, reducing or retarding growth or preventing or reducing germination. It is noted that the compounds of the present invention show a much improved selectivity compared to know, structurally similar compounds. Generally the plants to be controlled are unwanted plants (weeds). ‘Locus’ means the area in which the plants are growing or will grow. The application may be applied to the locus pre-emergence and/or postemergence of the crop plant. Some crop plants may be inherently tolerant to herbicidal effects of compounds of Formula (I).

The rates of application of compounds of Formula (I) may vary within wide limits and depend on the nature of the soil, the method of application (pre- or post-emergence; seed dressing application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2500 g/ha, especially from 25 to 1000 g/ha, more especially from 25 to 250 g/ha.

The application is generally made by spraying the composition, typically by tractor mounted sprayer for large areas, but other methods such as dusting (for powders), drip or drench can also be used.

The term “useful plants” is to be understood as also including useful plants that have been rendered tolerant to herbicides like bromoxynil or classes of herbicides such as, for example, 4-Hydroxyphenylpyruvate dioxygenase (HPPD) inhibitors, ALS inhibitors, for example primisulfuron, prosulfuron and trifloxysulfuron, 5-enol-pyrovyl-shikimate-3-phosphate-synthase (EPSPS) inhibitors, glutamine synthetase (GS) inhibitors or protoporphyrinogen-oxidase (PPO) inhibitors as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term “useful plants” is to be understood as also including useful plants which have been so transformed by the use of recombinant DNA techniques that they are capable of synthesising one or more selectively acting toxins, such as are known, for example, from toxin-producing bacteria, especially those of the genus Bacillus.

Examples of such plants are: YieldGard® (maize variety that expresses a CryIA(b) toxin); YieldGard Rootworm® (maize variety that expresses a CryIIIB (b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure CB Advantage (Bt11 corn borer (CB) trait), Agrisure® RW (corn rootworm trait) and Protecta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

The compounds of Formula (I) (or compositions comprising such) can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and *dicotyledonous* species, *for example Abutilon, Amaranthus, Ambrosia, Chenopodium, Chrysanthemum, Conyza, Galium, Ipomoea, Nasturtium, Side, Sinapis, Solanum, Stellaria, Veronica, Viola* and *Xanthium.*

Compounds of Formula (I) may be used in unmodified form or, preferably, together with the adjuvants conventionally employed in the art of formulation to provide herbicidal compositions, using formulation adjuvants, such as carriers, solvents, and surface-active agents (SAA). The invention therefore further provides a herbicidal composition, comprising at least one compound Formula (I) and an agriculturally acceptable carrier and optionally an adjuvant. An agricultural acceptable carrier is for example a carrier that is suitable for agricultural use. Agricultural carriers are well known in the art.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types. These include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a soluble powder (SP), a wettable powder (WP) and a soluble granule (SG). The formulation type chosen in any instance will depend upon the particular purpose envisaged and the physical, chemical, and biological properties of the compound of Formula (I).

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SAAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SAAs, to produce spontaneously a thermodynamically stable isotropic liquid formulation. A compound of Formula (I) is present initially in either the water or the solvent/SAA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SAAs), spray additives based on oils, for example certain mineral oils or natural plant oils (such as soy bean and rape seed oil), modified plant oils such as methylated rape seed oil (MRSO), and blends of these with other bio-enhancing adjuvants (ingredients which may aid or modify the action of a compound of Formula (I).

Wetting agents, dispersing agents and emulsifying agents may be SAAs of the cationic, anionic, amphoteric or non-ionic type.

Suitable SAAs of the cationic type include quaternary ammonium compounds (for example cetyltrimethyl ammonium bromide), imidazolines and amine salts.

Suitable anionic SAAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates, lignosulphonates and phosphates/sulphates of tristyrylphenols.

Suitable SAAs of the amphoteric type include betaines, propionates and glycinates.

Suitable SAAs of the non-ionic type include condensation products of alkylene oxides, such as ethylene oxide, propylene oxide, butylene oxide or mixtures thereof; with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); lecithins and sorbitans and esters thereof, alkyl polyglycosides and tristyrylphenols.

Suitable suspending agents include hydrophilic colloids (such as polysaccharides, polyvinylpyrrolidone or sodium carboxymethylcellulose) and swelling clays (such as bentonite or attapulgite).

The compounds of present invention can also be used in mixture with one or more additional herbicides and/or plant growth regulators. Examples of such additional herbicides or plant growth regulators include acetochlor, acifluorfen (including acifluorfen-sodium), aclonifen, ametryn, amicarbazone, aminopyralid, aminotriazole, atrazine, beflubutamid-M, benquitrione, bensulfuron (including bensulfuron-methyl), bentazone, bicyclopyrone, bilanafos, bipyrazone, bispyribac-sodium, bixlozone, bromacil, bromoxynil, butachlor, butafenacil, carfentrazone (including carfentrazone-ethyl), cloransulam (including cloransulam-methyl), chlorimuron (including chlorimuron-ethyl), chloratoluron, chlorsulfuron, cinmethylin, clacyfos, clethodim, clodinafop (including clodinafop-propargyl), clomazone, clopyralid, cyclopyranil, cyclopyrimorate, cyclosulfamuron, cyhalofop (including cyhalofop-butyl), 2,4-D (including the choline salt and 2-ethylhexyl ester thereof), 2,4-DB, desmedipham, dicamba (including the aluminium, aminopropyl, bis-aminopropylmethyl, choline, dichloroprop, diglycolamine, dimethylamine, dimethylammonium, potassium and sodium salts thereof) diclosulam, diflufenican, diflufenzopyr, dimethachlor, dimethenamid-P, dioxopyritrione, diquat dibromide, diuron, epyrifenacil, ethalfluralin, ethofumesate, fenoxaprop (including fenoxaprop-P-ethyl), fenoxasulfone, fenpyrazone, fenquinotrione, fentrazamide, flazasulfuron, florasulam, florpyrauxifen (including florpyrauxifen-benzyl), fluazifop (including fluazifop-P-butyl), flucarbazone (including flucarbazone-sodium), flufenacet, flumetsulam, flumioxazin, fluometuron, flupyrsulfuron (including flupyrsulfuron-methyl-sodium), fluroxypyr (including fluroxypyr-meptyl), fomesafen, foramsulfuron, glufosinate (including L-glufosinate and the ammonium salts of both), glyphosate (including the diammonium, isopropylammonium and potassium salts thereof), halauxifen (including halauxifen-methyl), haloxyfop (including haloxyfop-methyl), hexazinone, hydantocidin, imazamox (including R-imazamox), imazapic, imazapyr, imazethapyr, indaziflam, iodosulfuron (including iodosulfuron-methyl-sodium), iofensulfuron (including iofensulfuron-sodium), ioxynil, isoproturon, isoxaflutole, lancotrione, MCPA, MCPB, mecoprop-P, mesosulfuron (including mesosulfuron-methyl), mesotrione, metamitron, metazachlor, methiozolin, metolachlor, metosulam, metribuzin, metsulfuron, napropamide, nicosulfuron, norflurazon, oxadiazon, oxasulfuron, oxyfluorfen, paraquat dichloride, pendimethalin, penoxsulam, phenmedipham, picloram, pinoxaden, pretilachlor, primisulfuron-methyl, prometryne, propanil, propaquizafop, propyrisulfuron, propyzamide, prosulfocarb, prosulfuron, pyraclonil, pyraflufen (including pyraflufen-ethyl), pyrasulfolole, pyridate, pyriftalid, pyrimisulfan, pyroxasulfone, pyroxsulam, quinclorac, quinmerac, quizalofop (including quizalofop-P-ethyl and quizalofop-P-tefuryl), rimisoxafen, rimsulfuron, saflufenacil, sethoxydim, simazine, S-metalochlor, sulfentrazone, sulfosulfuron, tebuthiuron, tefuryltrione, tembotrione, terbuthylazine, terbutryn, tetflupyrolimet, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, triflusulfuron, tripyrasulfone, 3-(2-chloro-4-fluoro-5-(3-methyl-2,6-dioxo-4-trifluoromethyl-3,6-dihydropyrimidin-1(2H)-yl)phenyl)-5-methyl-4,5-dihydroisoxazole-5-carboxylic acid ethyl ester, 4-hydroxy-1-methoxy-5-methyl-3-[4-(trifluoromethyl)-2-pyridyl]imidazolidin-2-one, 4-hydroxy-1,5-dimethyl-3-[4-(trifluoromethyl)-2-pyridyl]imidazolidin-2-one, 5-ethoxy-4-hydroxy-1-methyl-3-[4-(trifluoromethyl)-2-pyridyl]imidazolidin-2-one, 4-hydroxy-1-methyl-3-[4-(trifluoromethyl)-2-pyridyl]imidazolidin-2-one, 4-hydroxy-1,5-dimethyl-3-[1-methyl-5-(trifluoromethyl)pyrazol-3-yl]imidazolidin-2-one, (4R)1-(5-tert-butylisoxazol-3-yl)-4-ethoxy-5-hydroxy-3-methyl-imidazolid in-2-one, 4-amino-3-chloro-5-fluoro-6-(7-fluoro-1H-indol-6-yl)pyridine-2-carboxylic acid (including agrochemically acceptable esters thereof, for example, methyl 4-amino-3-chloro-5-fluoro-6-(7-fluoro-1H-indol-6-yl)pyridine-2-carboxylate, prop-2-ynyl 4-amino-3-chloro-5-fluoro-6-(7-fluoro-1H-indol-6-yl)pyridine-2-carboxylate and cyanomethyl 4-amino-3-chloro-5-fluoro-6-(7-fluoro-1H-indol-6-yl)pyridine-2-carboxylate), 3-ethylsulfanyl-N-(1,3,4-oxadiazol-2-yl)-5-(trifluoromethyl)-[1,2,4]triazolo[4,3-a]pyridine-8-carboxamide, 3-(isopropylsulfanylmethyl)-N-(5-methyl-1,3,4-oxadiazol-2-yl)-5-(trifluoromethyl)-[1,2,4]triazolo[4,3-a]pyridine-8-carboxamide, 3-(isopropylsulfonylmethyl)-N-(5-methyl-1,3,4-oxadiazol-2-yl)-5-(trifluoroethyl)-[1,2,4]triazolo[4,3-a]pyridine-8-carboxamide, 3-(ethylsulfonylmethyl)-N-(5-methyl-1,3,4-oxadiazol-2-yl)-5-(trifluoroethyl)-[1,2,4]triazolo[4,3-a]pyridine-8-carboxamide, ethyl 2-[[3-[[3-chloro-5-fluoro-6-]3-methyl-2,6-dioxo-4-(trifluoromethyl)pyrimidin-1-yl]-2-pyridyl]oxy]acetate and 6-chloro-4-(2,7-dimethyl-1-naphthyl)-5-hydroxy-2-methyl-pyridazin-3-one.

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil.

The mixing partners of the compound of Formula (I) may also be in the form of esters or salts, as mentioned e.g. in The Pesticide Manual, Sixteenth Edition, British Crop Protection Council, 2012. The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil.

Particularly preferred are mixtures of a compound of Formula (I) with cyprosulfamide, isoxadifen-ethyl, cloquintocet-mexyl and/or metcamifen.

The safeners of the compound of Formula (I) may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048.

Preferably the mixing ratio of compound of Formula (I) to safener is from 100:1 to 1:10, especially from 20:1 to 1:1.

The compounds of Formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes, and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders, or Fertilizers. Such carriers are for example described in WO 97/33890.

The compounds of Formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compound of Formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbicides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The table below illustrates examples of individual compounds of Formula (I) according to the invention:

(I)

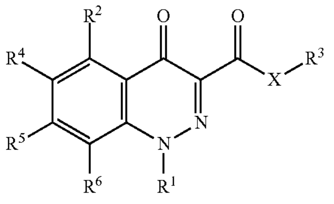

TABLE 1

Individual compounds of formula (I) according to the invention

| No. | $R^1$ | $R^2$ | $R^3$ | $R^4$ | $R^5$ | $R^6$ |
|---|---|---|---|---|---|---|
| 001 | 4-(trifluoromethoxy)phenyl | N-methoxy-C-methyl-carbonimidoyl | Et | H | H | H |
| 002 | 4-(trifluoromethoxy)phenyl | N-methoxy-C-methyl-carbonimidoyl | Me | H | H | H |
| 003 | 4-(trifluoromethoxy)phenyl | N-methoxy-C-methyl-carbonimidoyl | H | H | H | H |
| 004 | 4-(trifluoromethoxy)phenyl | 1-ethoxyvinyl | Et | H | H | H |
| 005 | 4-(trifluoromethoxy)phenyl | 1-ethoxyvinyl | Me | H | H | H |
| 006 | 4-(trifluoromethoxy)phenyl | 1-ethoxyvinyl | H | H | H | H |
| 007 | 4-(trifluoromethoxy)phenyl | 1-methoxyvinyl | Et | H | H | H |
| 008 | 4-(trifluoromethoxy)phenyl | 1-methoxyvinyl | Me | H | H | H |
| 009 | 4-(trifluoromethoxy)phenyl | 1-methoxyvinyl | H | H | H | H |
| 010 | 4-(trifluoromethoxy)phenyl | oxazol-2-yl | Et | H | H | H |
| 011 | 4-(trifluoromethoxy)phenyl | oxazol-2-yl | Me | H | H | H |
| 012 | 4-(trifluoromethoxy)phenyl | oxazol-2-yl | H | H | H | H |
| 013 | 4-(trifluoromethoxy)phenyl | 4-fluorophenyl | Et | H | H | H |
| 014 | 4-(trifluoromethoxy)phenyl | 4-fluorophenyl | Me | H | H | H |
| 015 | 4-(trifluoromethoxy)phenyl | 4-fluorophenyl | H | H | H | H |
| 016 | 4-(trifluoromethoxy)phenyl | cyano | Et | H | H | H |
| 017 | 4-(trifluoromethoxy)phenyl | cyano | Me | H | H | H |
| 018 | 4-(trifluoromethoxy)phenyl | cyano | H | H | H | H |
| 019 | 4-(trifluoromethoxy)phenyl | acetyl | Et | H | H | H |
| 020 | 4-(trifluoromethoxy)phenyl | acetyl | Me | H | H | H |
| 021 | 4-(trifluoromethoxy)phenyl | acetyl | H | H | H | H |
| 022 | 4-(trifluoromethoxy)phenyl | 4-fluorophenoxy | Et | H | H | H |
| 023 | 4-(trifluoromethoxy)phenyl | 4-fluorophenoxy | Me | H | H | H |
| 024 | 4-(trifluoromethoxy)phenyl | 4-fluorophenoxy | H | H | H | H |
| 025 | 4-chlorophenyl | N-methoxy-C-methyl-carbonimidoyl | Et | H | H | H |
| 026 | 4-chlorophenyl | N-methoxy-C-methyl-carbonimidoyl | Me | H | H | H |
| 027 | 4-chlorophenyl | N-methoxy-C-methyl-carbonimidoyl | H | H | H | H |
| 028 | 4-chlorophenyl | 1-ethoxyvinyl | Et | H | H | H |
| 029 | 4-chlorophenyl | 1-ethoxyvinyl | Me | H | H | H |

TABLE 1-continued

| Individual compounds of formula (I) according to the invention | | | | | | |
|---|---|---|---|---|---|---|
| No. | $R^1$ | $R^2$ | $R^3$ | $R^4$ | $R^5$ | $R^6$ |
| 030 | 4-chlorophenyl | 1-ethoxyviny | H | H | H | H |
| 031 | 4-chlorophenyl | 1-methoxyvinyl | Et | H | H | H |
| 032 | 4-chlorophenyl | 1-methoxyvinyl | Me | H | H | H |
| 033 | 4-chlorophenyl | 1-methoxyvinyl | H | H | H | H |
| 034 | 4-chlorophenyl | oxazol-2-yl | Et | H | H | H |
| 035 | 4-chlorophenyl | oxazol-2-yl | Me | H | H | H |
| 036 | 4-chlorophenyl | oxazol-2-yl | H | H | H | H |
| 037 | 4-chlorophenyl | 4-fluorophenyl | Et | H | H | H |
| 038 | 4-chlorophenyl | 4-fluorophenyl | Me | H | H | H |
| 039 | 4-chlorophenyl | 4-fluorophenyl | H | H | H | H |
| 040 | 4-chlorophenyl | cyano | Et | H | H | H |
| 041 | 4-chlorophenyl | cyano | Me | H | H | H |
| 042 | 4-chlorophenyl | cyano | H | H | H | H |
| 043 | 4-chlorophenyl | acetyl | Et | H | H | H |
| 044 | 4-chlorophenyl | acetyl | Me | H | H | H |
| 045 | 4-chlorophenyl | acetyl | H | H | H | H |
| 046 | 4-chlorophenyl | 4-fluorophenoxy | Et | H | H | H |
| 047 | 4-chlorophenyl | 4-fluorophenoxy | Me | H | H | H |
| 048 | 4-chlorophenyl | 4-fluorophenoxy | H | H | H | H |

Table A-1 provides 48 compounds A-1.001 to A.1.048 of Formula (I) wherein X is oxygen, and $R^1$, $R^2$, $R^3$, $R^4$, $R^5$, and $R^6$ are as defined in Table 1.

Formulation Examples

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |

-continued

| Emulsifiable concentrate | |
|---|---|
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 pacts of an aromatic solvent and 7 parts of toluene diisocyanate/polymethylene-polyphenylisocyanate-mixture (8:1). This mixture is emulsified in a mixture of 1.2 parts of polyvinyl alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

EXAMPLES

The following non-limiting examples provide specific synthesis methods for representative compounds of the present invention, as referred to in Table 2 below.

List of Abbreviations

° C.=degrees Celsius, $CDCl_3$=chloroform-d, d=doublet, DCM=dichloromethane, dppf=1,1'-ferrocenediyl-bis(diphenylphosphine), m=multiplet, MHz=megahertz, Pd-PEPPSI IPent=Dichloro[1,3-bis(2,6-Di-3-pentylphenyl)imidazol-2-ylidene](3-chloropyridyl)palladium(II), q=quartet, s=singlet Example 1: Synthesis of 5-(N-methoxy-C-methyl-carbonimidoyl)-4-oxo-1-[4-(trifluoromethoxy) phenyl]cinnoline-3-carboxylic acid (Compound P2)

Step 1: Synthesis of methyl 3-(2-bromo-6-fluoro-phenyl)-3-oxo-propanoate

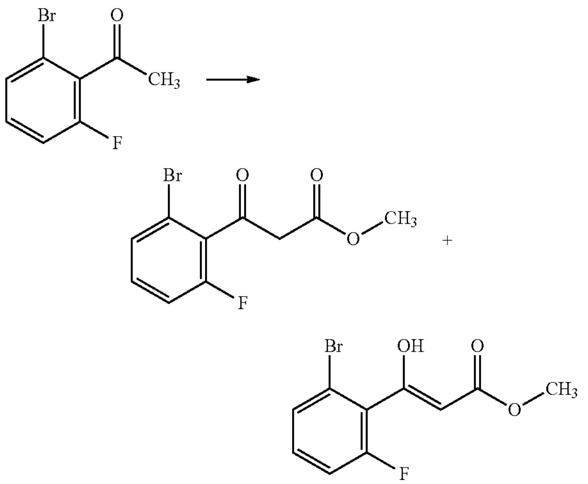

To a stirred solution of 1-(2-bromo-6-fluoro-phenyl)ethanone (5.0 g, 23.0 mmol) and dimethyl carbonate (37.3 g, 406 mmol) in N,N-dimethylformamide (20 mL) under nitrogen and cooled to 0° C. was added portionwise sodium hydride (2.8 g, 69.1 mmol, 60 mass %). The reaction was allowed to warm to room temperature and stirred for 24 hours. The reaction mixture was poured slowly onto ice and acidified to pH3 with concentrated hydrochloric acid. The phases were separated and the aqueous was re-extracted with diethyl ether. The combined organic extracts were dried over magnesium sulfate and evaporated to dryness under reduced pressure. The crude residue was purified by flash chromatography on silica gel using a gradient of 0-30% ethyl acetate in cyclohexane as eluent to give the desired product (mixture of tautomers) as a colourless liquid (3.34 g, 12.1 mmol, 52%). $^1$H NMR (400 MHz, $CDCl_3$) δ=7.46-7.36 (m, 1H), 7.33-7.28 (m, 1H), 7.15-6.98 (m, 1H), 3.98-3.90 (m, 2H), 3.79-3.61 (m, 3H) (data for keto form only)

Step 2: Synthesis of Methyl (2E)-3-(2-bromo-6-fluoro-phenyl)-3-oxo-2-[[4-(trifluoromethoxy) phenyl]hydrazono]propanoate

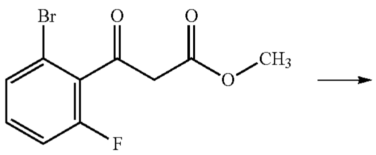

-continued

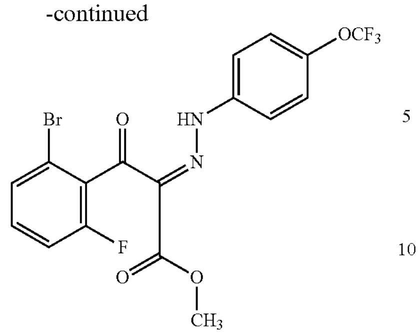

To a solution of 4-(trifluoromethoxy)aniline (2.12 g, 12.0 mmol) in hydrochloric acid (10.0 mL, 60.1 mmol, 6 mol/L) at 0° C. was added dropwise a solution of sodium nitrite (0.921 g, 13.2 mmol) in water (2.4 mL, 12.0 mmol). The reaction mixture was stirred for 30 minutes at 0° C. before being added portionwise to a suspension of methyl 3-(2-bromo-6-fluoro-phenyl)-3-oxo-propanoate (3.34 g, 12.0 mmol) and potassium acetate (6.0 g, 60.1 mmol) in water (2.4 mL) resulting in formation of a yellow solid. The reaction mixture was stirred for 45 minutes and then allowed to warm to room temperature. After 90 minutes, the reaction mixture was filtered and the solid was collected by filtration to give the desired product as a yellow solid (3.5 g, 7.6 mmol, 64%). $^1$H NMR (400 MHz, $CDCl_3$) δ=13.25-13.07 (m, 1H), 7.45-7.39 (m, 1H), 7.33-7.28 (m, 1H), 7.18-7.07 (m, 3H), 7.02-6.92 (m, 2H), 4.08-3.97 (m, 3H)

Step 3: Synthesis of methyl 5-bromo-4-oxo-1-[4-(trifluoromethoxy)phenyl]cinnoline-3-carboxylate

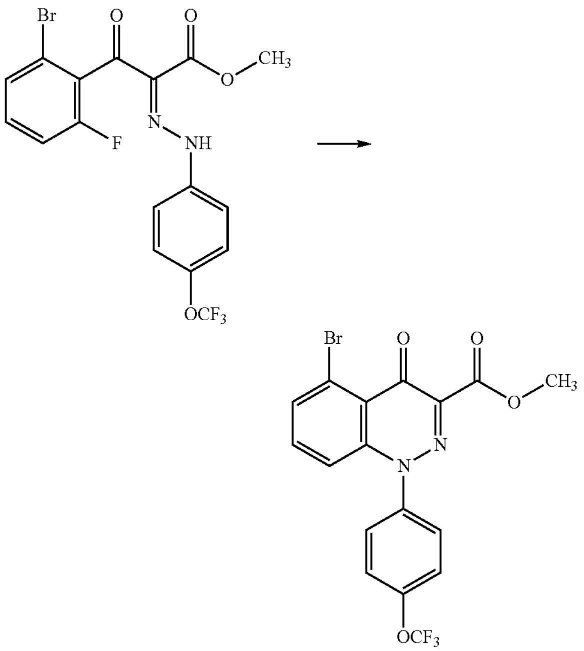

To a solution of methyl (2Z)-3-(2-Promo-6-fluoro-phenyl)-3-oxo-2-[[4-(trifluoromethoxy)phenyl]hydrazono]propanoate (3.53 g, 7.6 mind) in dimethylformamide (30 mL) was added potassium carbonate (0.85 g, 8.38 mmol). The reaction mixture was heated at 100° C. for 1.5 hours. The cooled reaction mixture was poured onto ice upon which a pale solid crashed out of solution. The solid was collected by filtration to give the desired product as an off-white powder (3.3 g, 7.5 mmol, 98%). $^1$H NMR (400 MHz, $CDCl_3$) δ=7.61-7.53 (m, 3H), 7.46-7.41 (m, 2H), 7.16-7.05 (m, 1H), 6.97-6.37 (m, 1H), 4.01-3.94 (m, 3H)

Step 4: Synthesis of methyl 5-(1-ethoxyvinyl)-4-oxo-1-[4-(trifluoromethoxy)phenyl]cinnoline-3-carboxylate (Compound P3)

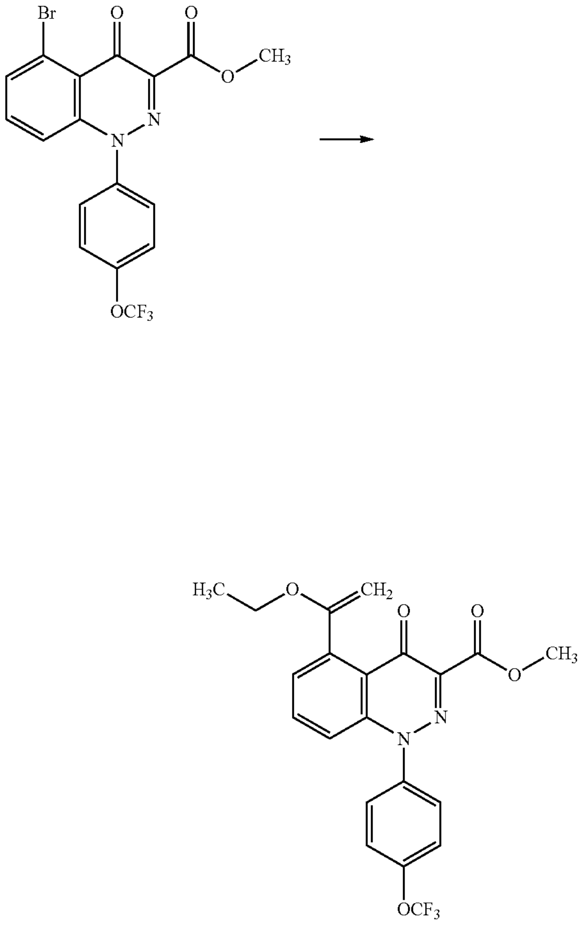

To dichlorobis(triphenylphosphine)palladium(11) (0.048 g, 0.068 frump was added a solution of methyl 5-bromo-4-oxo-1-[4-(trifluoromethoxy)phenyl]cinnoline-3-carboxylate (0.60 g, 1.35 mmol) in toluene (20 mL). The reaction mixture was degassed under a stream of nitrogen for 5 minutes before addition of tributyl(1-ethoxyvinyl)stannane (1.47 g, 4.1 mmol). The reaction mixture was heated under microwave irradiation at 120° C. for 60 minutes. The reaction mixture was evaporated to dryness under reduced pressure to afford a brown gum which was purified by flash chromatography on silica gel using a gradient of 5-100% ethyl acetate in cyclohexane as eluent to give the desired product as an off-white solid (0.43 g, 0.99 mmol, 70%). $^1$H NMR (400 MHz, $CDCl_3$) δ=7.62-7.52 (m, 3H), 7.48-7.35 (m, 3H), 7.19-7.08 (m, 1H), 4.44-4.39 (m, 1H), 4.28-4.25 (m, 1H), 4.12-4.03 (m, 2H), 3.98-3.88 (m, 3H), 1.41-1.31 (m, 3H)

Step 5: Synthesis of methyl 5-acetyl-4-oxo-1-[4-(trifluoromethoxy)phenyl]cinnoline-3-carboxylaxylate (Compound P9)

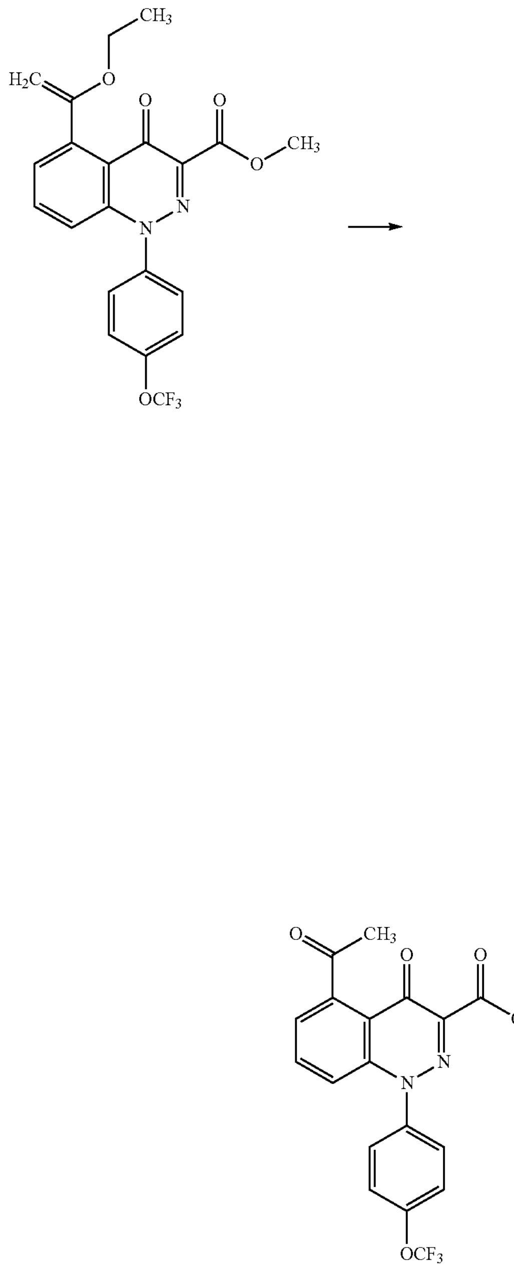

To methyl 5-(1-ethoxyvinyl)-4-oxo-1-[4-(trifluoromethoxy)phenyl]cinnoline-3-carboxylate (0.416 g, 0.96 mmol) in acetone (5.5 mL) was added aqueous hydrochloric acid (2M, 5.5 mL, 11 mmol). The reaction mixture was heated at 60'C for 3.5 hours. The reaction mixture was evaporated under reduced pressure to remove the acetone and the solids were collected by filtration to give desired product as an off-white powder (0.36 g, 0.87 mmol, 94%). $^1H$ NMR (400 MHz, $CDCl_3$) δ=7.73-7.67 (m, 1H), 7.59-7.51 (m, 2H), 7.52-7.42 (m, 2H), 7.29-7.20 (m, 2H), 4.03-3.89 (m, 3H), 2.65-2.52 (m, 3H)

Step 6: Synthesis of methyl 5-(N-methoxy-C-methyl-carbonimidoyl)-4-oxo-1-[4-(trifluoro methoxy)phenyl]cinnoline-3-carboxylate (Compound P1)

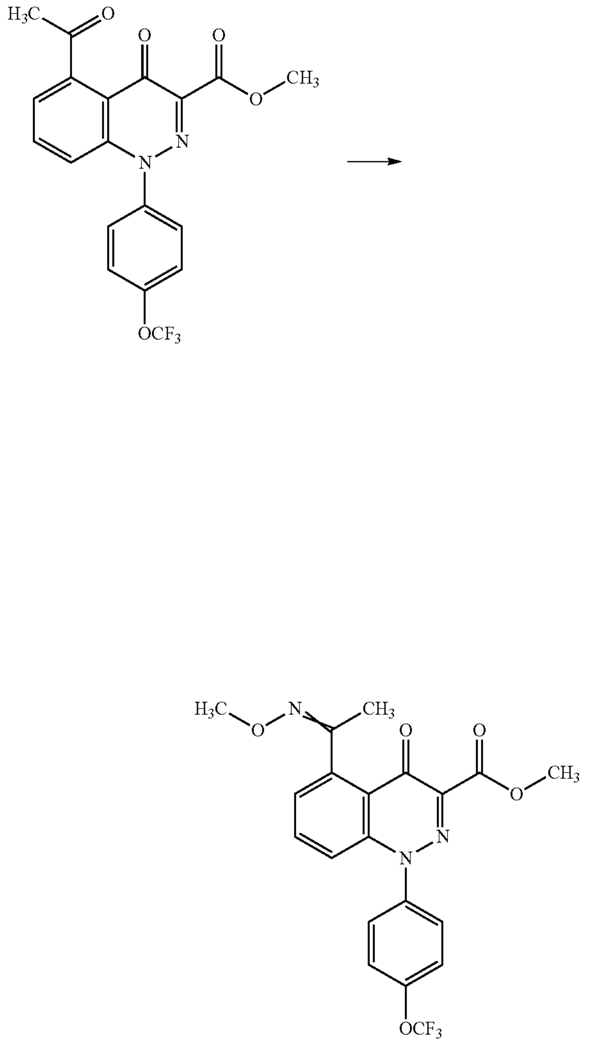

To methyl 5-acetyl-4-oxo-1-[4-(trifluoromethoxy)phenyl] cinnoline-3-carboxylate (0.47 g, 1.16 mmol) in a mixture of methanol (5 mL) and water (1.5 mL) was added 0-methylhydroxylamine hydrochloride (0.15 g, 1.7 mmol) and sodium acetate (0.14 g, 1.74 mmol). The reaction mixture was heated at reflux for 4.5 hours and then stood at room temperature for 3 days. More O-methylhydroxylamine hydrochloride (0.15 g, 1.74 mmol) and sodium acetate (0.14 g, 1.74 mmol) were added and the reaction mixture was heated for 5 hours. The cooled reaction mixture was diluted with 2M aqueous hydrochloric acid and the precipitated solid was collected by filtration. The solid was purified by flash chromatography on silica gel using a gradient of 5-100% ethyl acetate in cyclohexane as eluent to give the desired product as a white solid (0.17 g, 0.39 mmol, 34%). $^1H$ NMR (400 MHz, $CDCl_3$) δ=7.67-7.59 (m, 1H), 7.58-7.51 (m, 2H), 7.50-7.43 (m, 2H), 7.37-7.30 (m, 1H), 7.23-7.15 (m, 1H), 3.99-3.94 (m, 6H), 2.28-2.21 (m, 3H)

Step 7: Synthesis of 5-(N-methoxy-C-methyl-carbonimidoyl)-4-oxo-1-[4-(trifluoromethoxy) phenyl] cinnoline-3-carboxylic acid (Compound P2)

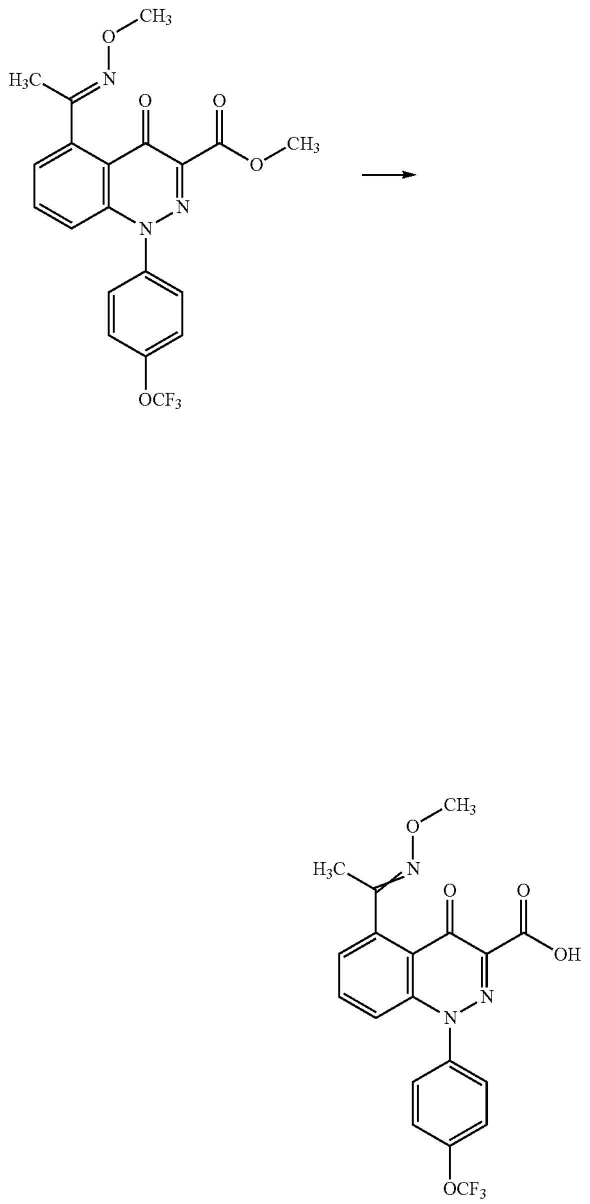

To a solution of methyl 5-(N-methoxy-C-methyl-carbonimidoyl)-4-oxo-1-[4-(trifluoromethoxy)phenyl]cinnoline-3-carboxylate (0.038 g, 0.087 mmol) in methanol (1 mL) and water (0.5 mL) was added lithium hydroxide monohydrate (0.0073 g, 0.17 mmol). The resultant solution was heated to 65° C. for 2 hours. The methanol was removed under reduced pressure and the pH of the resultant aqueous reaction mixture was adjusted to pH2 by the addition of concentrated hydrochloric acid. The precipitated solid was collected by filtration and washed with cyclohexane to give desired product as a white powder (0.036 g, 0.084 mmol, 97%). $^1$H NMR (400 MHz, $CDCl_3$) δ=7.86-7.74 (m, 1H), 7.63-7.55 (m, 2H), 7.55-7.45 (m, 3H), 7.44-7.35 (m, 1H), 4.06-3.95 (m, 3H), 2.32-2.17 (m, 3H)

Example 2: Synthesis of 5-oxazol-2-yl-4-oxo-1-[4-(trifluoromethoxy)phenyl]cinnoline-3-carboxylic acid (Compound P5)

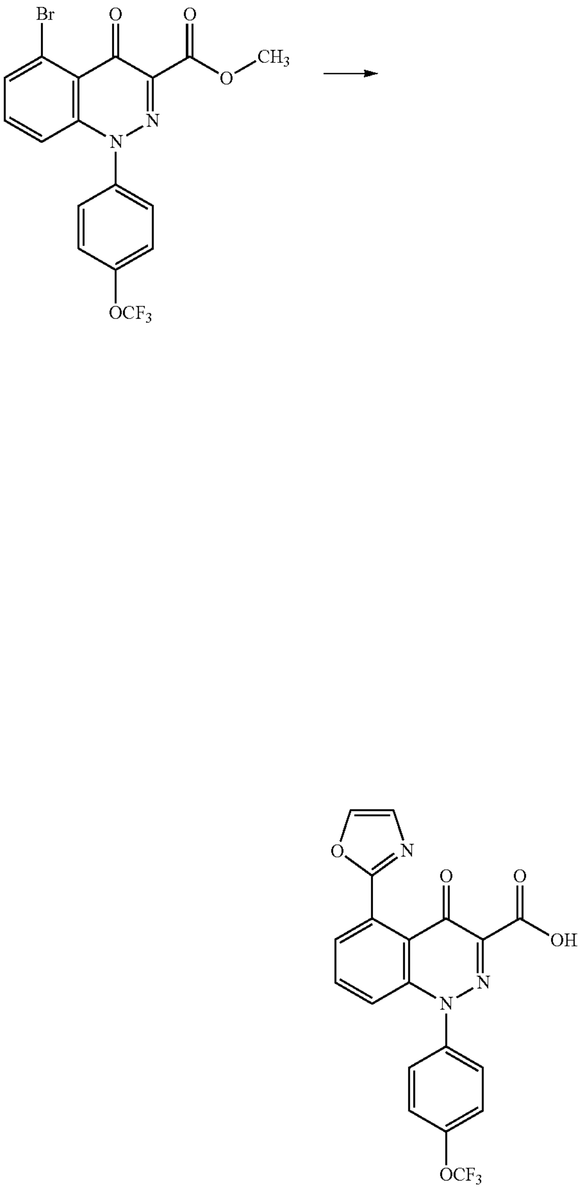

A mixture of methyl 5-bromo-4-oxo-1-[4-(trifluoromethoxy)phenyl]cinnoline-3-carboxylate (0.20 g, 0.45 mmol), Pd-PEPPSI IPent Catalyst (0.029 g, 0.0361 mmol), cesium fluoride (0.14 q, 0.90 mmol) and tributyl(oxazol-2-yl)stannane (0.19 g, 0.54 mmol) in 1,4-dioxane (4 mL) was heated under microwave irradiation at 150° C. for 30+30 minutes. The reaction mixture was diluted with 2M hydrochloric acid and extracted with ethyl acetate. The combined organics were concentrated to dryness under reduced pressure. The crude residue was purified by mass-directed reverse phase HPLC and then triturated with diethyl ether to give the desired product as a pale-yellow powder (0,026 g, 0,063 mmol, 14%). $^1$H NMR (400 MHz, 00013) δ=7.91-7.81 (m, 3H), 7.65-7.59 (m, 2H), 7.58-7.47 (m, 3H), 7.40-7.35 (m, 1H)

Example 3: Synthesis of 5-acetyl-4-oxo-1-[4-(trifluoromethoxy)phenyl]cinnoline-3-carboxylic acid (Compound 110)

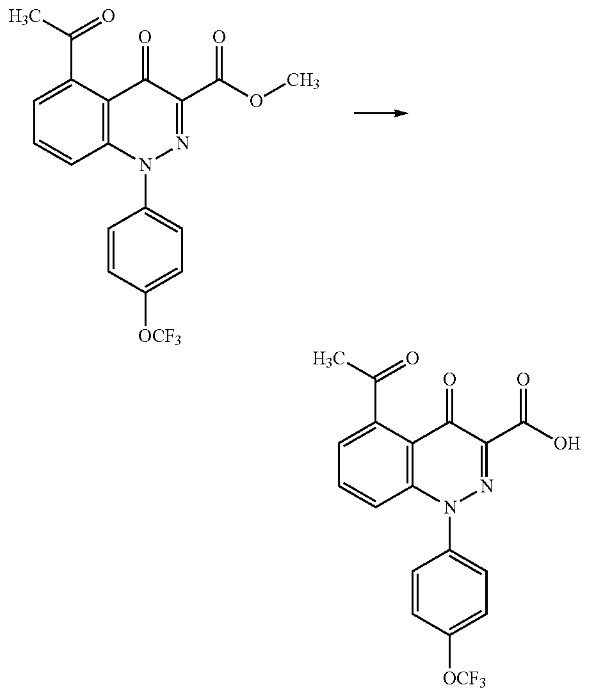

To a suspension of 5-acetyl-4-oxo-1-[4-(trifluoromethoxy)phenyl]cinnoline-3-carboxylic acid (0.052 g, 0.13 mmol) in methanol (1.5 mL) was added a solution of lithium hydroxide hydrate (0.026 g, 0.61 mmol) in water (0.15 mL). The reaction mixture was stirred at room temperature for 2.5 hours. The reaction mixture was acidified by the addition of 2M aqueous hydrochloric acid upon which a pale solid crashed out of solution. The suspended solid was collected by filtration and air-dried to give the desired product as a white powder (0.052 g, 0.13 mmol, 87%). $^1$H NMR (400 MHz, $CDCl_3$) δ=7.90-7.83 (m, 1H), 7.66-7.58 (m, 2H), 7.53-7.49 (m, 2H), 7.47-7.43 (m, 2H), 2.67-2.60 (m, 3H)

Example 4: Synthesis of methyl 5-(1-methoxyvinyl)-4-oxo-1-[4-(trifluoromethoxy)phenyl]cinnoline-3-carboxylate (Compound P4)

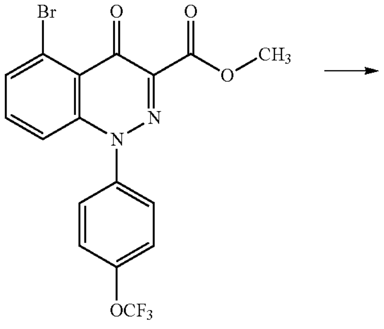

-continued

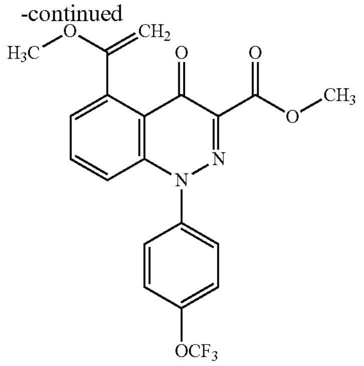

To dichlorobis(triphenylphosphine)palladium(11) (0.024 g, 0.034 mmol) was added a solution of methyl 5-bromo-4-oxo-1-[4-(trifluoromethoxy)phenyl]cinnoline-3-carboxylate (0.30 g, 0.68 mmol) in toluene (5 mL). The mixture was degassed with nitrogen for 5 minutes after which tributyl (1-methoxyvinyl)stannane (0.71 g, 2.03 mmol) was added. The reaction mixture was heated under microwave irradiation at 120° C. for 45 minutes. The cooled reaction mixture was filtered through diatomaceous earth and the filtrated was concentrated to dryness under reduced pressure. The crude residue was purified by flash chromatography on silica gel using a gradient of 5-100% ethyl acetate in cyclohexane as eluent to give the desired product as an off-white solid (0,086 g, 0.20 mmol, 30%). $^1$H NMR (400 MHz, $CDCl_3$) 7.58-7.49 (m, 3H), 7.49-7.44 (m, 2H), 7.43-7.37 (m, 1H), 7.22-7.10 (m, 1H), 4.44-4.38 (m, 1H), 4.27-4.21 (m, 1H), 3.97-3.91 (m, 3H), 3.86-3.79 (m, 3H)

Example 5: Synthesis of 1-(4-chlorophenyl)-5-(4-fluorophenoxy)-4-oxo-cinnoline-3-carboxylic acid (Compound P11)

Step 1: Synthesis of ethyl 3-(2,6-difluorophenyl)-3-oxo-propanoate

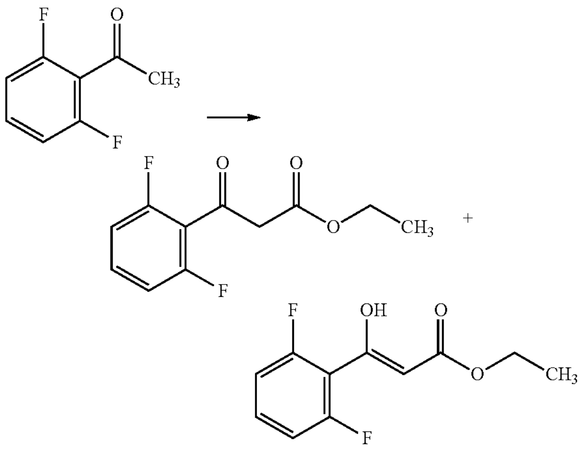

To a solution of potassium 3-ethoxy-3-oxo-propanoic acid (6.11 g, 35.7 mmol) in acetonitrile (66 mL) at 0° C. and under nitrogen was added triethylamine (3.78 g, 37.4 mmol) and dichloromagnesium (4.1 g, 42.5 mmol). The reaction mixture was stirred at room temperature for 3.5 hours. The reaction mixture was cooled to 0° C. and 2,6-difluorobenzoyl chloride (3.0 g, 17 mmol) was added portionwise. The reaction mixture was stirred for 1.5 hours in ice and then at room temperature for 2 hours before standing for 18 hours. The reaction mixture was evaporated under reduced pressure and azeotroped with toluene. The residue was suspended in ethyl acetate (50 mL) and 2M aqueous hydrochloric acid.

The phases were separated and the aqueous was re-extracted twice with ethyl acetate. The combined organic extracts were dried over magnesium sulfate and evaporated to dryness under reduced pressure to give the crude desired product (mixture of tautomers) as a pale-yellow liquid (4.5 g, 20 mmol). $^1$H NMR (400 MHz, $CDCl_3$) δ=7.53-7.37 (m, 1H), 7.04-6.88 (m, 2H), 4.30-4.22 (m, 2H), 3.47-3.38 (m, 2H), 1.34-1.28 (m, 3H) (data for keto form only)

Step 2: Synthesis of ethyl (2E)-2-[(4-chlorophenyl) hydrazono]-3-(2,6-difluorophenyl)-3-oxo-propanoate

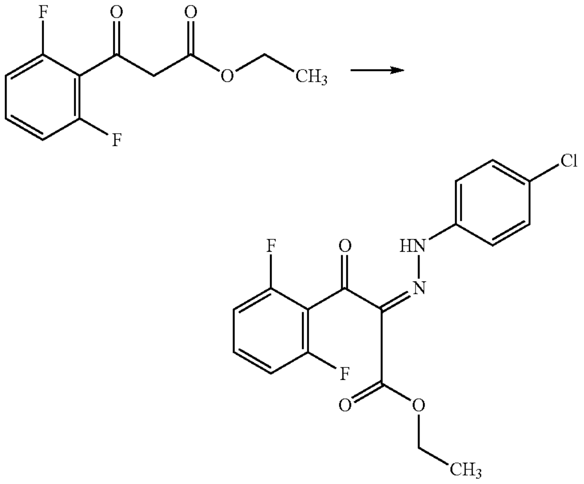

Prepared as for methyl (2E)-3-(2-bromo-6-fluoro-phenyl)-3-oxo-2-[[4-(trifluoromethoxy)phenyl]hydrazono]propanoate (example 1; step 2) using ethyl 3-(2,6-difluorophenyl)-3-oxo-propanoate (3.0 g, 9.2 mmol) and 4-chloroaniline (1.17 g, 9.2 mmol). After a reaction time of 2.75 hours, the solid was collected by filtration to give the desired product as a yellow solid (2.2 g, 5.9 mmol, 64%), $^1$H NMR (400 MHz, $CDCl_3$) δ=13.15-13.05 (m, 1H), 7.44-7.32 (m, 1H), 7.27-7.23 (m, 3H), 7.00-6.91 (m, 3H), 4.49-4.38 (m, 2H), 1.51-1.39 (m, 3H)

Step 3: Synthesis of Ethyl 1-(4-chlorophenyl)-5-fluoro-4-oxo-cinnoline-3-carboxylate

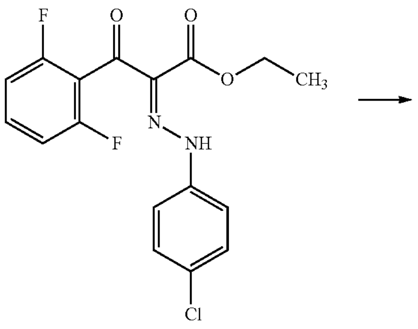

-continued

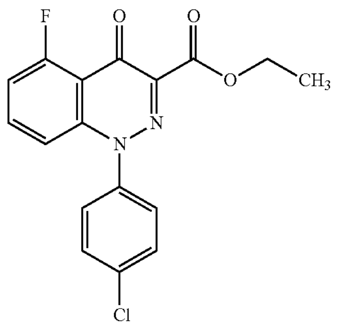

Prepared as for methyl 5-bromo-4-oxo-1-[4-(trifluoromethoxy)phenyl]cinnoline-3-carboxylate (example 1; step 3) using ethyl (2Z)-2-[(4-chlorophenyl)hydrazono]-3-(2,6-difluorophenyl)-3-oxo-propanoate (2.2 g, 5.9 mmol). On completion of reaction, the cooled reaction mixture was poured onto ice and the precipitated solid was collected by filtration to give the desired product as a yellow powder (1.8 g, 5.3 mmol, 89%). $^1$H NMR (400 MHz, $CDCl_3$) δ=7.60-7.52 (m, 3H), 7.48-7.40 (m, 2H), 7.14-7.07 (m, 1H), 7.00-6.87 (m, 1H), 4.51-4.40 (m, 2H), 1.45-1.34 (m, 3H)

Step 4: Synthesis of 1-(4-chlorophenyl)-5-fluoro-4-oxo-cinnoline-3-carboxylic acid

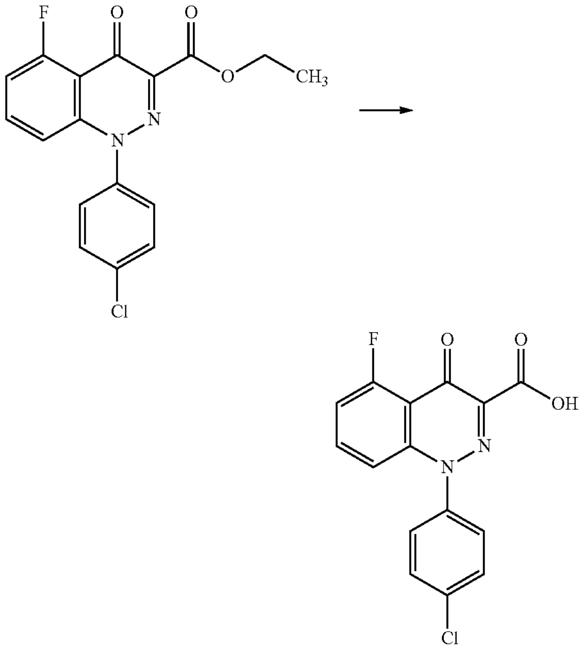

Prepared as for Synthesis of 5-acetyl-4-oxo-1-[4-(trifluoromethoxy)phenyl]cinnoline-3-carboxylic acid (Example 3) using ethyl 1-(4-chlorophenyl)-5-fluoro-4-oxo-cinnoline-3-carboxylate (1.3 g, 3.7 mmol) to give the desired product as an off-white solid (1.15 g, 3.6 mmol, 97%). $^1$H NMR (500 MHz, $CDCl_3$) δ=14.22-13.90 (m, 1H), 7.82-7.74 (m, 1H), 7.63-7.59 (m, 2H), 7.51-7.37 (m, 2H), 7.36-7.26 (m, 1H), 7.19-7.00 (m, 1H)

Step 5: Synthesis of 1-(4-chlorophenyl)-5-(4-fluoro-phenoxy)-4-oxo-cinnoline-3-carboxylic acid

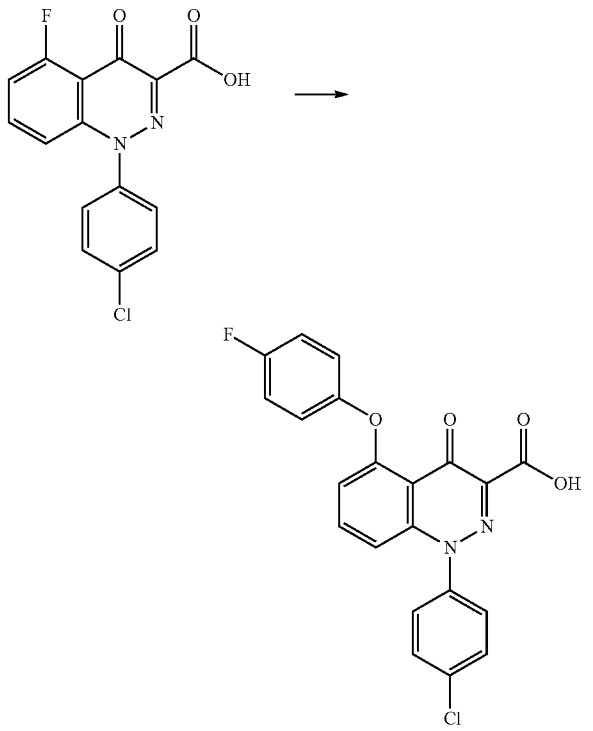

To a solution of 1-(4-chlorophenyl)-5-fluoro-4-oxo-cinnoline-3-carboxylic acid (0.10 g, 0.31 mmol) in dimethylacetamide was added 4-fluorophenol (0.053 g, 0.47 mmol) and potassium carbonate (0.066 g, 0.47 mmol). The reaction mixture was heated at 170° C. for 45 minutes. The cooled reaction mixture was poured onto ice and the precipitated solid was collected by filtration then purified by mass-directed reverse phase HPLC to give the desired product as a white solid (0.010 g, 0,025 mmol, 8%). $^1$H NMR (400 MHz, $CDCl_3$) δ=7.65-7.56 (m, 3H), 7.53-7.44 (m, 2H), 7.20-7.06 (m, 4H), 7.01-6.91 (m, 1H), 6.87-6.72 (m, 1H)

Example 6: Synthesis of Methyl 5-cyano-4-oxo-1-[4-(trifluoromethoxy)phenyl]cinnoline-3-carboxylate and 5-cyano-4-oxo-1-[4-(trifluoromethoxy)phenyl] cinnoline-3-carboxylic acid (Compounds 1.017 and 1.018)

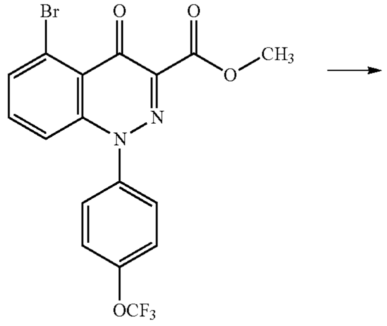

-continued

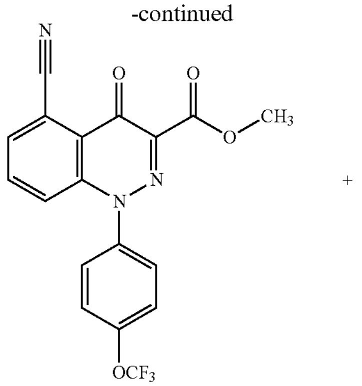

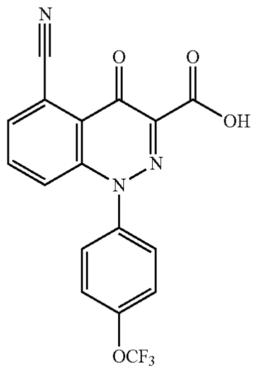

A mixture of methyl 5-bromo-4-oxo-1-[4-(trifluoromethoxy)phenyl]cinnoline-3-carboxylate (0.300 g, 0.677 mmol), dicyanozinc (0.155 g, 1.32 mmol), tetrakis(triphenylphosphine)palladium (0.079 g, 0.0677 mmol), in dimethylformamide (4 mL) was heated under microwave irradiation at 160° C. for 45 minutes. The reaction mixture was diluted with water and extracted twice with ethyl acetate. The combined organics were concentrated to dryness under reduced pressure. The crude residue was purified by mass-directed reverse phase HPLC to give methyl 5-cyano-4-oxo-1-[4-(trifluoromethoxy)phenyl]cinnoline-3-carboxylate (0.088 g, 0.225 mmol, 33%). $^1$H NMR (400 MHz, chloroform) δ=7.93-7.86 (m, 1H), 7.77-7.70 (m, 1H), 7.61-7.55 (m, 2H), 7.50-7.41 (m, 3H), 4.03-3.91 (m, 3H)

Also obtained was 5-cyano-4-oxo-1-[4-(trifluoromethoxy)phenyl]cinnoline-3-carboxylic acid (0.016 g, 0.044 mmol, 6%). $^1$H NMR (400 MHz, chloroform) δ=8.11-8.04 (m, 1H), 7.97-7.84 (m, 1H), 7.65-7.58 (m, 3H), 7.54-7.39 (m, 3H)

Example 7: Synthesis of methyl 5-(4-fluorophenyl)-4-oxo-1-[4-(trifluoromethoxy)phenyl]cinnoline-3-carboxylate (Compound P6)

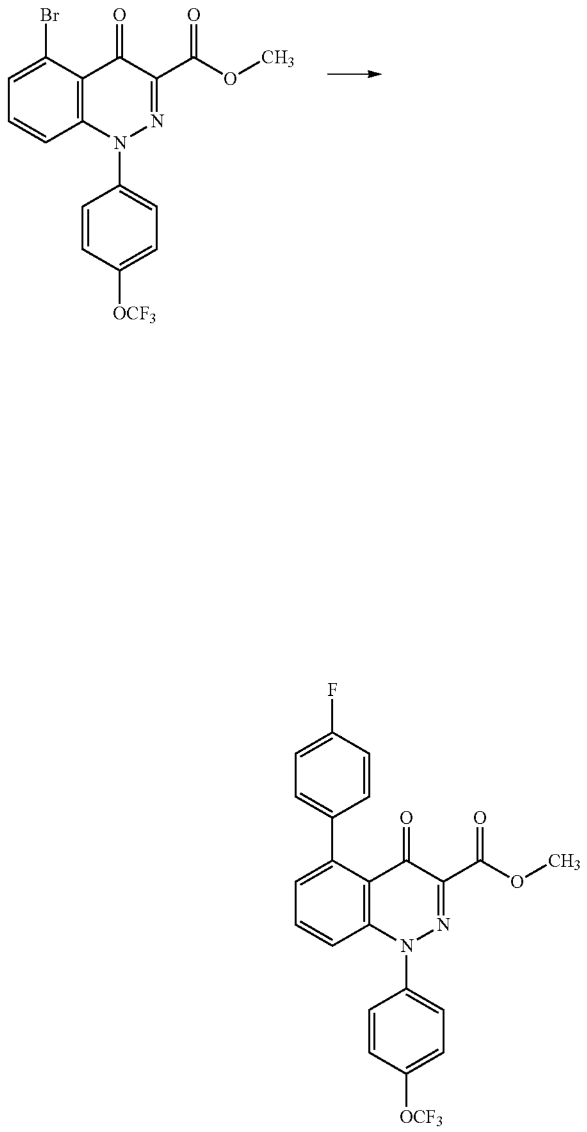

A mixture of methyl 5-bromo-4-oxo-1-[4-(trifluoromethoxy)phenyl]cinnoline-3-carboxylate (0.200 g, 0.451 mmol), (4-fluorophenyl)boronic acid (0.095 g, 0.677 mmol), potassium carbonate (0.126 g, 0.903 mmol) in acetonitrile (1.00 mL) and water (0.200 mL) was heated under microwave irradiation at 100° C. for 30 minutes. The reaction mixture was diluted with 2M aqueous hydrochloric acid and extracted into ethyl acetate (three times). The combined Gorgonio extracts were evaporated to dryness under reduced pressure. The crude residue was purified by flash chromatography on silica gel using a gradient of 5-100% ethyl acetate in cyclohexane as eluent to give the desired product as an off-white solid (0.075 g, 0.164 mmol, 36%). $^{1}$H NMR (400 MHz, chloroform) δ=7.63-7.56 (m, 3H), 7.50-7.45 (m, 2H), 7.31-7.27 (m, 3H), 7.20-7.15 (m, 1H), 7.13-7.06 (m, 2H), 3.93-3.80 (m, 3H)

Example 8: Synthesis of ethyl 5-[(E)-N-hydroxy-C-methyl-carbonimidoyl]-4-oxo-1-[4-(trifluoromethoxy)phenyl]cinnoline-3-carboxylate (Compound P14) and 5-[(E)-N-hydroxy- C-methyl-carbonimidoyl]-4-oxo-1-[4-(trifluoromethoxy) phenyl]cinnoline-3-carboxylic acid (Compound P15)

Step 1

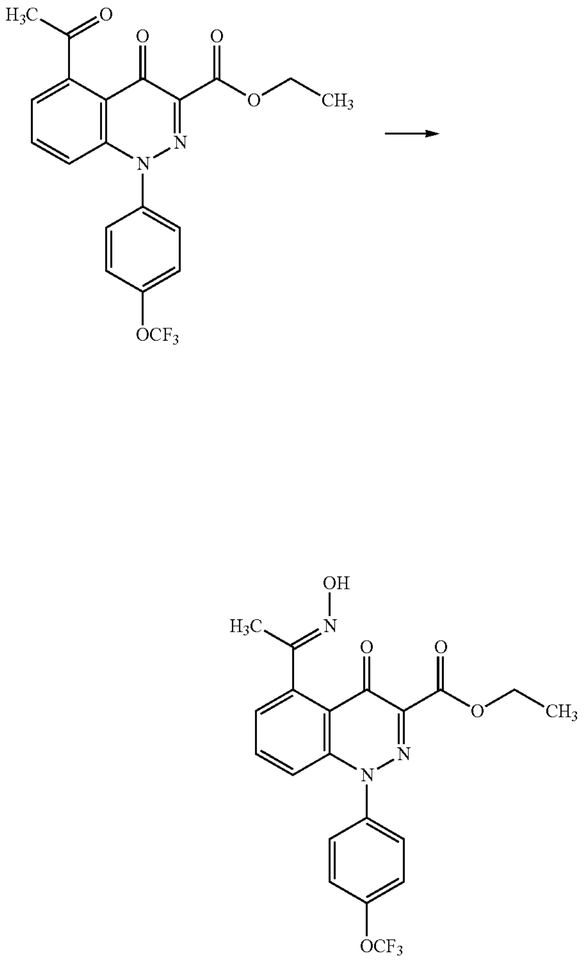 [SMILES: CCOC(=O)c1nn(-c2ccc(OC(F)(F)F)cc2)c2cccc(C(C)=O)c2c1=O ; CCOC(=O)c1nn(-c2ccc(OC(F)(F)F)cc2)c2cccc(/C(C)=N/O)c2c1=O]

To a stirring solution of ethyl 5-acetyl-4-oxo-1-[4-(trifluoromethoxy)phenyl]cinnoline-3-carboxylate (50.0 mg, 0.119 mmol) in methanol (10 mL) and water (2.5 mL) at 0° C. was added sodium acetate (0,088 g, 1.07 mmol) and hydroxylamine chloride (0074 g, 1.07 mmol). The reaction mixture was stirred for 5 minutes then heated at 80° C. for 6 hours. The cooled reaction mixture was poured onto ice water, neutralized with 2M aqueous hydrochloric acid and filtered. The filtrate was evaporated to dryness under reduced pressure. The crude residue was purified by flash chromatography on silica gel using a gradient of 0-10% methanol in dichloromethane as eluent to give desired product as an off-white solid (0.16 g, 0.37 mmol, 34%), $^{1}$H NMR (400 MHz, DMSO-$d_6$): 10.89 (s, 1H), 7.85 (d, 2H), 7.72 (d, 3H), 7.30 (d, 1H), 7.17 (d, 1H), 4.32 (m, 2H), 2.04 (s, 3H), 1.28 (t, 3H)

Step 2

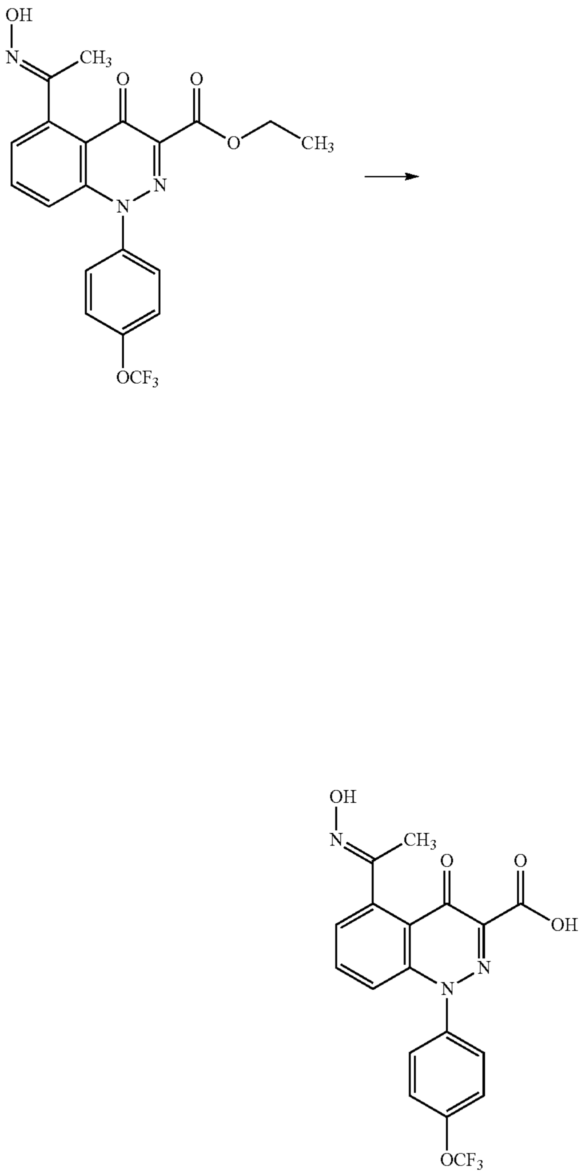

To a stirring solution of ethyl 5-[(E)-N-hydroxy-C-methyl-carbonimidoyl]-4-oxo-1-[4-(trifluoromethoxy)phenyl]cinnoline-3-carboxylate (150 mg, 0.33 mmol) in tetrahydrofuran (6 mL) and water (2 mL) at room temperature was added lithium hydroxide monohydrate (0.055 g, 1.31 mmol). The reaction mixture was stirred at room temperature for 16 hours. The reaction mixture was acidified by addition of 2M aqueous hydrochloride acid (5 mL) and extracted into dichloromethane (x2). The combined organic extracts were washed with brine, dried over sodium sulfate and evaporated to dryness under reduced pressure to give 5-[(E)-N-hydroxy-C-methyl-carbonimidoyl]-4-oxo-1-[4-(trifluoromethoxy)phenyl]cinnoline-3-carboxylic acid (0.098 g, 0.24 mmol, 74%) as pale brown solid. $^1H$ NMR (400 MHz, DMSO-$d_6$): 13.9 (brs, 1H), 10.97 (s, 1H), 7.87 (m, 3H), 7.72 (d, 2H), 7.38 (d, 1H), 7.21 (d, 1H), 2.07 (s, 3H)

Example 9: Synthesis of ethyl 5-[5-(difluoromethyl)isoxazol-3-yl]-4-oxo-1-[4-(trifluoromethoxy)phenyl]cinnoline-3-carboxylate (Compound P12) and 5-[5-(difluoromethyl)isoxazol-3-yl]-4-oxo-1-[4-(trifluoromethoxy)phenyl]cinnoline-3-carboxylic acid (Compound P13)

Step 1

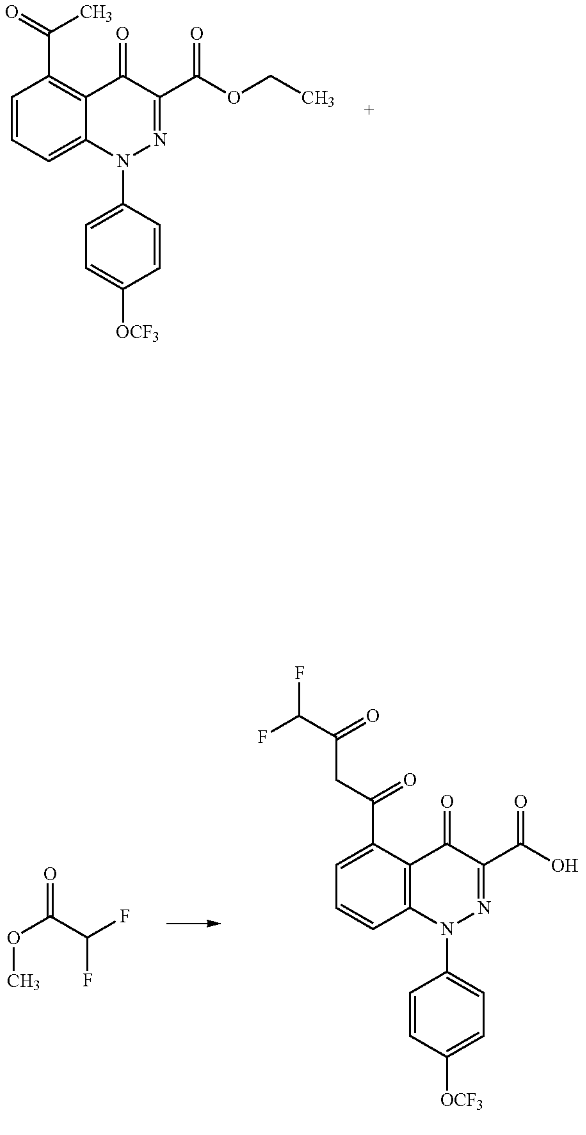

To a stirring solution of ethyl 5-acetyl-4-oxo-1-[4-(trifluoromethoxy)phenyl]cinnoline-3-carboxylate (1.00 g, 2.38 mmol) in tetrahydrofuran (25 mL) was added a solution of sodium methoxide (0.129 g, 2.38 mmol) and methyl 2,2-difluoroacetate (0.393 g, 3.57 mmol) in methanol. The reaction mixture was stirred at room temperature for 10 hours. The reaction mixture was quenched by addition of 1M aqueous hydrochloric acid and extracted into ethyl acetate. The organic extracts were evaporated to dryness under reduced pressure to give crude product (0.900 g, 1.91 mmol, 80%) as a brown solid.

Step 2

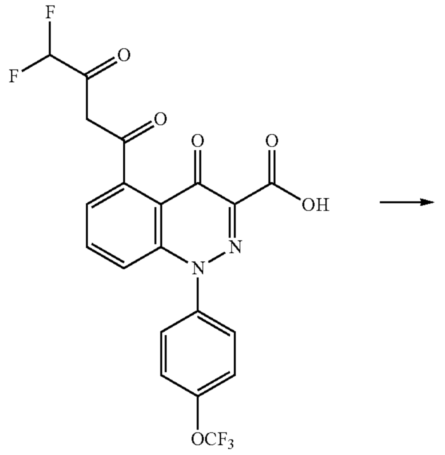

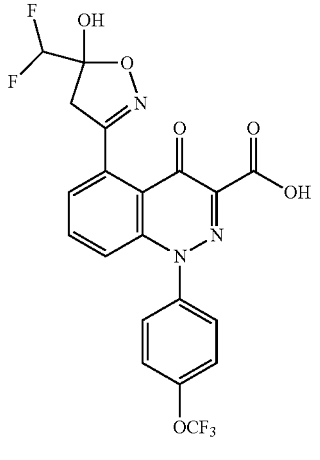

To a stirring solution of 5-(4,4-difluoro-3-oxo-butanoyl)-4-oxo-1-[4-(trifluoromethoxy)phenyl]cinnoline-3-carboxylic acid (0.650 q, 1.38 mmol) in ethanol (5.30 mL) was added 1M aqueous sodium hydroxide solution (075 mL) followed by hydroxylamine hydrochloride (0.144 g, 2.07 mmol). The reaction mixture was stirred at room temperature 2 hours. The reaction mixture was diluted with brine, extracted into ethyl acetate and the combined organic extracts were evaporated to dryness under reduced pressure to give 5-[5-(difluoromethyl)-5-hydroxy-4H-isoxazol-3-yl]-4-oxo-1-[4-(trifluoromethoxy)phenyl]cinnoline-3-carboxylic acid (0.800 g, 1.24 mmol, 90%).

Step 3

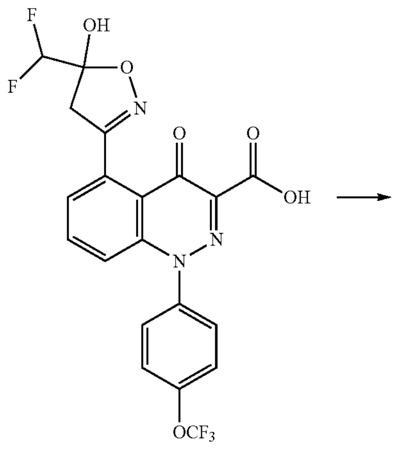

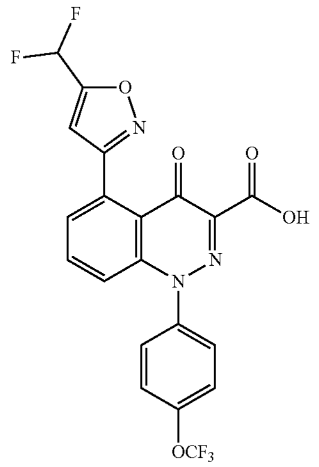

To a stirring solution of 5-[5-(difluoromethyl)-5-hydroxy-4H-isoxazol-3-yl]-4-oxo-1-[4-(trifluoromethoxy)phenyl]cinnoline-3-carboxylic acid (0.600 g, 1.11 mmol) in toluene (10 mL) was added sodium p-toluenesulfonate (0.019 g, 0.11 mmol). The reaction mixture was stirred at 110'1 for 3 hours. The reaction mixture was evaporated to dryness under reduced pressure and the residue was partitioned between water and ethyl acetate. The organic extract was washed with brine and evaporated to dryness under reduced pressure. The crude residue was purified by flash chromatography on silica gel using a gradient of 40-50% ethyl acetate in hexanes to give 5-[5-(difluoromethyl)isoxazol-3-yl]-4-oxo-1-[4-(trifluoromethoxy)phenyl]cinnoline-3-carboxylic acid (0.110 g, 0,235 mmol, 21%). $^1$H NMR (400 MHz, DMSO-$d_6$): 13.78 (s, 1H), 7.91 (m, 3H), 7.77 (m, 3H), 7.75 (m, 2H), 7.05 (d, 1H)

Step 4

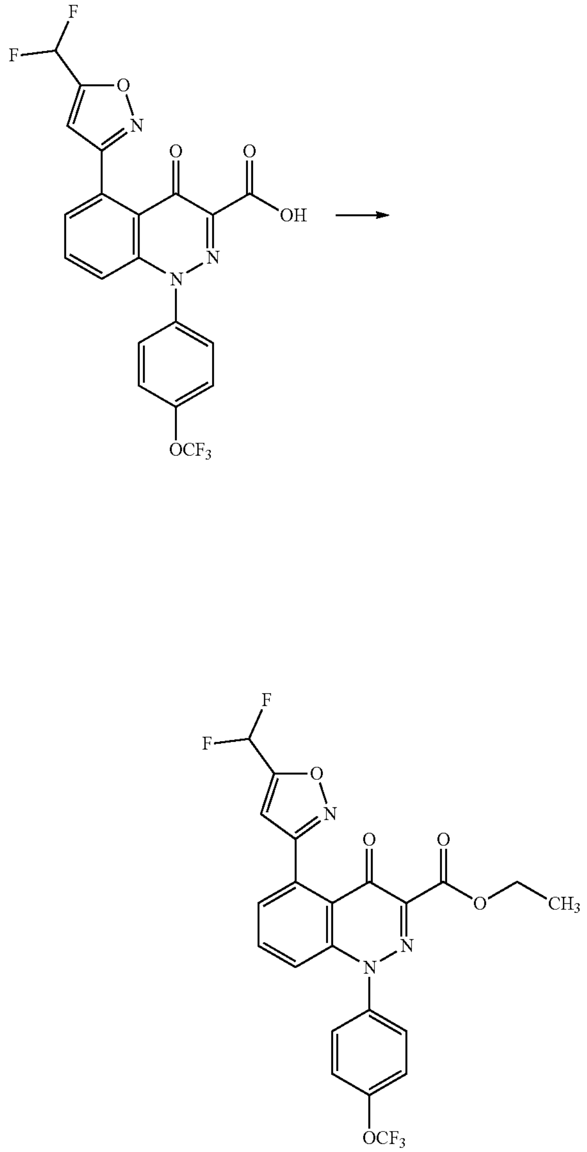

To a stirring solution of 5-[5-(difluoromethyl)isoxazol-3-yl]-4-oxo-1-[4-(trifluoromethoxy)phenyl]cinnoline-3-carboxylic acid (0.250 g, 0.535 mmol) in ethanol (25 mL) and at room temperature was added concentrated sulfuric acid (0.105 g, 1.07 mmol). The reaction mixture was heated with stirring at 75° C. for 6 hours. The reaction mixture was evaporated to dryness under reduced pressure. The crude residue was diluted with cold water, neutralized with saturated aqueous sodium hydrogen carbonate solution, and extracted into ethyl acetate. The combined organic extracts were washed with brine, dried over sodium sulfate, filtered and evaporated to dryness under reduced pressure to give ethyl 5-[5-(difluoromethyl)isoxazol-3-yl]-4-oxo-1-[4-(trifluoromethoxy)phenyl]cinnoline-3- carboxylate (0.120 g, 0.237 mmol, 44%) as brown semi solid. $^1$H NMR (400 MHz, DMSO-$d_6$): 7.86 (s, 1H), 7.71 (d, 2H), 7.61 (m, 3H), 7.41 (m, 2H), 7.03 (s, 1H), 4.29 (t, 2H), 1.29 (q, 3H)

Example 10: synthesis of ethyl 4-oxo-1-[4-(trifluoromethoxy)phenyl]-5-vinyl-cinnoline-3-carboxylate (Compound P16) and 4-oxo-1-[4-(trifluoromethoxy) phenyl]-5-vinyl-cinnoline-3-carboxylic acid (Compound P17)

Step 1

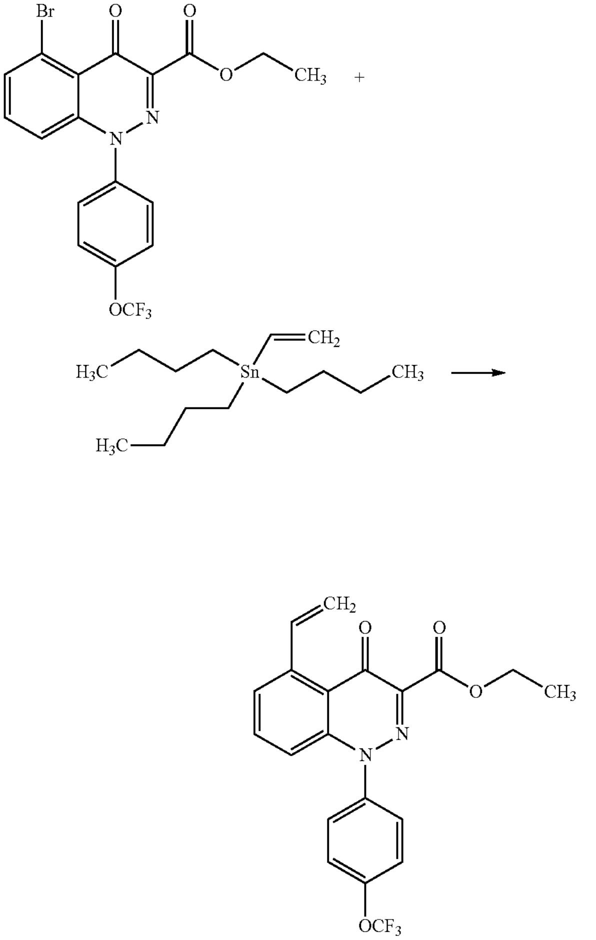

To a stirring solution of ethyl 5-bromo-4-oxo-1-[4-(trifluoromethoxy)phenyl]cinnoline-3-carboxylate (1.80 g, 3.94 frump in toluene (30 mL) at room temperature was added tributyl(vinyl)tin (1.87 g, 5.91 mmol). The mixture was purged with argon for 5 minutes before addition of bis (triphenylphosphine)palladium (II) chloride (0.287 g, 0.394 mmol) and again purged with argon for 5 minutes. The reaction mixture was heated at 110° C. for 4 hours in sealed tube. The cooled reaction mixture was filtered through a pad of diatomaceous earth and the filtrate was evaporated to dryness under reduced pressure. The crude residue was purified by flash chromatography on silica gel using 10% ethyl acetate in hexanes as eluent to give ethyl 4-oxo-1-[4-(trifluoromethoxy)phenyl]-5-vinyl-cinnoline-3-carboxylate (1.30 g, 3.05 mmol, 78%) as an off-white solid. $^1$H NMR (400 MHz, $CDCl_3$): 8.14 (m, 1H), 7.56 (m, 3H), 7.53 (d, 3H), 7.08 (d, 1H), 5.65 (d, 1H), 5.47 (d, 1H), 4.47 (q, 2H), 1.42 (f, 3H)

Step 2

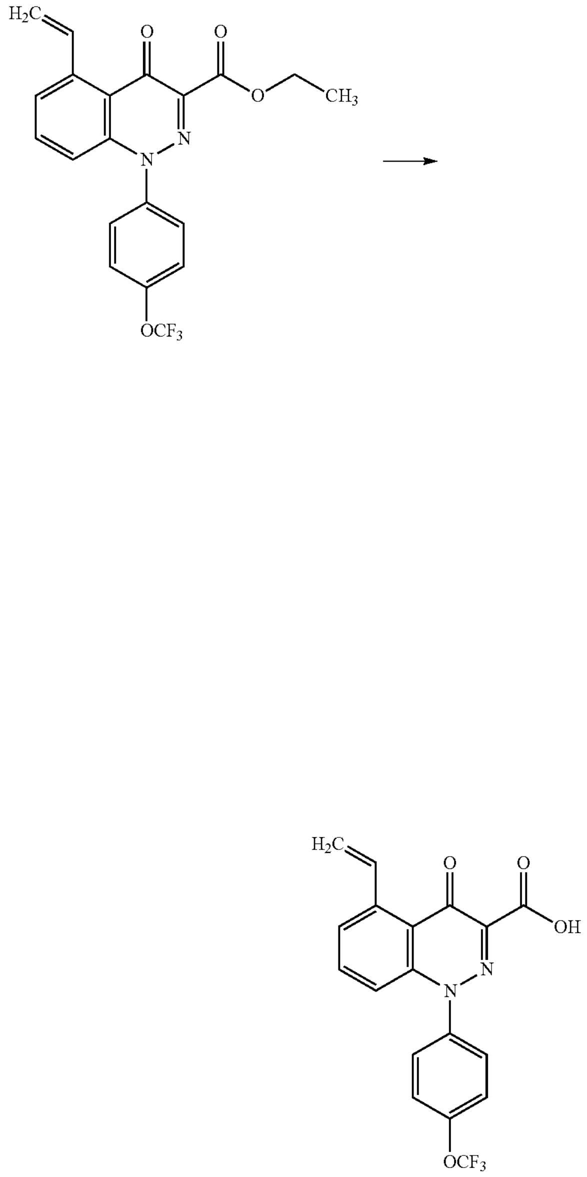

To a stirring solution of ethyl 4-oxo-1-[4-(trifluoromethoxy)phenyl]-5-vinyl-cinnoline-3-carboxylate (150 mg, 0,352 mmol) in a mixture of tetrahydrofuran (3 mL) and water (2 mL) at room temperature was added lithium hydroxide monohydrate (0.059 g, 1.41 mmol). The reaction mixture was stirred at room temperature for 16 hours. The reaction mixture was acidified by addition of 2M aqueous hydrochloric acid and extracted into dichloromethane. The combined organic extracts were washed with brine, dried over sodium sulfate, filtered and evaporated to dryness under reduced pressure to give 4-oxo-1-[4-(trifluoromethoxy)phenyl]-5-vinyl-cinnoline-3-carboxylic acid (0.098 g, 0.247 mmol, 70%) as an off-white solid. $^1H$ NMR (400 MHz, DMSO-$d_6$): 14.08 (s, 1H), 8.04 (m, 1H), 7.79 (m, 2H), 7.72 (m, 1H), 7.64 (m, 2H), 7.55 (m, 1H), 7.18 (d, 1H), 5.79 (d, 1H), 5.74 (d, 1H)

Example 11: Synthesis of ethyl 4-oxo-5-(2-oxoethyl)-1-[4-(trifluoromethoxy)phenyl]cinnoline-3-carboxylate (Compound P18)

Step 1

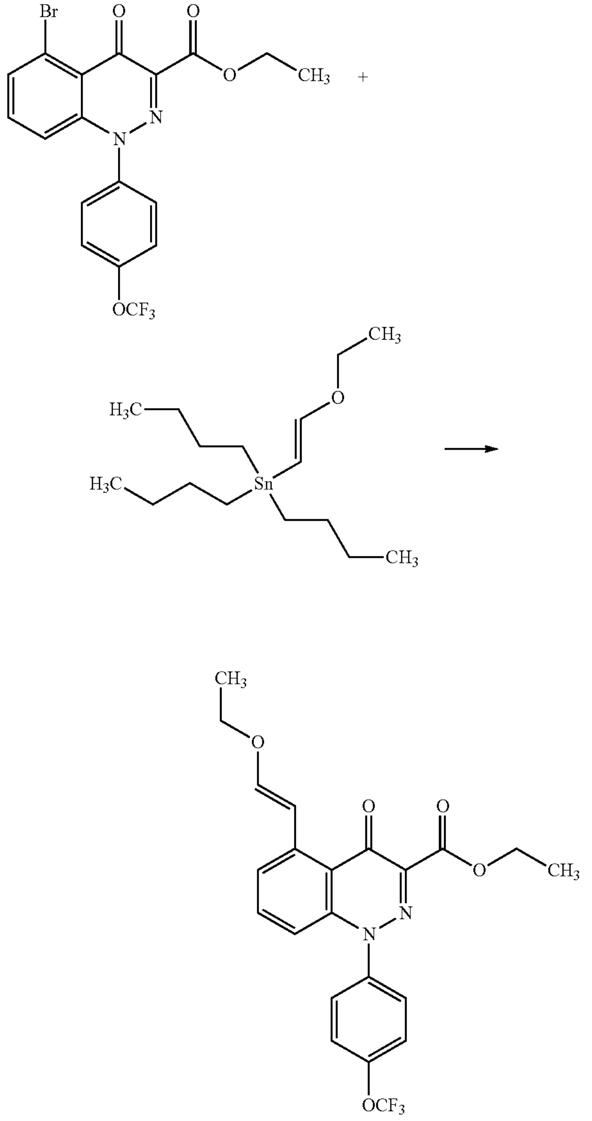

To a stirring solution of ethyl 5-bromo-4-oxo-1-[4-(trifluoromethoxy)phenyl]cinnoline-3-carboxylate (0.200 g, 0,394 mmol) in toluene (4 mL) was added bis(triphenylphosphine)palladium (II) chloride (0.0287 g, 0.0394 mmol). The mixture was degassed under argon for 5 minutes before addition of tributyl(1-ethoxyvinyl)stannane (0,178 mL, 0.492 mmol). The reaction mixture was heated at 110° C. for 3 hours. The cooled reaction mixture was filtered through a pad of diatomaceous earth and the filtrate was evaporated to dryness under reduced pressure. The crude residue was purified by flash chromatography on silica gel using 20% ethyl acetate in hexanes as eluent to give ethyl 5-[(E)-2-ethoxyvinyl]-4-oxo-1-[4-(trifluoromethoxy)phenyl]cinnoline-3-carboxylate (0.080 g, 0.178 mmol, 45%).

Step 2

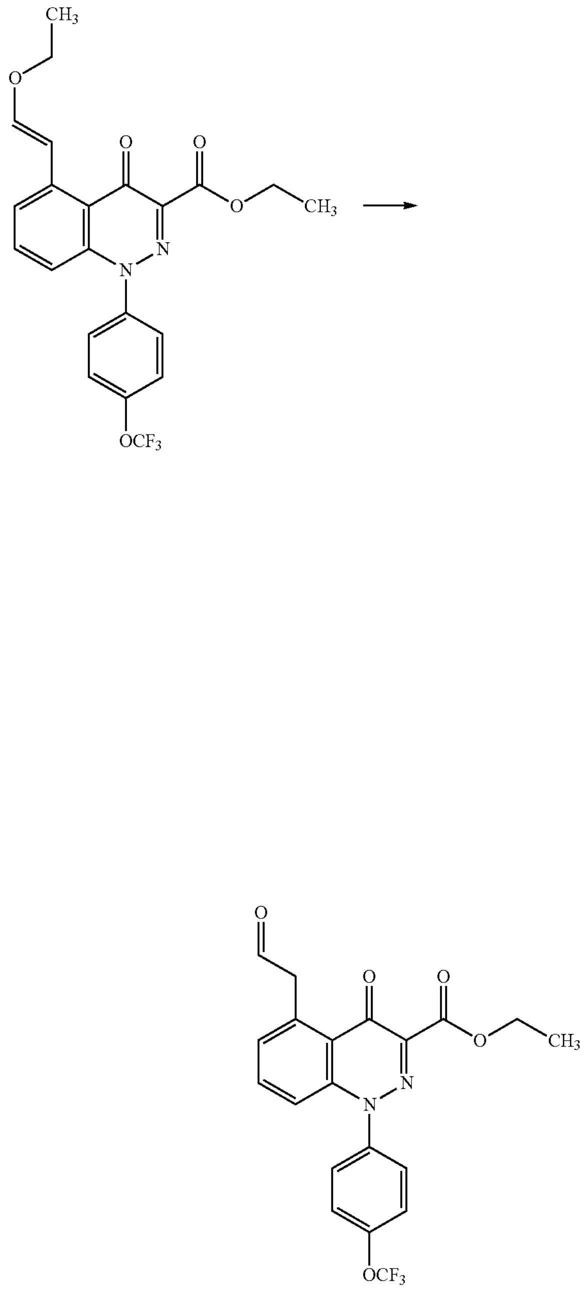

To a stirring solution of ethyl 5-[(E)-2-ethoxyvinyl]-4-oxo-1-[4-(trifluoromethoxy)phenyl]cinnoline-3-carboxylate (50%, 2.00 g, 2.23 mmol) in acetone (10 mL) was added 2M aqueous hydrochloric acid (5.00 g). The reaction mixture was stirred for 5 minutes then heated to 65° C. for 16 hours. The cooled reaction mixture was evaporated to dryness under reduced pressure. The crude residue was purified by flash chromatography on silica gel using 3% methanol in dichloromethane as eluent to give ethyl 4-oxo-5-(2-oxoethyl)-1-[4-(trifluoromethoxy)phenyl]cinnoline-3-carboxylate (0.200 g, 0.466 mmol, 21%) as a brown solid. $^1$H NMR (400 MHz, DMSO-$d_8$): 9.76 (s, 1H), 7.87 (t, 2H), 7.74 (m, 3H), 7.38 (d, 1H), 7.12 (d, 1H), 430 (m, 4H), 1.29 (m, 3H)

Example 12: Synthesis of ethyl 5-(4-chloropyrazol-1-oxo-4-oxo-1-[4-(trifluoromethoxy)phenyl]cinnoline-3-carboxylate (Compound P32) and 5-(4-Chloropyrazol-1-yl)-4-oxo-1-[4-(trifluoromethoxy)phenyl]cinnoline-3-carboxylic acid (Compound P19)

Step 1

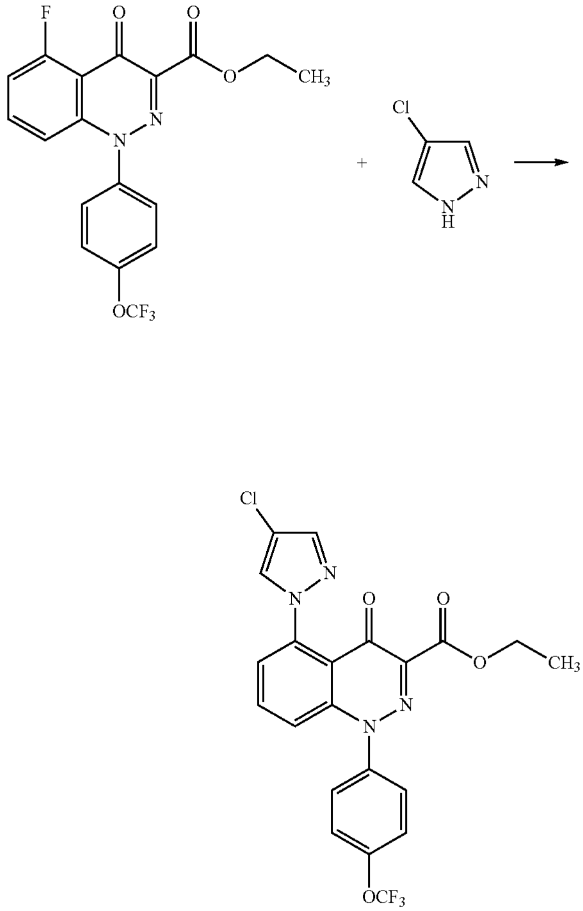

To a solution of ethyl 5-fluoro-4-oxo-1-[4-(trifluoromethoxy)phenyl]cinnoline-3-carboxylate (0.500 g, 1.26 mmol) in N,N-dimethylformamide (5 mL) at 0° C. and under argon was added potassium carbonate (124 mg, 1.26 mmol) followed by 4-chloro-1H-pyrazole (0.194 g, 1.89 mmol). The reaction mixture was stirred at 110° C. for 5 hours. The cooled reaction mixture was poured into water and extracted into ethyl acetate. The combined organic extracts were washed with water then brine, dried over sodium sulfate, filtered, and evaporated to dryness under reduced pressure. The crude residue was purified by flash chromatography on silica gel using a gradient of 0-50% ethyl acetate in hexanes as eluent to give ethyl 5-(4-chloropyrazol-1-yl)-4-oxo-1-[4-(trifluoromethoxy)phenyl]cinnoline-3-carboxylate (450 mg, 0.921 mmol, 73%) as pale brown solid. $^1$H NMR (400 MHz, DMSO-$d_6$): 8.21 (s, 1H), 7.37 (m, 4H), 7.32 (d, 2H), 7.56 (d, 1H), 7.28 (m, 1H), 4.29 (d, 2H), 1.27 (t, 3H)

Step 2

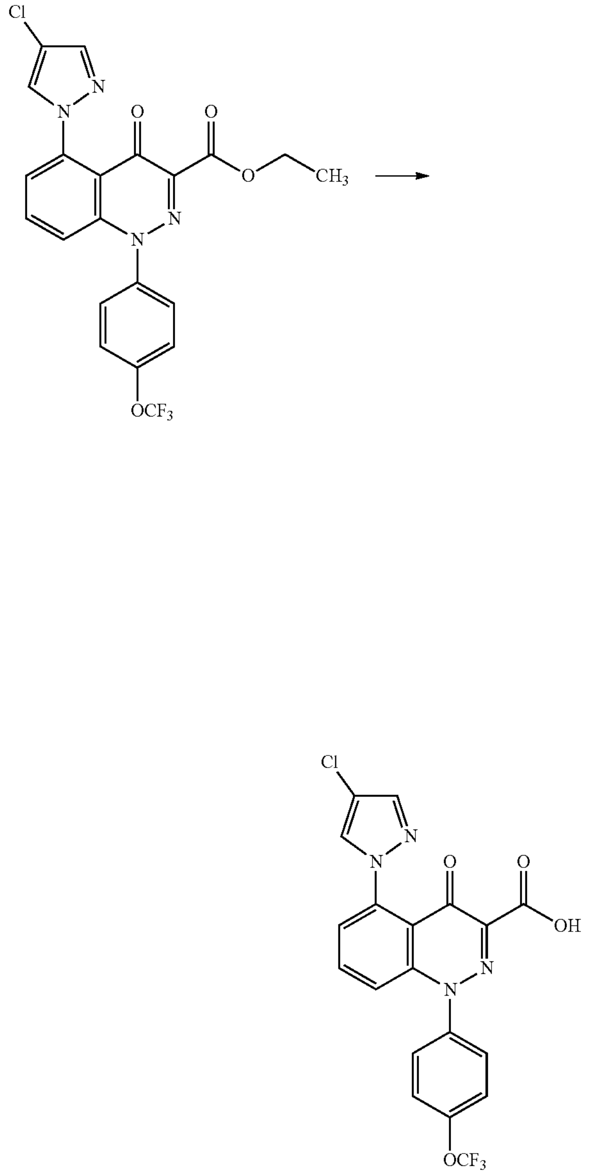

To a stirring solution of ethyl 5-(4-chloro-2H-pyrrol-2-yl)-4-oxo-1-[4-(trifluoromethoxy)phenyl]cinnoline-3-carboxylate (180 mg, 0.358 mmol) in a mixture of tetrahydrofuran (5 mL) and water (1.5 mL) at room temperature was added lithium hydroxide monohydrate (0.060 g, 1.43 mmol). The reaction mixture was stirred at room temperature for 2 hours. The reaction mixture was acidified with 2M aqueous hydrochloric acid (2 mL) and extracted into dichloromethane. The combined organic extracts were washed with brine, dried over sodium sulfate, filtered and evaporated to dryness under reduced pressure to give 5-(4-chloropyrazol-1-yl)-4-oxo-1-[4-(trifluoromethoxy)phenyl]cinnoline-3-carboxylic acid; (0.110 g, 0.245 mmol, 68%) as yellow sold. $^1$H NMR (400 MHz, DMSO-$d_6$): 13.81 (t, 11-1), 8.24 (s, 1H), 7.91 (m, 4H), 7.72 (m, 2H), 7.62 (d, 1H), 7.36 (d, 1H)

Example 13: Synthesis of ethyl 5-(cyanomethyl)-4-oxo-1-[4-(trifluoromethoxy)phenyl]cinnoline-3-carboxylate (Compound P35)

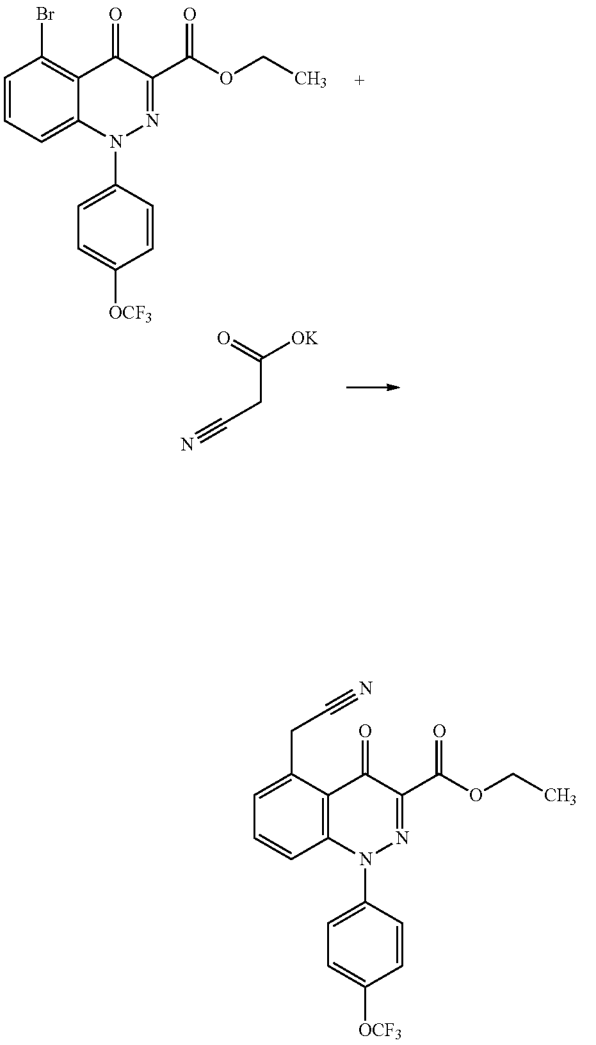

A stirring solution of ethyl 5-bromo-4-oxo-1-[4-(trifluoromethoxy)phenyl]cinnoline-3-carboxylate (0.100 g, 0.197 mmol) in mesitylene (10 mL) was degassed with argon for 5 minutes before sequential addition of (2-cyanoacetyl) oxypotassium (0.082 mL, 0.295 mmol), allyl palladium(ii) chloride dimer (0.0144 g, 0.0394 mmol) and 2-dicyclohexylphosphino-2',6'-dimethoxybiphenyl (0.0484 g, 0.118 mmol). The reaction mixture was degassed under argon for 2 minutes then heated at 100° C. for 5 hours in a sealed tube. The cooled reaction mixture was filtered through diatomaceous earth and the filtrate was evaporated to dryness under reduced pressure. The crude residue was purified by flash chromatography on silica gel using a gradient of 20-30% ethyl acetate in hexanes as eluent to give ethyl 5-(cyanomethyl)-4-oxo-1-[4-(trifluoromethoxy)phenyl]cinnoline-3-carboxylate (0.050 g, 0.120 mmol, 61%). $^1$H NMR (400 MHz, DMSO-$d_6$): 7.86 (d, 2H), 7.79 (m, 1H), 7.74 (d, 2H), 7.65 (d, 1H), 7.29 (d, 1H), 4.59 (5, 2H), 4.35 (q, 2H), 1.30 (t, 3H)

Example 14: Synthesis of ethyl 5-(difluoromethyl)-4-oxo-1-[4-(trifluoromethoxy)phenyl]cinnoline-3-carboxylate (Compound P36)

Step 1

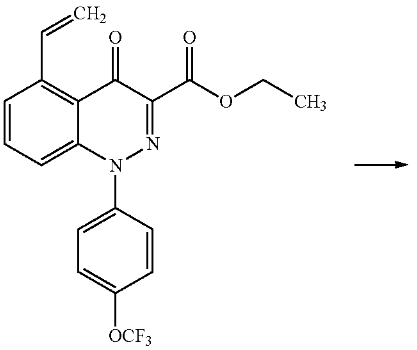

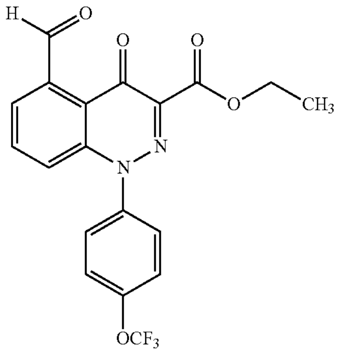

To a stirring solution of ethyl 4-oxo-1-[4-(trifluoromethoxy)phenyl]-5-vinyl-cinnoline-3-carboxylate (0.600 g, 1.41 mmol) in a mixture of tetrahydrofuran (20 mL) and water (5 mL) at 0° C. was added sodium periodate (0,905 g, 4.23 mmol) and potassium osmate dihydrate (0.052 g, 0.141 mmol). The reaction mixture stirred at room temperature for 16 hours. The reaction mixture was quenched by addition of 10% aqueous sodium thiosulfate solution and extracted into ethyl acetate. The combined organic extracts were washed with brine, dried over sodium sulfate, filtered, and evaporated to dryness under reduced pressure. The crude residue was purified by flash chromatography on silica gel using 30% ethyl acetate in hexanes as eluent to give ethyl 5-formyl-4-oxo-1-[4-(trifluoromethoxy)phenyl]cinnoline-3-carboxylate (0.455 g, 1.06 mmol, 76%) as an off-white solid.

Step 2

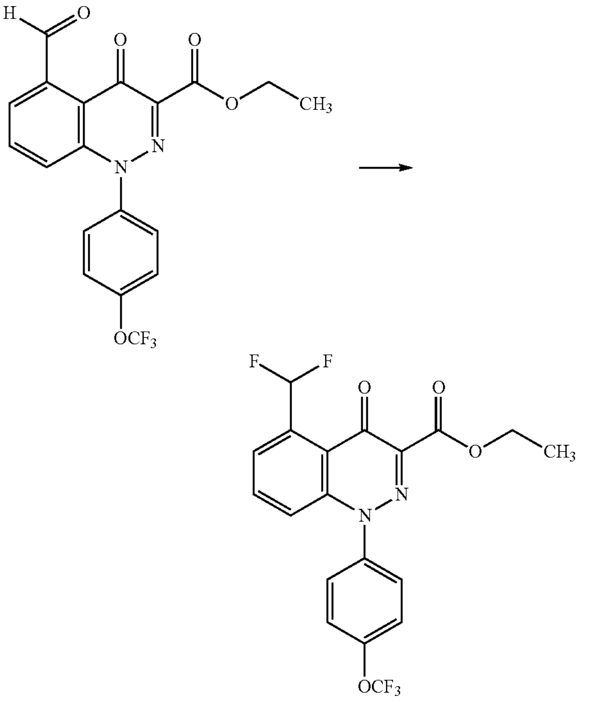

To a stirring solution of ethyl 5-formyl-4-oxo-1-[4-(trifluoromethoxy)phenyl]cinnoline-3-carboxylate (300 mg, 0.70 mmol) in dichloromethane (20 mL) at 0° C. was added diethylaminosulfur trifluoride (0.565 g, 3.51 mmol). The reaction mixture was stirred at room temperature for 16 hours. The reaction mixture was quenched by addition of saturated aqueous sodium hydrogen carbonate solution and extracted into dichloromethane. The combined organic extracts were washed with brine, dried over sodium sulfate, filtered, and evaporated to dryness under reduced pressure. The crude residue was purified by flash chromatography on silica gel using 20% ethyl acetate in hexanes as eluent to give ethyl 5-(difluoromethyl)-4-oxo-1-[4-(trifluoromethoxy)phenyl]cinnoline-3-carboxylate (0.290 g, 0.64 mmol, 92%) as a white solid. $^1$H NMR (400 MHz, $CDCl_3$): 8.22 (s, 2H), 7.93 (t, 1H), 7.73 (t, 2H), 7.45 (d, 2H), 7.32 (s, 1H), 4.45 (q, 2H), 1.41 (f, 3H)

Example 15: Synthesis of ethyl 5-nitro-4-oxo-1-[4-(trifluoromethoxy)phenyl]cinnoline-3-carboxylate (Compound P39) and 5-nitro-4-oxo-1-[4-(trifluoromethoxy)phenyl]cinnoline-3-carboxylic acid (Compound P40)

Step 1

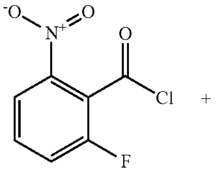

-continued

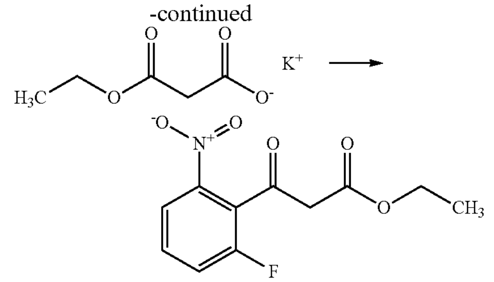

To a stirring solution of ethyl potassium malonate (8.36 g, 49.1 mmol) in acetonitrile (150 mL) at room temperature was added sequentially 2-fluoro-6-nitro-benzoyl chloride (5.00 g, 24.6 mmol), magnesium dichloride (5.85 g, 61.4 mmol) and triethylamine (5.47 g, 54.0 mmol). The reaction mixture was stirred at room temperature for 16 hours. The residue was suspended in ethyl acetate and 2M aqueous hydrochloric acid. The phases were separated and the aqueous phase was extracted into ethyl acetate (x2). The combined organic extracts were dried over sodium sulfate, filtered, and evaporated to dryness under reduced pressure to give the crude product as a pale yellow liquid.

Step 2

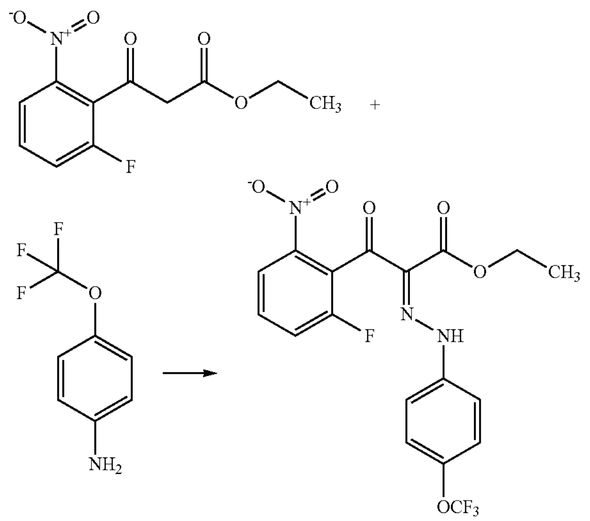

To a stirring solution of 4-(trifluoromethoxy)aniline (3.50 g, 19.8 mmol) in 2M aqueous hydrochloric acid (10 mL) at 0° C. was added dropwise a solution of sodium nitrite (1.49 g, 21.6 mmol) in water (5 mL). The reaction mixture was stirred for 0.5 hours before being added dropwise to a cooled (0° C.) solution of ethyl 3-(2-fluoro-6-nitro-phenyl)-3-oxo-propanoate (5.10 g, 18.0 mmol and potassium acetate (8.81 g, 89.9 mmol) in water (50 mL). The reaction mixture was stirred at 0° C. for 2 hours then allowed to warm to room temperature. The reaction mixture was diluted with water and extracted into ethyl acetate (x2). The combined organic extracts were washed with water and brine, dried over sodium sulfate, filtered and evaporated to dryness under reduced pressure to give crude ethyl (2Z)-3-(2-fluoro-6-nitro-phenyl)-3-oxo-2-[[4-(trifluoromethoxy)phenyl]hydrazono]propanoate (5.00 g, 11.3 mmol, 63%) as a red liquid.

Step 3

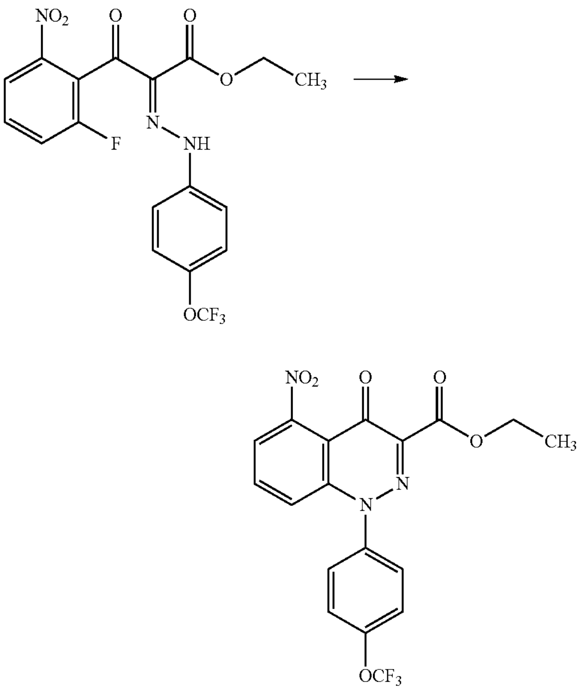 [SMILES: CCOC(=O)/C(=N\Nc1ccc(OC(F)(F)F)cc1)C(=O)c1c(F)cccc1[N+](=O)[O-] ; CCOC(=O)c1nn(-c2ccc(OC(F)(F)F)cc2)c2cccc([N+](=O)[O-])c2c1=O]

To a stirring solution of ethyl (2Z)-3-(2-fluoro-6-nitro-phenyl)-3-oxo-2-[[4-(trifluoromethoxy)phenyl]hydrazono] propanoate (8.00 g, 16.2 mmol) in N,N- dimethylformamide (80 mL) was added potassium carbonate (4.42 g, 32.5 mmol). The reaction mixture was heated at 100° C. for 4 hours. The cooled reaction mixture was diluted with cold water and extracted into ethyl acetate (x2). The combined organic extracts were dried over sodium sulfate, filtered, and evaporated to dryness under reduced pressure. The crude residue was purified by flash chromatography on silica gel using 20% ethyl acetate in hexanes as eluent to give ethyl 5-nitro-4-oxo-1-[4-(trifluoromethoxy)phenyl]cinnoline-3-carboxylate (7.00 g, 15.9 mmol, 98%) as a pale orange solid. $^1$H NMR (400 MHz, DMSO-$d_6$): 7.95 (m, 4H), 7.75 (d, 2H), 7.36 (m, 1H), 4.39 (q, 2H), 1.23 (t, 3H)

Step 4

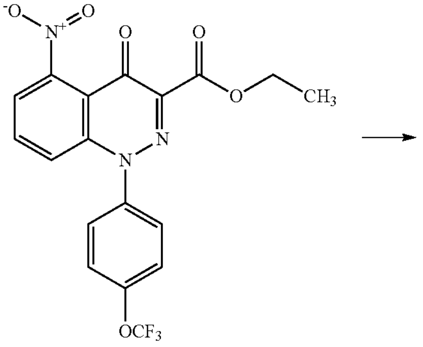

-continued

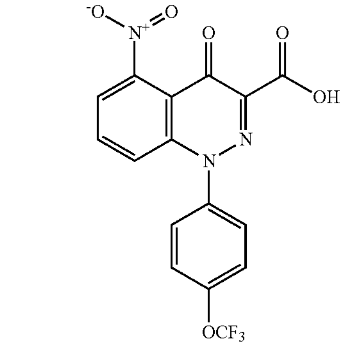

To a stirring solution of ethyl 5-nitro-4-oxo-1-[4-(trifluoromethoxy)phenyl]cinnoline-3-carboxylate (0.200 g, 0.449 mmol) in a mixture of tetrahydrofuran (10 mL) and water (5 mL) at room temperature was added lithium hydroxide monohydrate (0.075 g, 1.80 mmol). The reaction mixture was stirred at room temperature for 16 hours. The reaction mixture was acidified with 2M aqueous hydrochloric acid and extracted into dichloromethane (x2). The combined organic extracts were washed with brine, dried over sodium sulfate, filtered and evaporated to dryness under reduced pressure to give 5-nitro-4-oxo-1-[4-(trifluoromethoxy)phenyl]cinnoline-3-carboxylic acid (0.120 g, 0.301 mmol, 67%) as a yellow solid. $^1$H NMR (400 MHz, DMSO-$d_6$): 13.67 (s, 1H), 7.89 (m, 4H), 7.72 (d, 2H), 7.39 (d, 1H)

TABLE 2

$^1$H NMR & LC/MS Data for selected compounds of Table 1.

| Cpd No. | Compound Name | Structure & $^1$H NMR Data | LC/MS |
|---|---|---|---|
| P1 | methyl 5-[(E)-N-methoxy-C-methyl-carbonimidoyl]-4-oxo-1-[4-(trifluoromethoxy)phenyl] cinnoline-3-carboxylate | 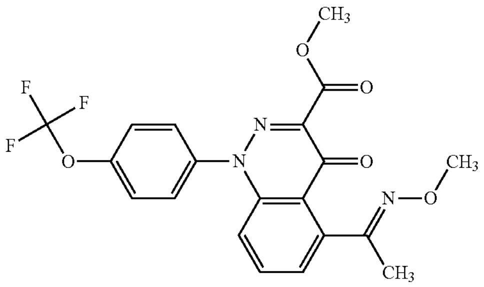 $^1$H NMR (400 MHz, $CDCl_3$) δ = 7.67-7.59 (m, 1H), 7.58-7.51 (m, 2H), 7.50-7.43 (m, 2H), 7.37-7.30 (m, 1H), 7.23-7.15 (m, 1H), 3.99-3.94 (m, 6H), 2.28-2.21 (m, 3H) | $R_t$ = 1.07 min; MS: m/z = 436 (M + H) |
| P2 | 5-[(E)-N-methoxy-C-methyl-carbonimidoyl]-4-oxo-1-[4-(trifluoromethoxy)phenyl] cinnoline-3-carboxylic acid | 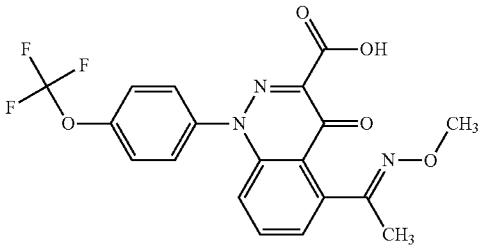 $^1$H NMR (400 MHz, $CDCl_3$) δ = 7.86-7.74 (m, 1H), 7.63-7.55 (m, 2H), 7.55-7.45 (m, 3H), 7.44-7.35 (m, 1H), 4.06-3.95 (m, 3H), 2.32-2.17 (m, 3H) | $R_t$ = 0.57 min; MS: m/z = 422 (M + H) |

TABLE 2-continued

| $^1$H NMR & LC/MS Data for selected compounds of Table 1. | | | |
|---|---|---|---|
| Cpd No. | Compound Name | Structure & $^1$H NMR Data | LC/MS |
| P3 | methyl 5-(1-ethoxyvinyl)-4-oxo-1-[4-(trifluoromethoxy)phenyl] cinnoline-3-carboxylate | 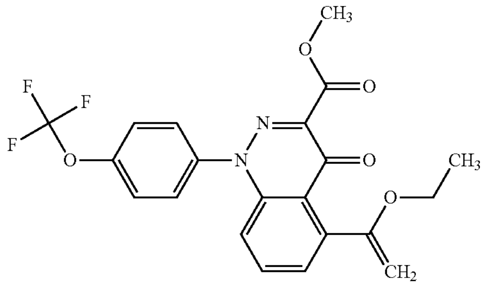 $^1$H NMR (400 MHz, $CDCl_3$) δ = 7.62-7.52 (m, 3H), 7.48-7.35 (m, 3H), 7.19-7.08 (m, 1H), 4.44-4.39 (m, 1H), 4.28-4.25 (m, 1H), 4.12-4.03 (m, 2H), 3.98-3.88 (m, 3H), 1.41-1.31 (m, 3H) | $R_t$ = 1.20 min; MS: m/z = 435 (M + H) |
| P4 | methyl 5-(1-methoxyvinyl)-4-oxo-1-[4-(trifluoromethoxy)phenyl] cinnoline-3-carboxylate | 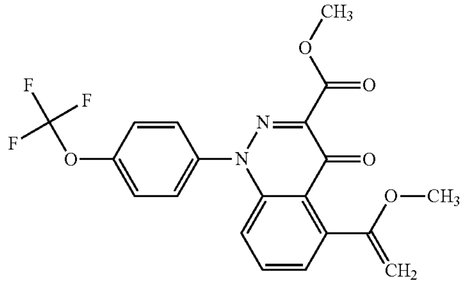 $^1$H NMR (400 MHz, $CDCl_3$) δ = 7.58-7.49 (m, 3H), 7.49-7.44 (m, 2H), 7.43-7.37 (m, 1H), 7.22-7.10 (m, 1H), 4.44-4.38 (m, 1H), 4.27-4.21 (m, 1H), 3.97-3.91 (m, 3H), 3.86-3.79 (m, 3H) | $R_t$ = 1.10 min; MS: m/z = 421 (M + H) |
| P5 | 5-oxazol-2-yl-4-oxo-1-[4-(trifluoromethoxy)phenyl] cinnoline-3-carboxylic acid | 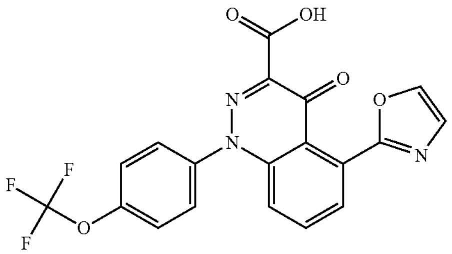 $^1$H NMR (400 MHz, $CDCl_3$) δ = 7.91-7.81 (m, 3H), 7.65-7.59 (m, 2H), 7.58-7.47 (m, 3H), 7.40-7.35 (m, 1H) | $R_t$ = 0.84 min; MS: m/z = 418 (M + H) |

TABLE 2-continued $^{1}H$ NMR & LC/MS Data for selected compounds of Table 1.

| Cpd No. | Compound Name | Structure & $^{1}H$ NMR Data | LC/MS |
|---|---|---|---|
| P6 | methyl 5-(4-fluorophenyl)-4-oxo-1-[4-(trifluoromethoxy)phenyl] cinnoline-3-carboxylate | 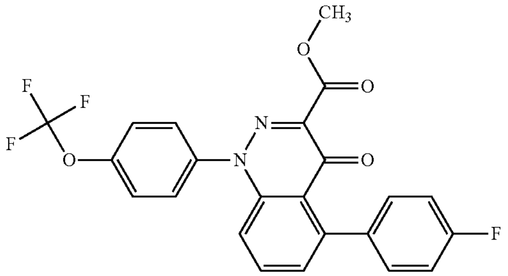 $^{1}H$ NMR (400 MHz, $CDCl_3$) δ = 7.63-7.56 (m, 3H), 7.50-7.45 (m, 2H), 7.31-7.27 (m, 3H), 7.20-7.15 (m, 1H), 7.13-7.06 (m, 2H), 3.93-3.80 (m, 3H) | $R_t$ = 1.23 min; MS: m/z = 459 (M + H) |
| P7 | methyl 5-cyano-4-oxo-1-[4-(trifluoromethoxy)phenyl] cinnoline-3-carboxylate | 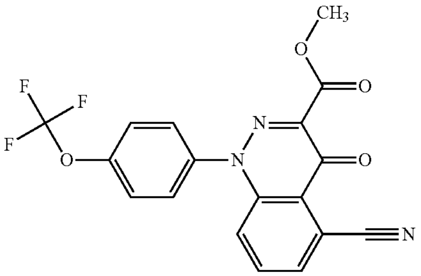 $^{1}H$ NMR (400 MHz, $CDCl_3$) δ = 7.93-7.86 (m, 1H), 7.77-7.70 (m, 1H), 7.61-7.55 (m, 2H), 7.50-7.41 (m, 3H), 4.03-3.91 (m, 3H) | $R_t$ = 0.94 min; MS: m/z = 390 (M + H) |
| P8 | 5-cyano-4-oxo-1-[4-(trifluoromethoxy)phenyl] cinnoline-3-carboxylic acid | 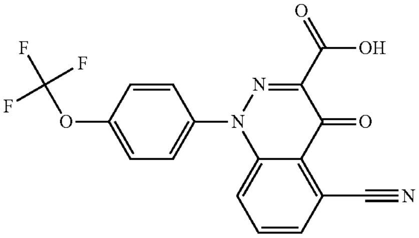 $^{1}H$ NMR (400 MHz, $CDCl_3$) δ = 8.11-8.04 (m, 1H), 7.97-7.84 (m, 1H), 7.65-7.58 (m, 3H), 7.54-7.39 (m, 3H) | $R_t$ = 0.83 min; MS: m/z = 376 (M + H) |

TABLE 2-continued

$^1$H NMR & LC/MS Data for selected compounds of Table 1.

| Cpd No. | Compound Name | Structure & $^1$H NMR Data | LC/MS |
|---|---|---|---|
| P9 | methyl 5-acetyl-4-oxo-1-[4-(trifluoromethoxy)phenyl] cinnoline-3-carboxylate | 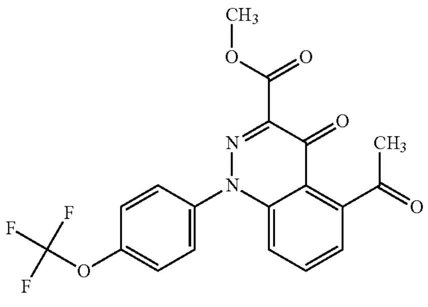 $^1$H NMR (400 MHz, $CDCl_3$) δ = 7.73-7.67 (m, 1H), 7.59-7.51 (m, 2H), 7.52-7.42 (m, 2H), 7.29-7.20 (m, 2H), 4.03-3.89 (m, 3H), 2.65-2.52 (m, 3H) | $R_t$ = 0.95 min; MS: m/z = 407 (M + H) |
| P10 | 5-acetyl-4-oxo-1-[4-(trifluoromethoxy)phenyl] cinnoline-3-carboxylic acid | 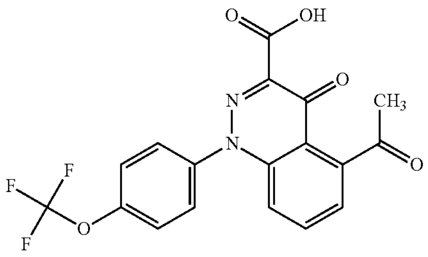 $^1$H NMR (400 MHz, $CDCl_3$) δ = 7.90-7.83 (m, 1H), 7.66-7.58 (m, 2H), 7.53-7.49 (m, 2H), 7.47-7.43 (m, 2H), 2.67-2.60 (m, 3H) | $R_t$ = 0.87 min; MS: m/z = 393 (M + H) |
| P11 | 1-(4-chlorophenyl)-5-(4-fluorophenoxy)-4-oxo-cinnoline-3-carboxylic acid | 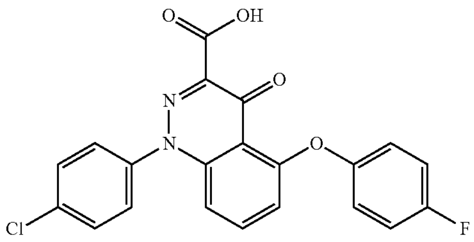 $^1$H NMR (400 MHz, $CDCl_3$) δ = 7.65-7.56 (m, 3H), 7.53-7.44 (m, 2H), 7.20-7.06 (m, 4H), 7.01-6.91 (m, 1H), 6.87-6.72 (m, 1H) | $R_t$ = 1.06 min; MS: m/z = 411 (M + H) |

TABLE 2-continued $^1$H NMR & LC/MS Data for selected compounds of Table 1.

| Cpd No. | Compound Name | Structure & $^1$H NMR Data | LC/MS |
|---|---|---|---|
| P12 | ethyl 5-[5-(difluoromethyl)isoxazol-3-yl]-4-oxo-1-[4-(trifluoromethoxy)phenyl] cinnoline-3-carboxylate | 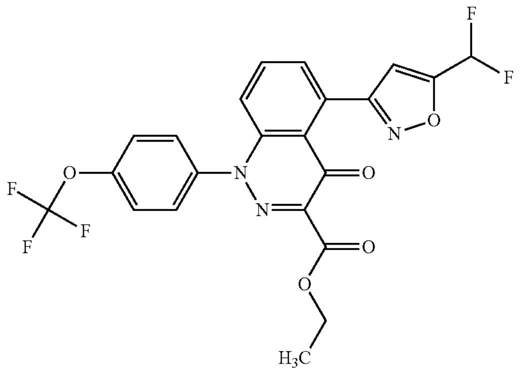<br>$^1$H NMR (400 MHz, DMSO-$d_6$) δ = 7.86 (s, 1H), 7.71 (d, 2H), 7.61 (m, 3H), 7.41 (m, 2H), 7.03 (s, 1H), 4.29 (t, 2H), 1.29 (q, 3H) | |
| P13 | 5-[5-(difluoromethyl)isoxazol-3-yl]-4-oxo-1-[4-(trifluoromethoxy)phenyl] cinnoline-3-carboxylic acid | 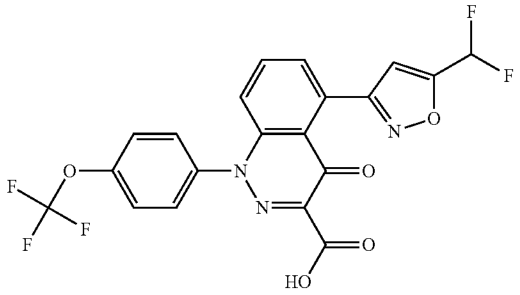<br>$^1$H NMR (400 MHz, DMSO-$d_6$) δ = 13.78 (s, 1H), 7.91 (m, 3H), 7.77 (m, 3H), 7.75 (m, 2H), 7.05 (d, 1H) | |
| P14 | ethyl 5-[(E)-N-hydroxy-C-methyl-carbonimidoyl]-4-oxo-1-[4-(trifluoromethoxy)phenyl] cinnoline-3-carboxylate | 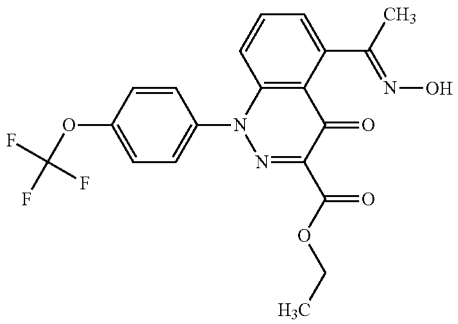<br>$^1$H NMR (400 MHz, DMSO-$d_6$) δ = 10.89 (s, 1H), 7.85 (d, 2H), 7.72 (d, 3H), 7.30 (d, 1H), 7.17 (d, 1H), 4.32 (m, 2H), 2.04 (s, 3H), 1.28 | |

TABLE 2-continued

| $^1H$ NMR & LC/MS Data for selected compounds of Table 1. | | | |
|---|---|---|---|
| Cpd No. | Compound Name | Structure & $^1H$ NMR Data | LC/MS |
| P15 | 5-[(E)-N-hydroxy-C-methyl-carbonimidoyl]-4-oxo-1-[4-(trifluoromethoxy)phenyl] cinnoline-3-carboxylic acid | 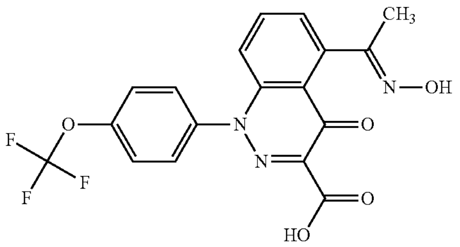<br>$^1H$ NMR (400 MHz, DMSO-$d_6$) δ = 13.9 (brs, 1H), 10.97 (s, 1H), 7.87 (m, 3H), 7.72 (d, 2H), 7.38 (d, 1H), 7.21 (d, 1H), 2.07 (s, 3H) | |
| P16 | ethyl 4-oxo-1-[4-(trifluoromethoxy)phenyl]-5-vinyl-cinnoline-3-carboxylate | 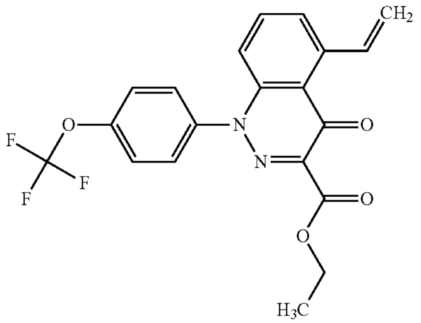<br>$^1H$ NMR (400 MHz, $CDCl_3$) δ = 8.14 (m, 1H), 7.56 (m, 3H), 7.53 (d, 3H), 7.08 (d, 1H), 5.65 (d, 1H), 5.47 (d, 1H), 4.47 (q, 2H), 1.42 (t, 3H) | |
| P17 | 4-oxo-1-[4-(trifluoromethoxy)phenyl]-5-vinyl-cinnoline-3-carboxylic acid | 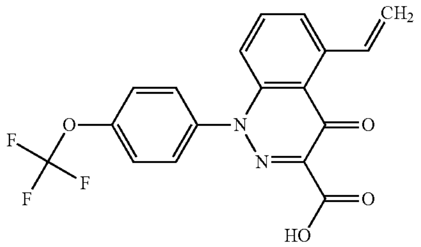<br>$^1H$ NMR (400 MHz, DMSO-$d_6$) δ = 14.08 (s, 1H), 8.04 (m, 1H), 7.79 (m, 2H), 7.72 (m, 1H), 7.64 (m, 2H), 7.55 (m, 1H), 7.18 (d, 1H), 5.79 (d, 1H), 5.74 (d, 1H) | |

TABLE 2-continued

| $^1$H NMR & LC/MS Data for selected compounds of Table 1. | | | |
|---|---|---|---|
| Cpd No. | Compound Name | Structure & $^1$H NMR Data | LC/MS |
| P18 | ethyl 4-oxo-5-(2-oxoethyl)-1-[4-(trifluoromethoxy)phenyl] cinnoline-3-carboxylate | 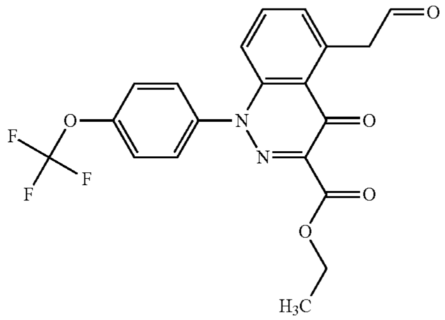 $^1$H NMR (400 MHz, DMSO-$d_6$) δ = 9.76 (s, 1H), 7.87 (t, 2H), 7.74 (m, 3H), 7.38 (d, 1H), 7.12 (d, 1H), 4.30 (m, 4H), 1.29 (m, 3H) | |
| P19 | 5-(4-chloropyrazol-1-yl)-4-oxo-1-[4-(trifluoroethoxy)phenyl] cinnoline-3-carboxylic acid | 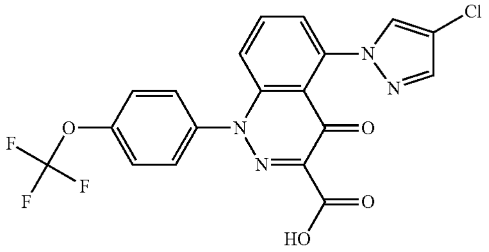 $^1$H NMR (400 MHz, DMSO-$d_6$) δ = 13.81 (t, 1H), 8.24 (s, 1H), 7.91 (m, 4H), 7.72 (m, 2H), 7.62 (d, 1H), 7.36 (d, 1H) | |
| P20 | 4-oxo-1-[4-(trifluoromethoxy)phenyl]-5-[4-(trifluoromethyl)triazol-2-yl]cinnoline-3-carboxylic acid | 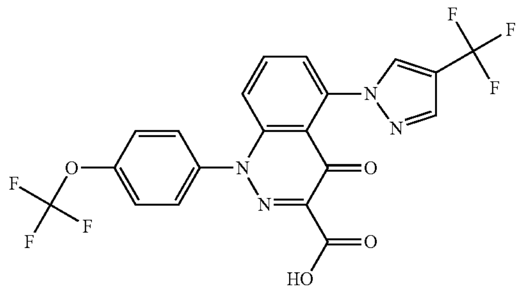 $^1$H NMR (400 MHz, DMSO-$d_6$) δ = 13.6 (s, 1H), 8.75 (s, 1H), 7.97 (t, 1H), 7.91 (m, 2H), 7.73 (d, 1H), 7.53 (d, 2H), 7.51 (d, 1H) | |

TABLE 2-continued $^1$H NMR & LC/MS Data for selected compounds of Table 1.

| Cpd No. | Compound Name | Structure & $^1$H NMR Data | LC/MS |
|---|---|---|---|
| P21 | 4-oxo-1-[4-(trifluoromethoxy)phenyl]-5-[4-(trifluoromethyl)triazol-1-yl]cinnoline-3-carboxylic acid | 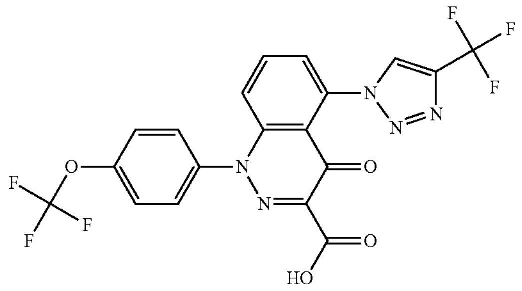 $^1$H NMR (400 MHz, DMSO-$d_6$) δ = 13.80 (s, 1H), 12.30 (s, 1H), 7.93 (m, 3H), 7.72 (d, 2H), 7.53 (d, 1H), 6.81 (d, 1H) | |
| P22 | 4-oxo-1-[4-(trifluoromethoxy)phenyl]-5-[4-(trifluoromethyl)pyrazol-1-yl]cinnoline-3-carboxylic acid | 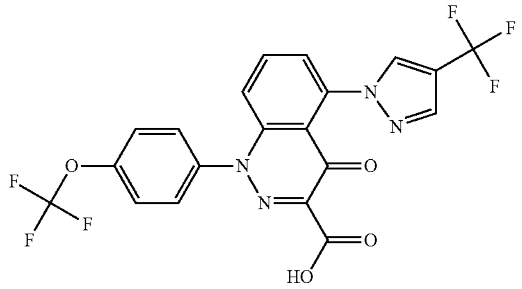 $^1$H NMR (400 MHz, DMSO-$d_6$) δ = 8.69 (s, 1H), 8.17 (s, 1H), 7.88 (m, 3H), 7.71 (d, 2H), 7.60 (d, 1H), 7.36 (d, 1H) | |
| P23 | 4-oxo-5-pyrrolidin-1-yl-1-[4-(trifluoromethoxy)phenyl] cinnoline-3-carboxylic acid | 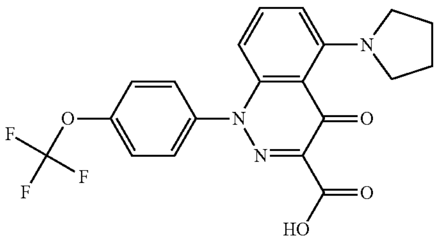 $^1$H NMR (400 MHz, DMSO-$d_6$) δ = 14.46 (s, 1H), 7.81 (d, 2H), 7.66 (d, 2H), 7.48 (d, 1H), 6.77 (d, 1H), 6.22 (d, 1H), 3.33 (s, 4H), 1.98 (s, 4H) | |
| P24 | 4-oxo-5-(1-piperidyl)-1-[4-(trifluoromethoxy)phenyl] cinnoline-3-carboxylic acid | 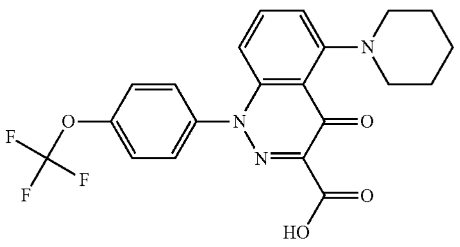 $^1$H NMR (400 MHz, DMSO-$d_6$) δ = 15.3 (s, 1H), 7.62 (m, 3H), 7.51 (d, 2H), 7.01 (d, 1H), 6.65 (d, 1H), 3.25 (s, 4H), 1.95 (s, 4H), 1.65 (s, 2H) | |

TABLE 2-continued

| Cpd No. | Compound Name | Structure & ¹H NMR Data | LC/MS |
|---|---|---|---|
| P25 | 5-morpholino-4-oxo-1-[4-(trifluoromethoxy)phenyl]cinnoline-3-carboxylic acid | 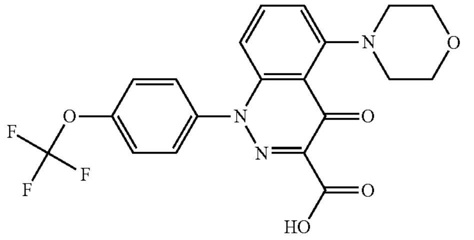 ¹H NMR (400 MHz, DMSO-$d_6$) δ = 14.85 (s, 1H), 7.83 (m, 3H), 7.72 (d, 2H), 7.06 (d, 1H), 6.62 (d, 1H), 3.85 (m, 4H), 3.12 (m, 4H) | |
| P26 | ethyl 5-morpholino-4-oxo-1-[4-(trifluoromethoxy)phenyl]cinnoline-3-carboxylate | 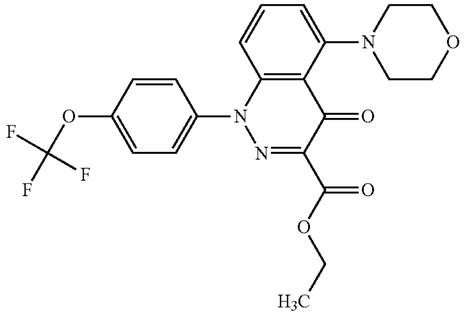 ¹H NMR (400 MHz, $CDCl_3$) δ = 7.55 (d, 2H), 7.45 (m, 3H), 6.90 (d, 1H), 6.75 (d, 1H), 4.45 (q, 2H), 4.05 (m, 4H), 3.25 (m, 4H), 1.44 (t, 3H) | |
| P27 | ethyl 4-oxo-5-(1-piperidyl)-1-[4-(trifluoromethoxy)phenyl]cinnoline-3-carboxylate | 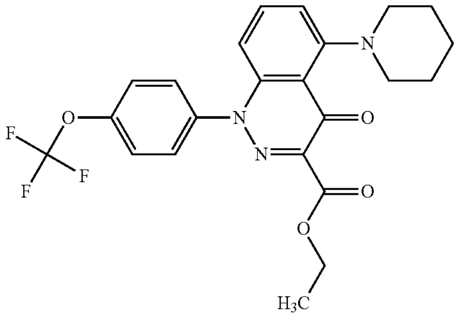 ¹H NMR (400 MHz, $CDCl_3$) δ = 7.85 (d, 2H), 7.65 (d, 2H), 7.55 (t, 1H), 6.90 (d, 1H), 6.55 (d, 1H), 4.35 (q, 2H), 3.05 (m, 4H), 1.82 (m, 4H), 1.60 (m, 2H), 1.25 (t, 3H) | |

¹H NMR & LC/MS Data for selected compounds of Table 1.

TABLE 2-continued

$^1$H NMR & LC/MS Data for selected compounds of Table 1.

| Cpd No. | Compound Name | Structure & $^1$H NMR Data | LC/MS |
|---|---|---|---|
| P28 | ethyl 4-oxo-5-pyrrolidin-1-yl-1-[4-(trifluoromethoxy)phenyl] cinnoline-3-carboxylate | 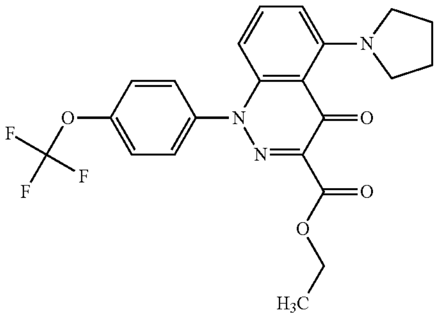 $^1$H NMR (400 MHz, $CDCl_3$) δ = 7.55 (m, 2H), 7.41 (m, 2H), 7.26 (d, 1H), 6.58 (d, 1H), 6.22 (d, 1H), 4.43 (m, 2H), 3.40 (s, 4H), 1.99 (s, 4H), 1.38 (t, 3H) | |
| P29 | ethyl 5-(1-ethoxyvinyl)-4-oxo-1-[4-(trifluoromethoxy)phenyl] cinnoline-3-carboxylate | 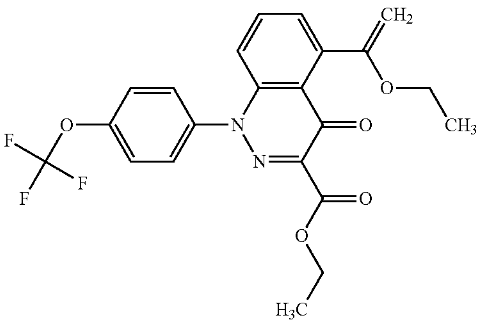 $^1$H NMR (400 MHz, $CDCl_3$) δ = 7.57-7.50 (m, 3H), 7.47-7.42 (m, 2H), 7.40 (m, 1H), 7.13 (m, 1H), 4.46-4.38 (m, 3H), 4.28 (d, 1H), 4.08 (q, 2H), 1.37 (q, 6H) | |
| P30 | ethyl 5-acetyl-4-oxo-1-[4-(trifluoromethoxy)phenyl] cinnoline-3-carboxylate | 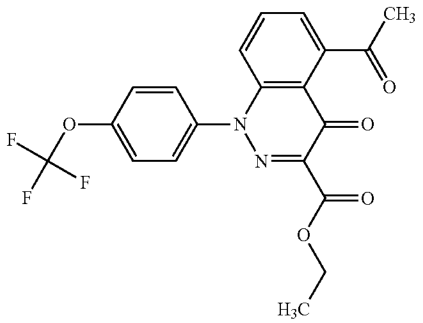 $^1$H NMR (400 MHz, $CDCl_3$) δ = 7.68 (dd, 1H), 7.625-7.54 (m, 2H), 7.51-7.44 (m, 2H), 7.29-7.23 (m, 2H), 4.45 (q, 2H), 2.61 (s, 3H), 1.39 (t, 3H) | |

TABLE 2-continued

$^1$H NMR & LC/MS Data for selected compounds of Table 1.

| Cpd No. | Compound Name | Structure & $^1$H NMR Data | LC/MS |
|---|---|---|---|
| P31 | ethyl 4-oxo-1-[4-(trifluoromethoxy)phenyl]-5-[4-(trifluoromethyl)pyrazol-1-yl]cinnoline-3-carboxylate | 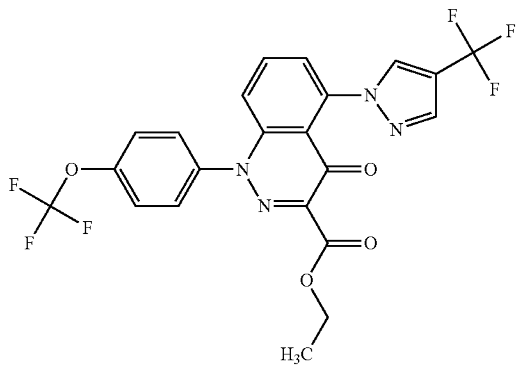 $^1$H NMR (400 MHz, DMSO-$d_6$) δ = 8.66 (s, 1H), 8.16 (s, 1H), 7.89 (m, 3H), 7.72 (m, 2H), 7.64 (d, 1H), 7.34 (d, 1H), 4.30 (q, 2H), 1.26 (t, 3H) | |
| P32 | ethyl 5-(4-chloropyrazol-1-yl)-4-oxo-1-[4-(trifluoromethoxy)phenyl] cinnoline-3-carboxylate | 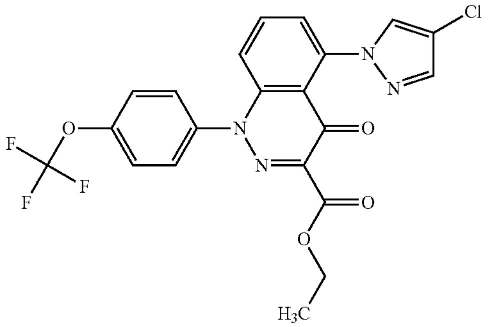 $^1$H NMR (400 MHz, DMSO-$d_6$) δ = 8.21 (s, 1H), 7.87 (m, 4H), 7.82 (d, 2H), 7.56 (d, 1H), 7.28 (m, 1H), 4.29 (d, 2H), 1.27 (t, 3H) | |
| P33 | ethyl 4-oxo-1-[4-(trifluoromethoxy)phenyl]-5-[4-(trifluoromethyl)triazol-1-yl]cinnoline-3-carboxylate | 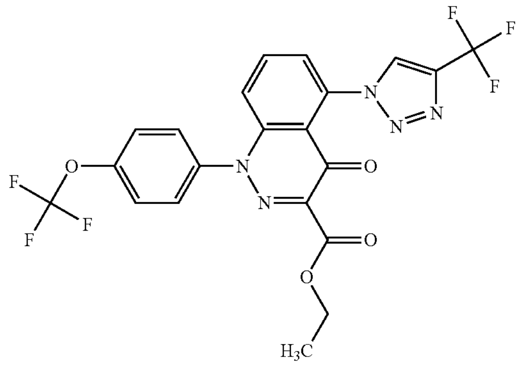 $^1$H NMR (400 MHz, $CDCl_3$) δ = 7.77 (s, 1H), 7.60 (t, 1H), 7.55 (m, 3H), 7.46 (m, 3H), 4.40 (q, 2H), 1.35 (t, 3H) | |

TABLE 2-continued

| $^1$H NMR & LC/MS Data for selected compounds of Table 1. | | | |
|---|---|---|---|
| Cpd No. | Compound Name | Structure & $^1$H NMR Data | LC/MS |
| P34 | ethyl 4-oxo-1-[4-(trifluoromethoxy)phenyl]-5-[4-(trifluoromethyl)triazol-2-yl]cinnoline-3-carboxylate | 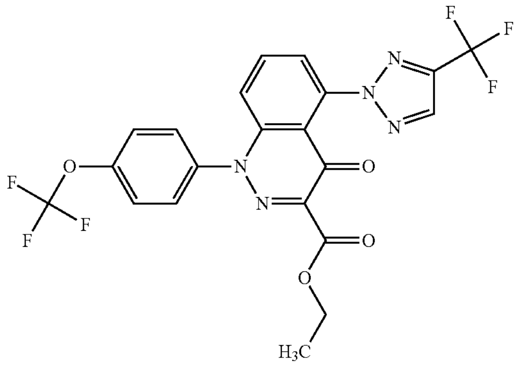 $^1$H NMR (400 MHz, $CDCl_3$) δ = 8.15 (s, 1H), 7.78 (t, 1H), 7.61 (t, 3H), 7.45 (d, 2H), 7.43 (d, 1H), 4.41 (q, 2H), 1.36 (t, 3H) | |
| P35 | ethyl 5-(cyanomethyl)-4-oxo-1-[4-(trifluoromethoxy)phenyl] cinnoline-3-carboxylate | 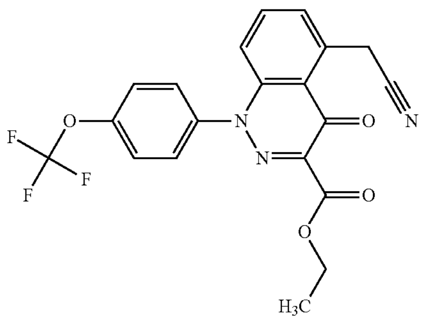 $^1$H NMR (400 MHz, DMSO-$d_6$) δ = 7.86 (d, 2H), 7.79 (m, 1H), 7.74 (d, 2H), 7.65 (d, 1H), 7.29 (d, 1H), 4.59 (s, 2H), 4.35 (q, 2H), 1.30 (t, 3H) | |
| P36 | ethyl 5-(difluoromethyl)-4-oxo-1-[4-(trifluoromethoxy)phenyl] cinnoline-3-carboxylate | 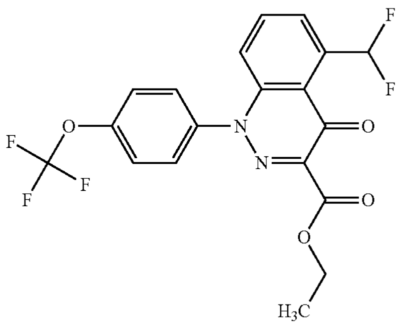 $^1$H NMR (400 MHz, $CDCl_3$) δ = 8.22 (s, 2H), 7.93 (t, 1H), 7.73 (t, 2H), 7.45 (d, 2H), 7.32 (s, 1H), 4.45 (q, 2H), 1.41 (t, 3H) | |

TABLE 2-continued

| Cpd No. | Compound Name | Structure & $^1$H NMR Data | LC/MS |
|---|---|---|---|
| | | $^1$H NMR & LC/MS Data for selected compounds of Table 1. | |
| P37 | 5-(difluoromethyl)-4-oxo-1-[4-(trifluoromethoxy)phenyl]cinnoline-3-carboxylic acid | 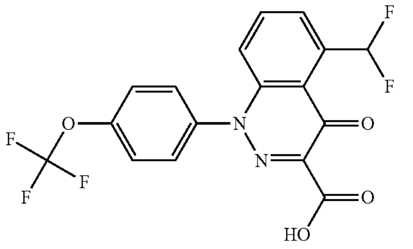 $^1$H NMR (400 MHz, DMSO-$d_6$) δ = 13.85 (s, 1H), 8.23 (m, 3H), 7.85 (d, 2H), 7.75 (d, 2H), 7.42 (d, 1H) | |
| P38 | ethyl 5-cyano-4-oxo-1-[4-(trifluoromethoxy)phenyl]cinnoline-3-carboxylate | 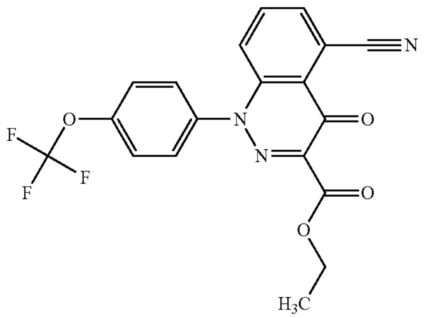 $^1$H NMR (400 MHz, $CDCl_3$) δ = 7.88 (m, 1H), 7.72 (m, 1H), 7.61-7.54 (m, 2H), 7.51-7.46 (m, 2H), 7.44 (m, 1H), 4.47 (q, 2H), 1.41 (t, 3H) | |
| P39 | ethyl 5-nitro-4-oxo-1-[4-(trifluoromethoxy)phenyl]cinnoline-3-carboxylate | 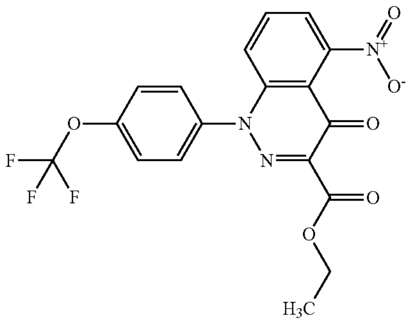 $^1$H NMR (400 MHz, DMSO-$d_6$) δ = 7.95 (m, 4H), 7.75 (d, 2H), 7.36 (m, 1H), 4.39 (q, 2H), 1.23 (t, 3H) | |
| P40 | 5-nitro-4-oxo-1-[4-(trifluoromethoxy)phenyl]cinnoline-3-carboxylic acid | 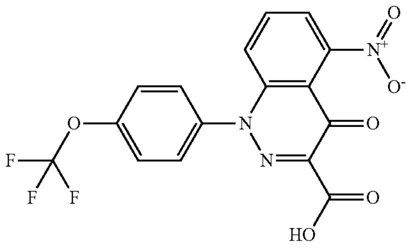 $^1$H NMR (400 MHz, DMSO-$d_6$) δ = 13.67 (s, 1H), 7.89 (m, 4H), 7.72 (d, 2H), 7.39 (d, 1H) | |

TABLE 2-continued

| Cpd No. | Compound Name | Structure & $^1$H NMR Data | LC/MS |
|---|---|---|---|
| | | $^1$H NMR & LC/MS Data for selected compounds of Table 1. | |
| P41 | 5-cyano-1-(3,4-dimethoxyphenyl)-4-oxo-cinnoline-3-carboxylic acid | 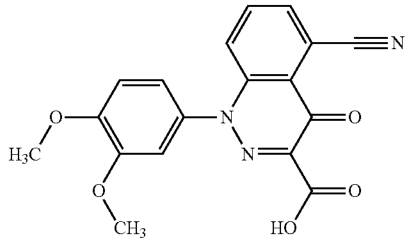 $^1$H NMR (400 MHz, $CDCl_3$) δ = 13.78 (brs, 1H), 8.10-8.00 (m, 1H), 7.89 (m, 1H), 7.68 (m, 1H), 7.10-7.03 (m, 2H), 7.01 (d, 1H), 3.99 (s, 3H), 3.91 (s, 3H) | |
| P42 | ethyl 5-cyano-1-(3,4-dimethoxyphenyl)-4-oxo-cinnoline-3-carboxylate | 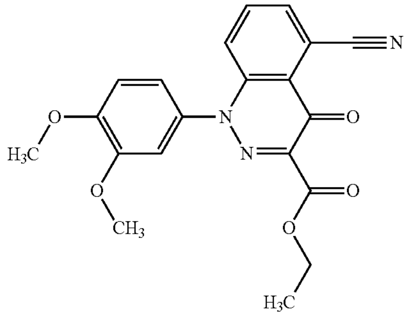 $^1$H NMR (400 MHz, $CDCl_3$) δ = 7.85 (m, 1H), 7.69 (m, 1H), 7.45 (m, 1H), 7.09-7.01 (m, 2H), 6.98 (m, 1H), 4.46 (q, 2H), 3.98 (s, 3H), 3.92 (s, 3H), 1.41 (t, 3H) | |
| P43 | 1-(4-chlorophenyl)-5-cyano-4-oxo-cinnoline-3-carboxylic acid | 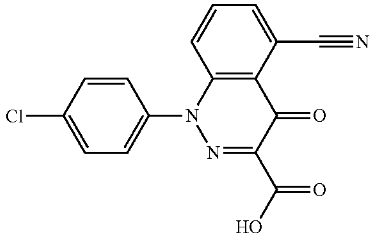 $^1$H NMR (400 MHz, DMSO-$d_6$) δ = 13.82 (s, 1H), 8.12 (d, 1H), 7.90 (d, 1H), 7.78 (m, 2H), 7.72 (d, 2H), 7.52 (d, 1H) | |
| P44 | 5-cyano-1-(4-methylsulfanylphenyl)-4-oxo-cinnoline-3-carboxylic acid | 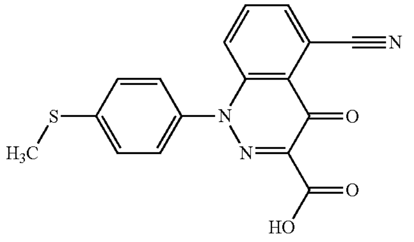 $^1$H NMR (400 MHz, DMSO-$d_6$) δ = 13.65 (s, 1H), 8.12 (d, 1H), 7.90 (d, 1H), 7.89 (d, 2H), 7.52 (m, 3H), 2.57 (s, 3H) | |

TABLE 2-continued

| $^1$H NMR & LC/MS Data for selected compounds of Table 1. | | | |
|---|---|---|---|
| Cpd No. | Compound Name | Structure & $^1$H NMR Data | LC/MS |
| P45 | 1-(3-chloro-5-methyl-phenyl)-5-cyano-4-oxo-cinnoline-3-carboxylic acid | 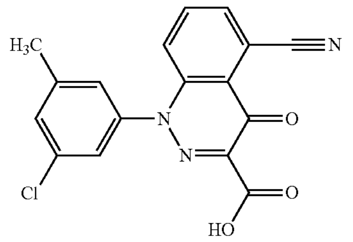 $^1$H NMR (400 MHz, DMSO-$d_6$) δ = 13.74 (s, 1H), 8.13 (d, 1H), 8.11 (d, 1H), 7.90 (d, 2H), 7.61 (m, 1H), 7.50 (d, 1H), 2.43 (s, 3H) | |
| P46 | 5-cyano-4-oxo-1-[4-(trifluoromethyl)phenyl]cinnoline-3-carboxylic acid | 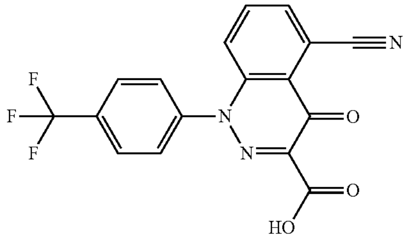 $^1$H NMR (400 MHz, DMSO-$d_6$) δ = 8.10 (m, 3H), 7.90 (m, 3H), 7.56 (d, 1H) | |
| P47 | 5-cyano-1-(4-cyanophenyl)-4-oxo-cinnoline-3-carboxylic acid | 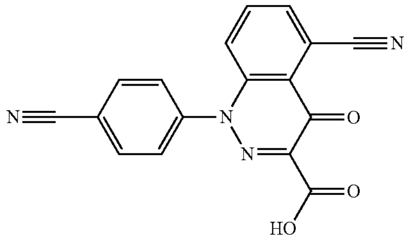 $^1$H NMR (400 MHz, DMSO-$d_6$) δ = 8.19 (d, 2H), 8.11 (d, 1H), 7.89 (m, 3H), 7.56 (d, 1H) | |
| P48 | 5-cyano-4-oxo-1-(7-quinolyl)cinnoline-3-carboxylic acid | 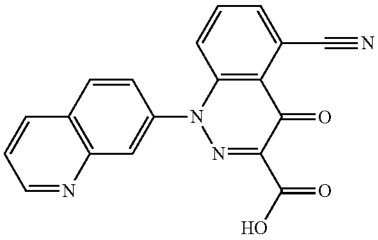 $^1$H NMR (400 MHz, DMSO-$d_6$) δ = 9.09 (d, 1H), 8.63 (d, 1H), 8.35 (m, 2H), 8.14 (d, 1H), 7.89 (m, 2H), 7.75 (m, 1H), 7.64 (d, 1H) | |

TABLE 2-continued

| ¹H NMR & LC/MS Data for selected compounds of Table 1. | | | |
|---|---|---|---|
| Cpd No. | Compound Name | Structure & $^1$H NMR Data | LC/MS |
| P49 | 5-cyano-1-(2,2-difluoro-1,3-benzodioxol-5-yl)-4-oxo-cinnoline-3-carboxylic acid | 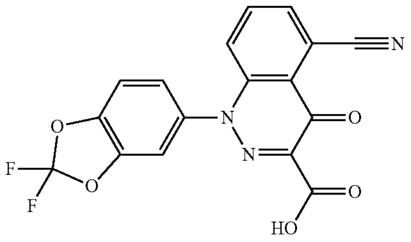 $^1$H NMR (400 MHz, DMSO-$d_6$) δ = 13.7 (s, 1H), 8.12 (d, 1H), 7.88 (m, 2H), 7.73 (d, 1H), 7.58 (m, 2H) | |
| P50 | 5-cyano-1-(1-methylindazol-6-yl)-4-oxo-cinnoline-3-carboxylic acid | 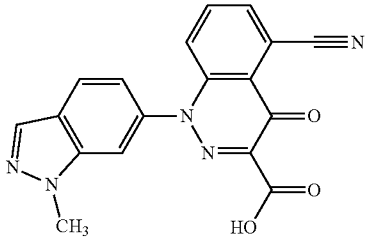 $^1$H NMR (400 MHz, DMSO-$d_6$) δ = 13.7 (s, 1H), 8.27 (s, 1H), 8.09 (m, 3H), 7.87 (t, 1H), 7.52 (d, 1H), 7.37 (d, 1H), 4.09 (s, 3H) | |
| P51 | ethyl 5-bromo-4-oxo-1-(2,2,3,3-tetrafluoro-1,4-benzodioxin-6-yl)cinnoline-3-carboxylate | 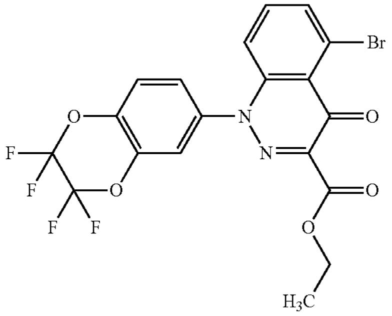 $^1$H NMR (400 MHz, $CDCl_3$) δ = 7.72 (dd, 1H), 7.42-7.32 (m, 4H), 7.11 (dd, 1H) ,4.45 (q, 2H), 1.41 (t, 3H) | |
| P52 | ethyl 5-cyano-4-oxo-1-(2,2,3,3-tetrafluoro-1,4-benzodioxin-6-yl)cinnoline-3-carboxylate | 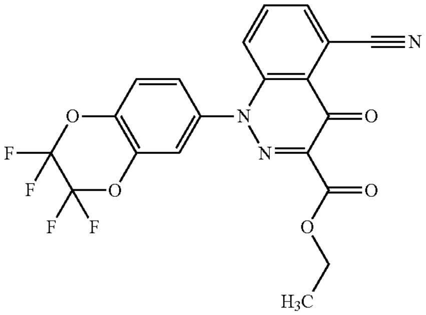 $^1$H NMR (400 MHz, $CDCl_3$) δ = 7.88 (dd, 1H), 7.76 (dd, 1H), 7.48-7.38 (m, 4H), 4.46 (q, 2H), 1.41 (t, 3H) | |

TABLE 2-continued

| Cpd No. | Compound Name | Structure & $^{1}H$ NMR Data | LC/MS |
|---|---|---|---|
| P53 | 5-cyano-4-oxo-1-(2,2,3,3-tetrafluoro-1,4-benzodioxin-6-yl)cinnoline-3-carboxylic acid | 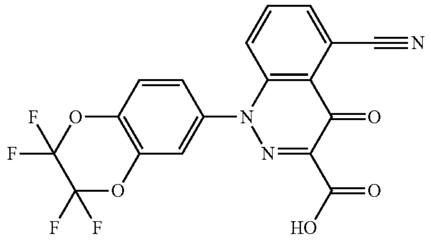 $^{1}H$ NMR (400 MHz, $CDCl_3$) δ = 8.08 (dd, 1H), 7.95 (dd, 1H), 7.70-7.62 (m, 1H), 7.48-7.41 (m, 3H) | |
| P54 | ethyl 5-acetyl-4-oxo-1-(2,2,3,3-tetrafluoro-1,4-benzodioxin-6-yl)cinnoline-3-carboxylate | 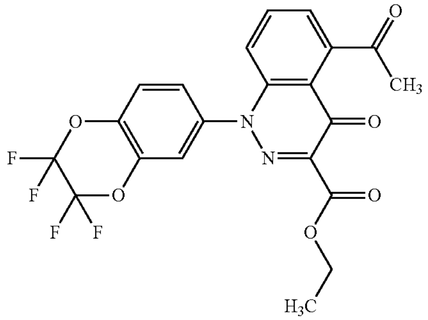 $^{1}H$ NMR (400 MHz, $CDCl_3$) δ = 7.70 (dd, 1H), 7.43-7.35 (m, 3H), 7.30-7.24 (m, 2H), 4.45 (q, 2H), 2.61 (s, 3H), 1.39 (t, 3H) | |
| P55 | 5-acetyl-4-oxo-1-(2,2,3,3-tetrafluoro-1,4-benzodioxin-6-yl)cinnoline-3-carboxylic acid | 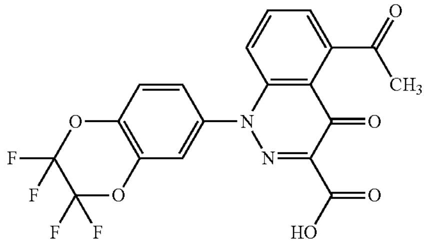 $^{1}H$ NMR (400 MHz, $CDCl_3$) δ = 7.89 (dd, 1H), 7.48-7.41 (m, 5H), 2.63 (s, 3H) | |
| P56 | 1-(3-chloro-4-methyl-phenyl)-5-cyano-4-oxo-cinnoline-3-carboxylic acid | 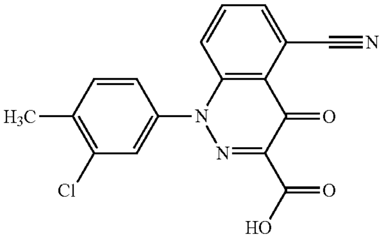 $^{1}H$ NMR (400 MHz, $CDCl_3$) δ = 8.11 (d, 1H), 7.84 (m, 2H), 7.67 (d, 1H), 7.56 (m, 2H), 2.46 (s, 3H) | |

$^{1}H$ NMR & LC/MS Data for selected compounds of Table 1.

TABLE 2-continued $^1$H NMR & LC/MS Data for selected compounds of Table 1.

| Cpd No. | Compound Name | Structure & $^1$H NMR Data | LC/MS |
|---|---|---|---|
| P57 | 5-cyano-1-(3,4-dichlorophenyl)-4-oxo-cinnoline-3-carboxylic acid | 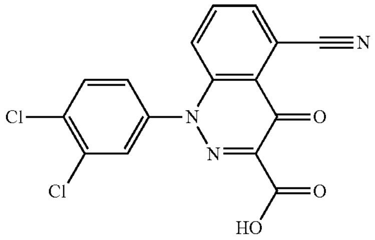<br>$^1$H NMR (400 MHz, $CDCl_3$) δ = 8.08 (d, 1H), 7.92 (t, 1H), 7.75 (d, 1H), 7.67 (d, 1H), 7.64 (d, 1H), 7.39 (m, 1H) | |
| P58 | 5-cyano-1-(3-cyanophenyl)-4-oxo-cinnoline-3-carboxylic acid | 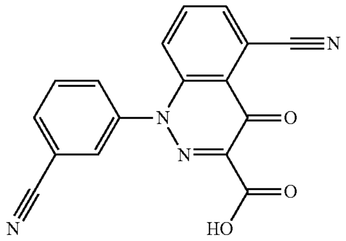<br>$^1$H NMR (400 MHz, DMSO-$d_6$) δ = 8.26 (d, 1H), 8.14 (m, 2H), 8.04 (d, 1H), 7.89 (m, 2H), 7.57 (d, 1H) | |
| P59 | 1-(3-chlorophenyl)-5-cyano-4-oxo-cinnoline-3-carboxylic acid | 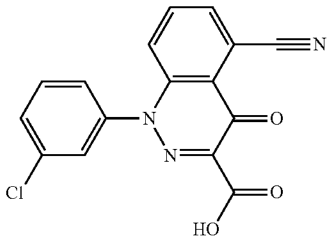<br>$^1$H NMR (400 MHz, DMSO-$d_6$) δ = 8.13 (d, 1H), 7.88 (m, 2H), 7.72 (m, 3H), 7.54 (d, 1H) | |
| P60 | 1-(3-chloro-4-fluoro-phenyl)-5-cyano-4-oxo-cinnoline-3-carboxylic acid | 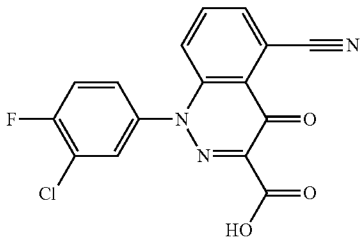<br>$^1$H NMR (400 MHz, DMSO-$d_6$) δ = 8.12 (d, 1H), 8.09 (d, 1H), 7.89 (t, 1H), 7.76 (d, 2H), 7.57 (d, 1H) | |

Biological Examples

Seeds of a variety of test species are sown in standard soil in pots (*Amaranthus retoflexus* (AMARE), *Solarium nigrum* (SOLNI), *Setaria faberi* (SETFA), *Lolium perenne* (LOLPE), *Echinochloa crus-galli* (ECHCG), *Ipornoea hederacea* (IPOHE)). After 8 days cultivation under controlled conditions in a glasshouse (at 24° C./16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5). Compounds are applied at 1000 g/ha unless otherwise stated. The test plants are then grown in a glasshouse under controlled conditions in a glasshouse (at 24° C./16° C., day/night; 14 hours light; 65% humidity) and watered twice daily. After 13 days the test is evaluated for the percentage damage caused to the plant. The biological activities are shown in the following table on a five-point scale (5=81-100%; 4=61-80%; 3=41-60%; 2=21-40%; 1=10-20%; 0=0%; –=not tested).

TABLE B1

| Pre-emergence Test | | | | | | | | |
|---|---|---|---|---|---|---|---|---|
| Cpd No. | SOLNI | AMARE | IPOHE | ECHCG | LOLPE | SETFA | ZEAMX | ABUTH |
| P1 | 1 | 1 | 1 | 5 | 4 | 5 | — | — |
| P2 | 2 | 0 | 2 | 5 | 4 | 5 | 4 | 3 |
| P3 | 2 | 0 | 2 | 4 | 4 | 5 | 4 | 3 |
| P4 | 0 | 0 | 0 | 5 | 5 | 5 | — | — |
| P5 | 0 | 0 | 0 | 0 | 0 | 1 | — | — |
| P6 | 0 | 0 | 0 | 0 | 0 | 0 | — | — |
| P7 | 0 | 0 | 0 | 2 | 0 | 1 | — | — |
| P8 | 1 | 2 | 1 | 5 | 4 | 5 | 0 | 1 |
| P9 | 3 | 1 | 3 | 5 | 4 | 5 | 4 | 3 |
| P10 | 1 | 1 | 0 | 5 | 4 | 5 | — | — |
| P11 | 5 | 3 | 0 | 0 | 0 | 0 | — | — |
| P12 | — | 0 | 0 | 0 | — | 0 | | 0 |
| P13 | — | 0 | 0 | 0 | — | 0 | 0 | 0 |
| P14 | — | 1 | 0 | 4 | — | 4 | 2 | 1 |
| P15 | — | 2 | 0 | 4 | — | 5 | 3 | 2 |
| P16 | — | 2 | 1 | 2 | — | 3 | 1 | 2 |
| P17 | — | 2 | 0 | 2 | — | 3 | 1 | 1 |
| P18 | — | 0 | 0 | 0 | — | 1 | 0 | 0 |
| P19 | — | 0 | 0 | 3 | — | 4 | 1 | 0 |
| P20 | — | 0 | 0 | 0 | — | 0 | 0 | 0 |
| P21 | — | 1 | 1 | 1 | — | 2 | 0 | 0 |
| P22 | — | 2 | 0 | 0 | — | 0 | 0 | 0 |
| P23 | — | 0 | 0 | 0 | — | 0 | 0 | 0 |
| P24 | — | 0 | 0 | 1 | — | 0 | 0 | 1 |
| P25 | — | 0 | 0 | 0 | — | 0 | 0 | 0 |
| P26 | — | 0 | 0 | 0 | — | 0 | 0 | 0 |
| P27 | — | 0 | 0 | 0 | — | 0 | 0 | 0 |
| P28 | — | 0 | 0 | 0 | — | 0 | 0 | 0 |
| P29 | — | 1 | 1 | 4 | — | 5 | 1 | 1 |
| P30 | — | 1 | 1 | 4 | — | 5 | 4 | 2 |
| P31 | — | 0 | 0 | 0 | — | 0 | 0 | 0 |
| P32 | — | 2 | 0 | 4 | — | 4 | 2 | 2 |
| P33 | — | 0 | 0 | 0 | — | 0 | 1 | 0 |
| P34 | — | 0 | 0 | 0 | — | 0 | 2 | 0 |
| P35 | — | 1 | 0 | 5 | — | 5 | 2 | 0 |
| P36 | — | 0 | 1 | 0 | — | 2 | 0 | 1 |
| P37 | — | 0 | 0 | 0 | — | 0 | 0 | 0 |
| P38 | — | 3 | 1 | 5 | — | 5 | 2 | 0 |
| P39 | — | 0 | 0 | 2 | — | 5 | 0 | 1 |
| P40 | — | 2 | 0 | 2 | — | 5 | 0 | 3 |
| P41 | — | 0 | 0 | 0 | — | 0 | 0 | 0 |
| P42 | — | 0 | 0 | 0 | — | 0 | 0 | 0 |

TABLE 82

| Post-emergence Test | | | | | | | | |
|---|---|---|---|---|---|---|---|---|
| Cpd No. | SOLNI | AMARE | IPOHE | ECHCG | LOLPE | SETFA | ZEAMX | ABUTH |
| P1 | 3 | 2 | 2 | 5 | 4 | 4 | — | — |
| P2 | 2 | 1 | 3 | 4 | 3 | 4 | 3 | 4 |
| P3 | 4 | 1 | 3 | 4 | 4 | 4 | 3 | 3 |
| P4 | 0 | 0 | 4 | 4 | 4 | 4 | — | — |
| P5 | 2 | 1 | 0 | 3 | 2 | 4 | — | — |
| P6 | 0 | 0 | 0 | 0 | 0 | 0 | — | — |
| P7 | 2 | 1 | 0 | 1 | 0 | 1 | — | — |
| P8 | 3 | 4 | 4 | 4 | 4 | 4 | 2 | 1 |
| P9 | 4 | 1 | 2 | 4 | 4 | 4 | 4 | 3 |
| P10 | 4 | 1 | 4 | 4 | 4 | 4 | — | — |
| P11 | 1 | 5 | 0 | 0 | 0 | 0 | — | — |
| P12 | — | 0 | 2 | 0 | — | 2 | 1 | 1 |
| P13 | — | 1 | 2 | 3 | — | 4 | 3 | 0 |
| P14 | — | 2 | 1 | 4 | — | 3 | 4 | 3 |
| P15 | — | 1 | 3 | 4 | — | 3 | 3 | 3 |
| P16 | — | 2 | 1 | 3 | — | 4 | 2 | 1 |

TABLE 82-continued

| Post-emergence Test | | | | | | | | |
|---|---|---|---|---|---|---|---|---|
| Cpd No. | SOLNI | AMARE | IPOHE | ECHCG | LOLPE | SETFA | ZEAMX | ABUTH |
| P17 | — | 2 | 0 | 3 | — | 3 | 1 | 1 |
| P18 | — | 0 | 1 | 1 | — | 1 | 1 | 1 |
| P19 | — | 2 | 2 | 3 | — | 4 | 2 | 1 |
| P20 | — | 1 | 1 | 1 | — | 3 | 1 | 0 |
| P21 | — | 1 | 0 | 0 | — | 2 | 1 | 1 |
| P22 | — | 4 | 1 | 0 | — | 2 | 2 | 1 |
| P23 | — | 0 | 0 | 0 | — | 0 | 0 | 0 |
| P24 | — | 0 | 0 | 0 | — | 0 | 0 | 1 |
| P25 | — | 0 | 0 | 0 | — | 0 | 0 | 0 |
| P26 | — | 0 | 0 | 1 | — | 0 | 0 | 0 |
| P27 | — | 0 | 0 | 0 | — | 0 | 0 | 0 |
| P28 | — | 0 | 0 | 0 | — | 0 | 0 | 0 |
| P29 | — | 0 | 0 | 4 | — | 3 | 2 | 1 |
| P30 | — | 1 | 2 | 4 | — | 4 | 3 | 3 |
| P31 | — | 0 | 0 | 0 | — | 0 | 0 | 0 |
| P32 | — | 1 | 1 | 3 | — | 3 | 1 | 1 |
| P33 | — | 0 | 0 | 0 | — | 0 | 0 | 0 |
| P34 | — | 0 | 0 | 0 | — | 0 | 0 | 0 |
| P35 | — | 0 | 0 | 4 | — | 4 | 3 | 0 |
| P36 | — | 0 | 0 | 0 | — | 1 | 0 | 0 |
| P37 | — | 1 | 1 | 2 | — | 2 | 1 | 0 |
| P38 | — | 3 | 3 | 5 | — | 4 | 2 | 1 |
| P39 | — | 0 | 0 | 3 | — | 3 | 0 | |
| P40 | — | 1 | 0 | 3 | — | 5 | 1 | |
| P41 | — | 0 | 1 | | — | 2 | 0 | 1 |
| P42 | — | 0 | 0 | | — | 0 | 0 | 0 |

The invention claimed is:

1. A compound of Formula (I):

(I)

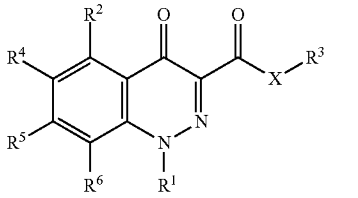

wherein

X is O, $NR^{13}$ or S;

$R^1$ is phenyl optionally substituted with 1, 2, 3, or 4 groups, which may be the same or different, represented by $R^7$;

$R^2$ is $C_1$-$C_6$alkylcarbonyl, $C_2$-$C_6$alkenyl, $C_2$-$C_6$alkynyl, $C_1$-$C_6$alkoxy$C_2$-$C_6$alkenyl, $C_2$-$C_6$alkenyloxy$C_1$-$C_6$alkyl, —$CR^{11}$—N—$OR^{10}$, phenyl, phenoxy, heteroaryl, wherein the heteroaryl moiety is a 5- or 6-membered aromatic monocyclic ring comprising 1, 2, or 3 heteroatoms individually selected from N, O and S, heterocyclyl, or heterocyclyloxy, wherein the heterocyclyl moieties are a 4-, 5- or 6-membered non-aromatic monocyclic ring comprising 1 or 2 heteroatoms individually selected from N, O and S, wherein the phenyl, phenoxy, heteroaryl, heterocyclyl, and heterocyclyloxy moieties are each independently and optionally substituted with 1, 2 or 3 groups, which may be the same or different, represented by $R^8$;

$R^3$ is hydrogen, $C_1$-$C_6$alkyl, $C_1$-$C_6$haloalkyl, $C_3$-$C_6$cycloalkyl, $C_3$-$C_6$cycloalkyl$C_1$-$C_6$alkyl, $C_1$-$C_6$alkoxy$C_1$-$C_6$alkyl, $C_2$-$C_6$alkenyl, $C_2$-$C_6$alkynyl, phenyl, or phenyl$C_1$-$C_3$alkyl, wherein the phenyl moieties are each independently and optionally substituted with 1, 2, 3 or 4 groups, which may be the same or different, represented by $R^{12}$;

$R^4$, $R^5$, and $R^6$ are each independently selected from hydrogen, halogen, cyano, $C_1$-$C_6$alkyl, $C_1$-$C_6$alkoxy, $C_1$-$C_6$haloalkyl, $C_1$-$C_6$haloalkoxy, $C_1$-$C_6$alkylsulfanyl, $C_1$-$C_6$alkylsulfinyl, and $C_1$-$C_6$alkylsulfonyl;

$R^7$ is chloro, cyano, methyl, methoxy, trifluoroalkyl, trifluoromethoxy, methylsulfanyl, or any two adjacent $R^7$ groups together with the carbon atoms to which they are attached form a quinolyl, indazolyl, 1,3-benzoxadiozolyl, or 1,4-benzodioxinyl group, and wherein the quinolyl, indazolyl, 1,3-benzoxadiozolyl, or 1,4-benzodioxinyl groups are each independently and optionally substituted with 1 2, 3 or 4 groups, which may be the same or different, represented by $R^9$;

$R^8$ and $R^9$ are each independently selected from halogen, $C_1$-$C_3$alkyl, $C_1$-$C_3$haloalkyl, and $C_1$-$C_3$alkoxy;

$R^{10}$ and $R^{11}$ are each independently selected from hydrogen and $C_1$-$C_3$alkyl;

$R^{12}$ is halogen, cyano, $C_1$-$C_3$alkyl, or $C_1$-$C_3$alkoxy;

$R^{13}$ is hydrogen, $C_1$-$C_3$alkyl, or $C_1$-$C_3$alkoxy;

or a salt or an N-oxide thereof.

2. The compound according to claim 1, wherein $R^2$ is $C_1$-$C_3$alkylcarbonyl, $C_1$-$C_3$alkoxy$C_2$-$C_3$alkenyl, —$CR^{11}$═N—$OR^{10}$, phenyl, phenoxy, heteroaryl, wherein the heteroaryl moiety is a 5-membered aromatic monocyclic ring comprising 1 or 2 heteroatoms individually selected from N and O, or heterocyclyl, wherein the heterocyclyl moiety is a 5- or 6-membered non-aromatic monocyclic ring comprising 1 or 2 heteroatoms individually selected from N and O, and wherein the phenyl, phenoxy, heteroaryl, and heterocyclyl moieties are each independently and optionally substituted with 1 or 2 groups, which may be the same or different, represented by $R^8$.

3. The compound according to claim 1, wherein $R^2$ is acetyl, 1-methoxyvinyl, 1-ethoxyvinyl, N-methoxy-C-methylcarbonimidoyl, 4-fluorophenyl, 4-fluorophenoxy, or oxazol-2-yl.

4. The compound according to claim 1, wherein $R^1$ is phenyl optionally substituted with 1 or 2 groups, which may be the same or different, represented by $R^7$.

5. The compound according to claim 1, wherein $R^3$ is hydrogen or $C_1$-$C_3$alkyl.

6. The compound according to claim 1, wherein $R^4$, $R^5$, and $R^6$ are all hydrogen.

7. The compound according to claim 1, wherein each $R^8$ is selected from halogen and $C_1$-$C_3$haloalkyl.

8. The compound according to claim 1, wherein each $R^9$ is selected from fluoro and methyl.

9. The compound according to claim 1, wherein $R^7$ is trifluoromethoxy.

10. The compound according to claim 1, wherein X is O.

11. A herbicidal composition comprising the compound according to claim 1 and an agriculturally acceptable formulation adjuvant.

12. The herbicidal composition according to claim 11, further comprising at least one additional pesticide.

13. The herbicidal composition according to claim 12, wherein the at least one additional pesticide is a herbicide or herbicide safener.

14. A method of controlling unwanted plant growth, comprising applying a compound of Formula (I) as defined in claim 1, or a herbicidal composition thereof, to the unwanted plants or to the locus thereof.

15. A compound selected from P1-P6, P9-P35, P39-P40, P51, and P54-P55

P1

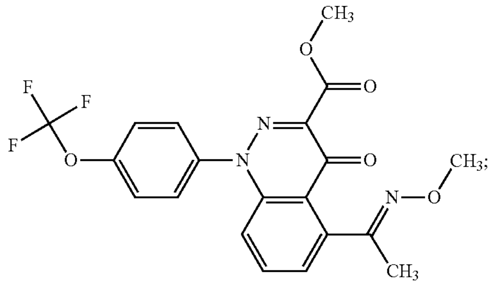

P2

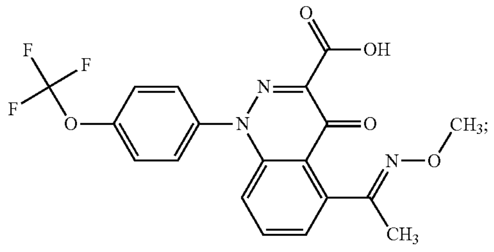

P3

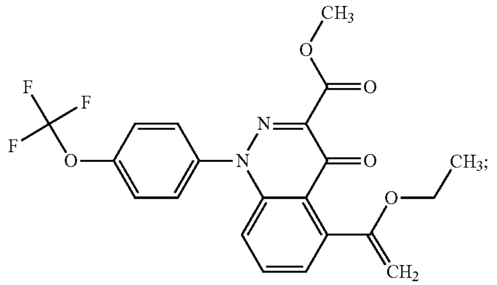

-continued

P4

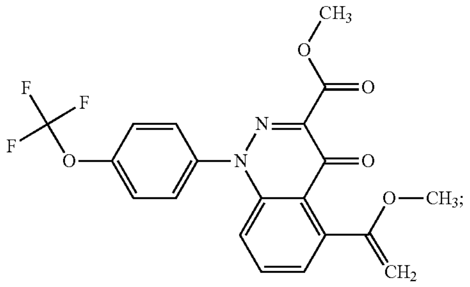

P5

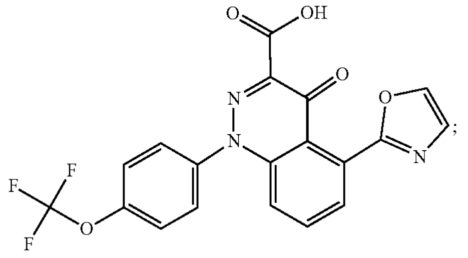

P6

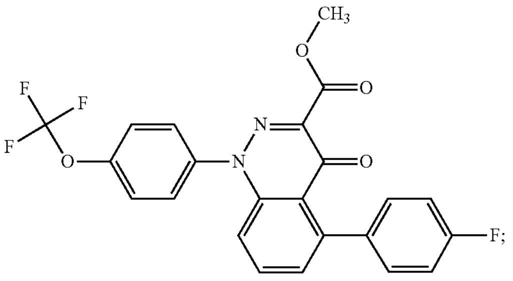

P9

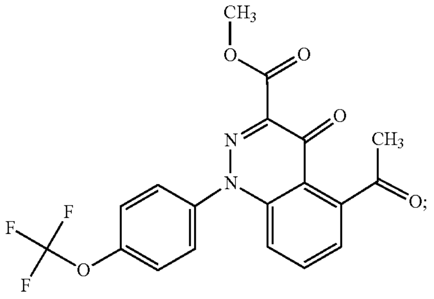

P10

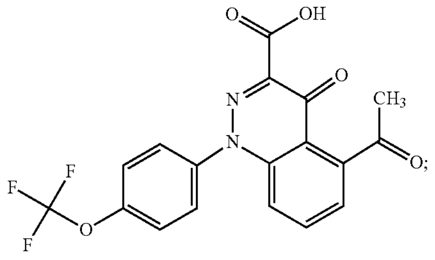

P11

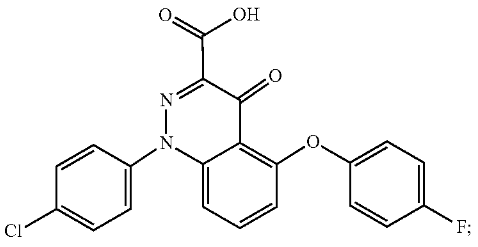

-continued
P12
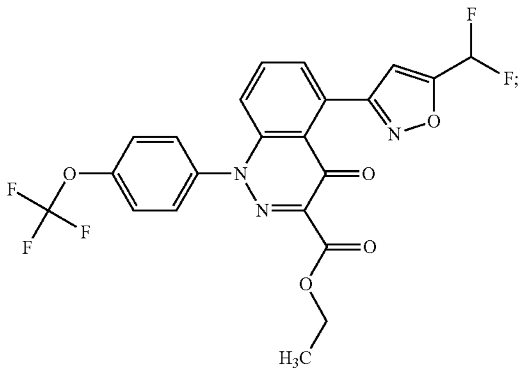
P13
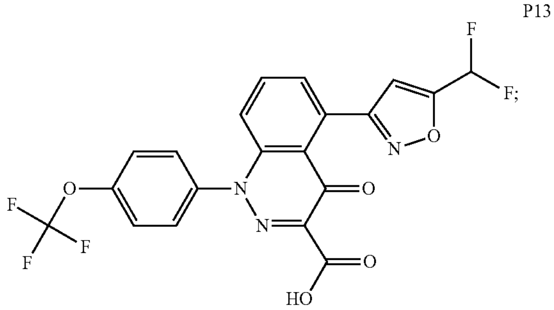
P14
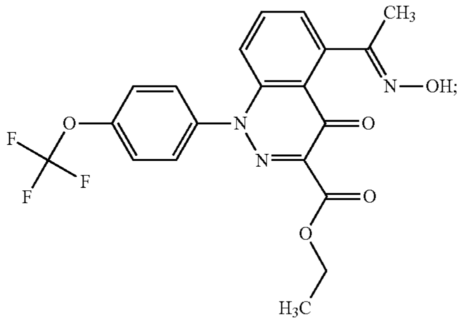
P15
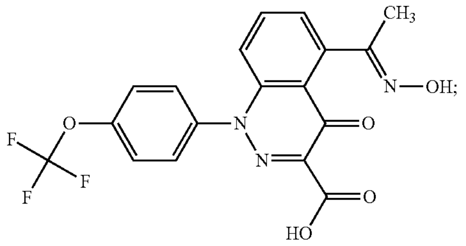
P16
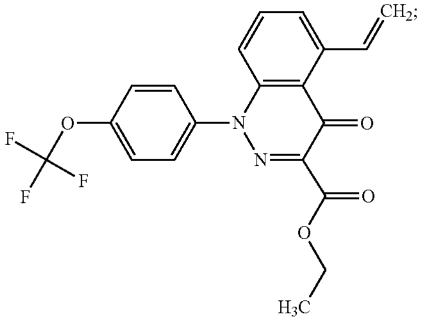
-continued
P17
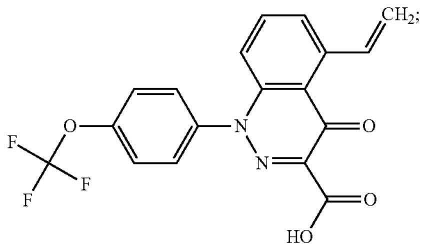
P18
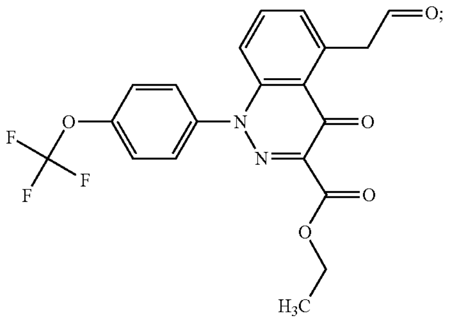
P19
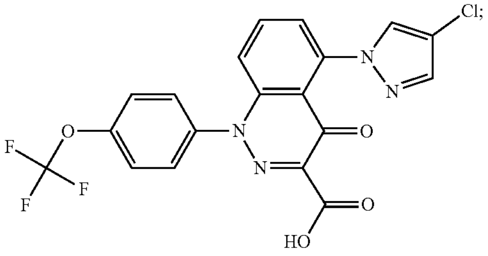
P20
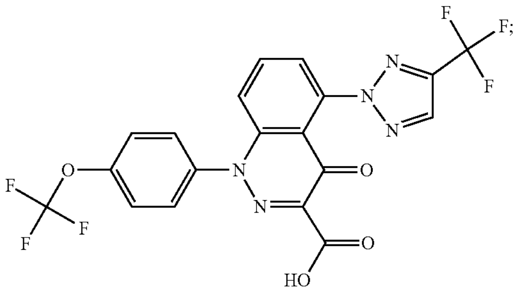
P21
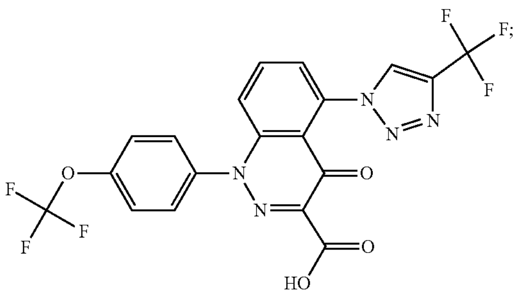

-continued
P22
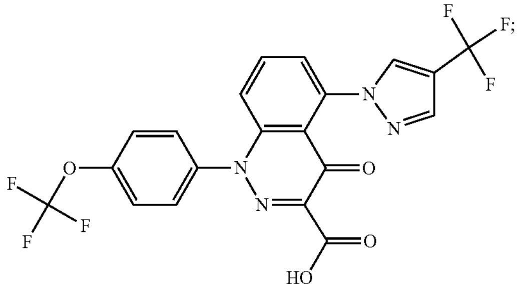
P23
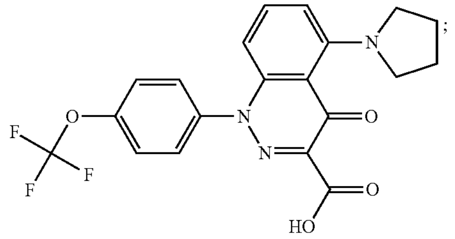
P24
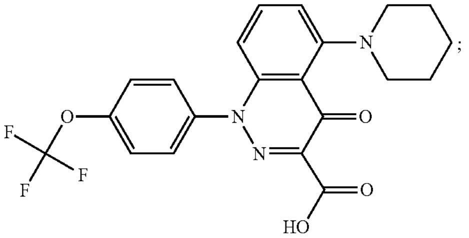
P25
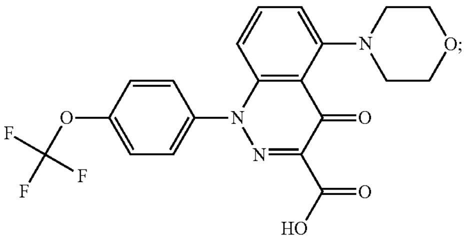
P26
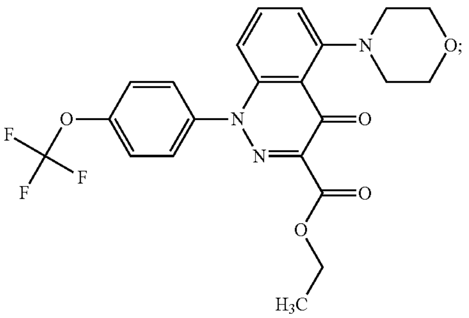
-continued
P27
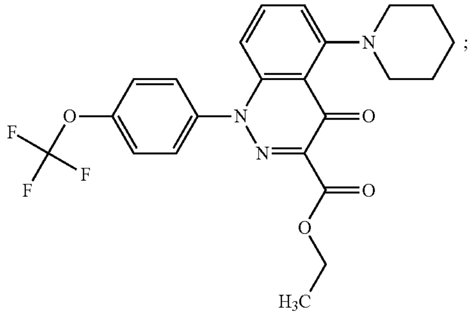
P28
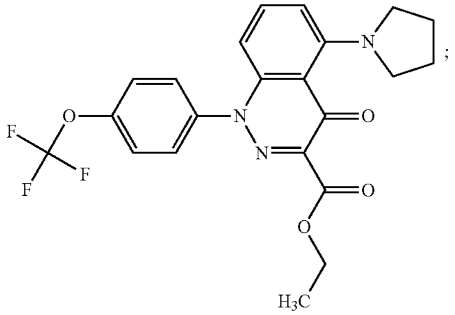
P29
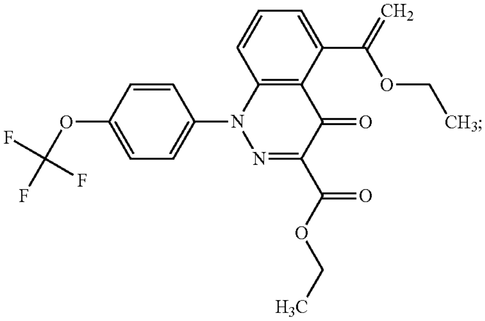
P30
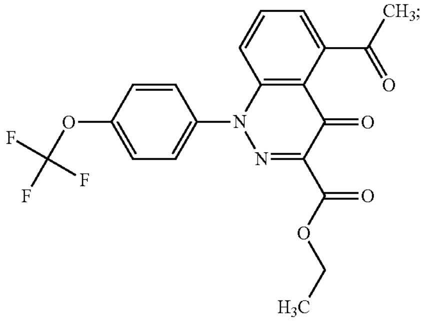

-continued
P31
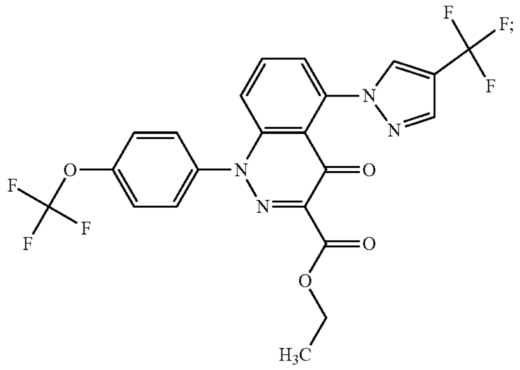
P32
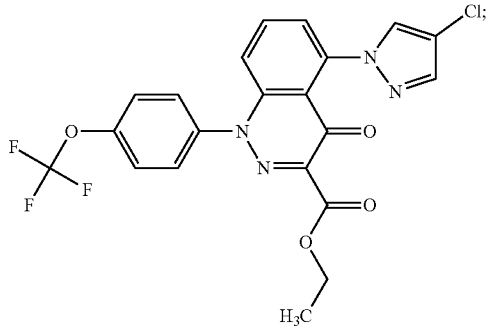
P33
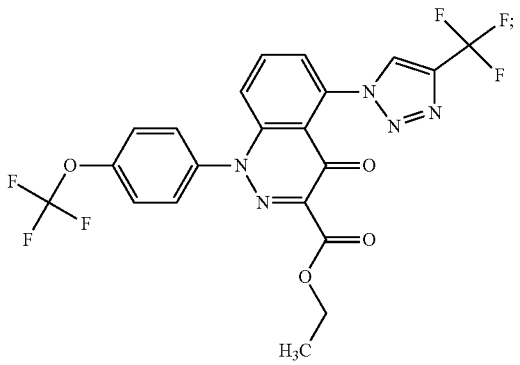
P34
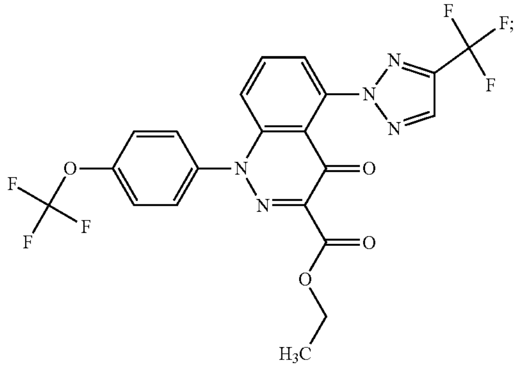
-continued
P35
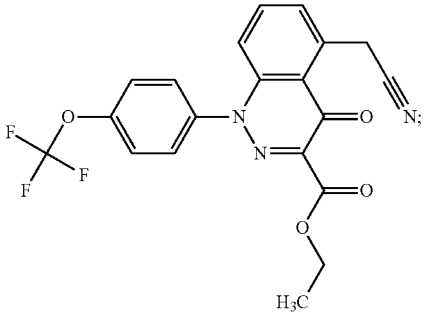
P39
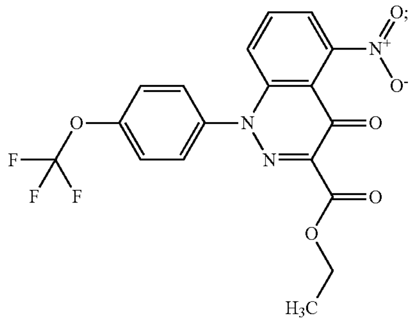
P40
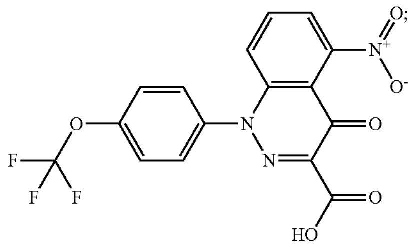
P51
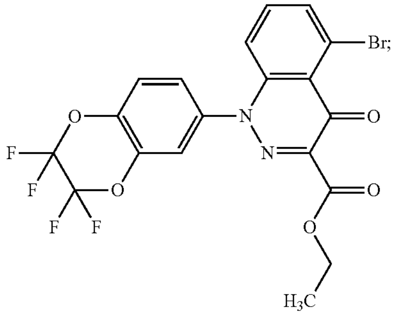
P54
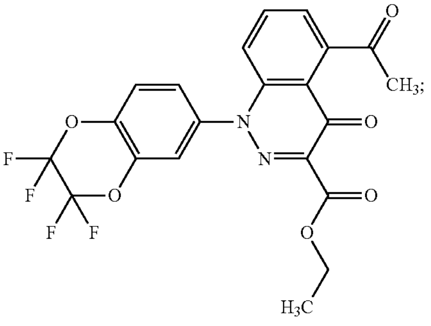
and -continued
P55
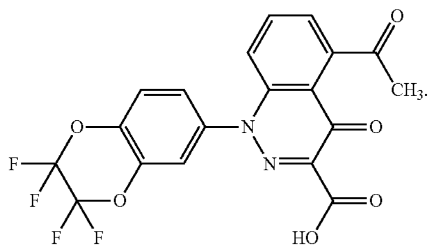
16. The compound of claim 15, wherein the compound is selected from P1-P6 and P9-P12.
17. The compound of claim 15, wherein the compound is selected from P39-P40.
18. The compound of claim 15, wherein the compound is selected from P51 and P54-P55.
19. A compound selected from P13-P24 or P25-P35:
P13
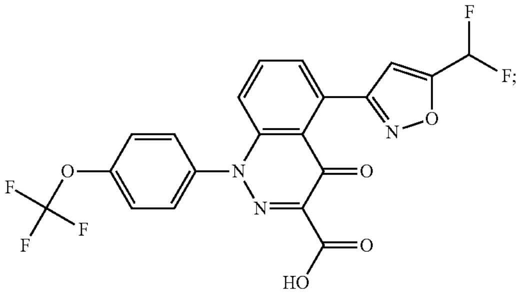
P14
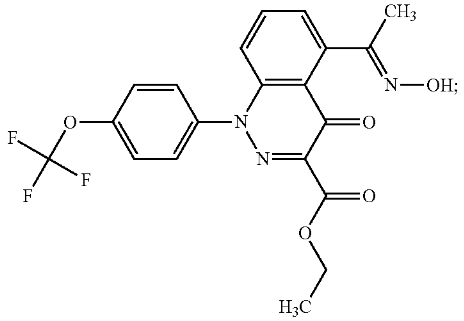
P15
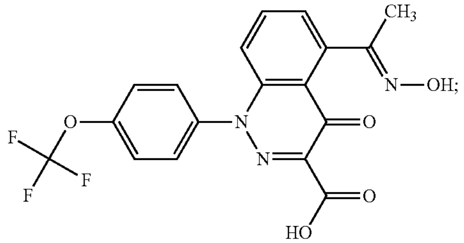
-continued
P16
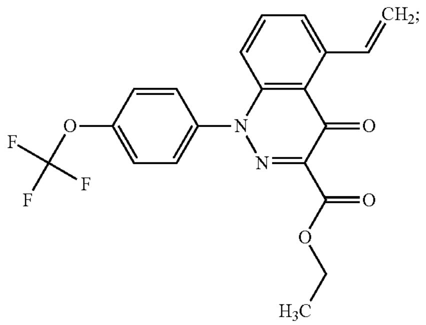
P17
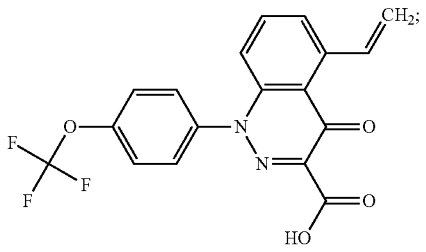
P18
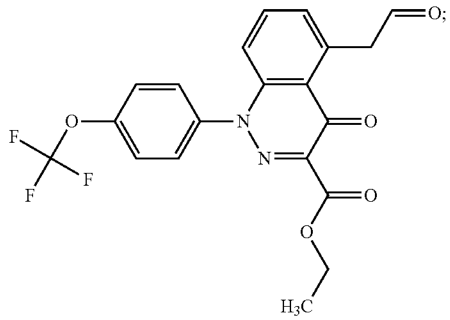
P19
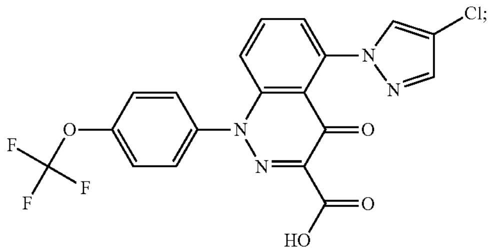
P20
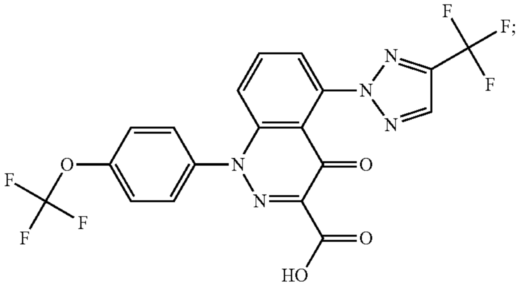

-continued
P21
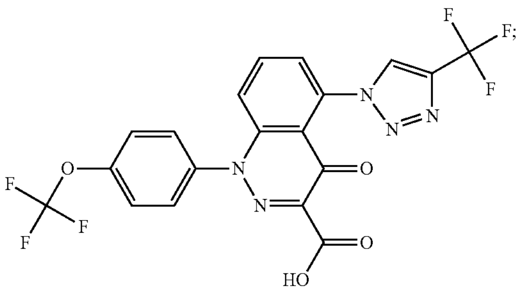
P22
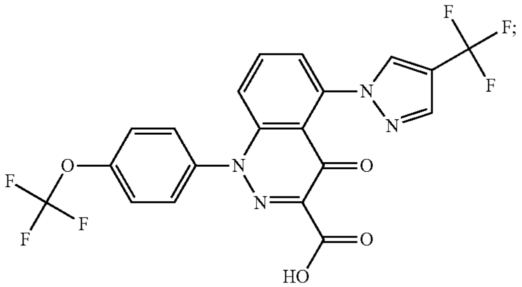
P23
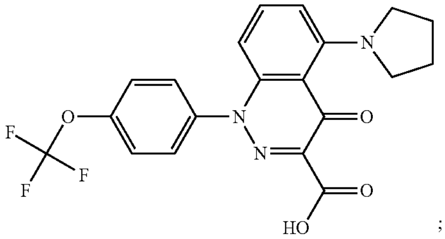
;
P24
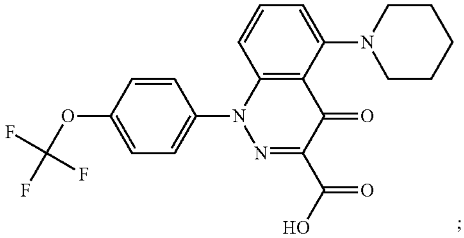
;
P25
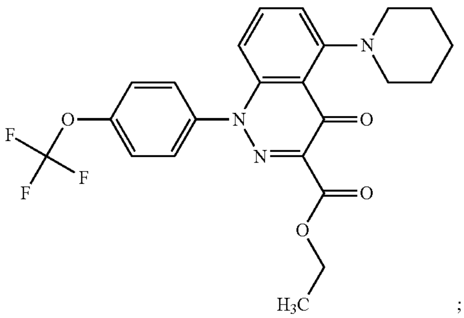
;
-continued
P26
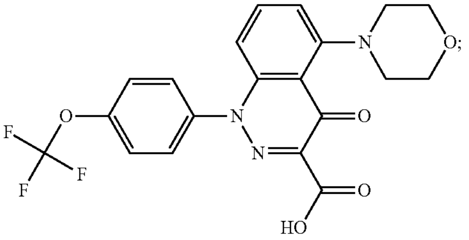
P27
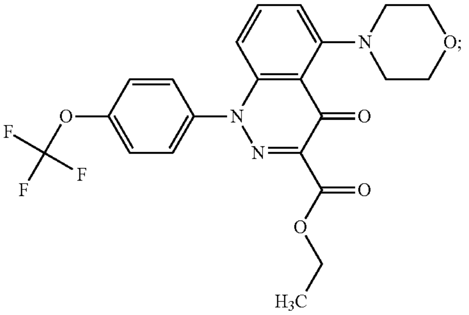
P28
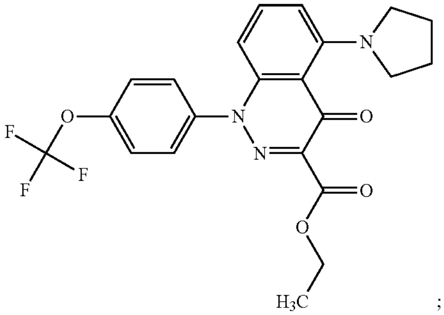
;
P29
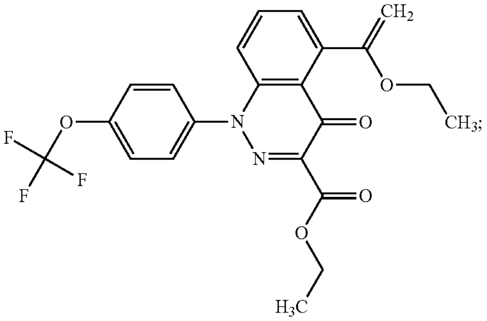

-continued
P30
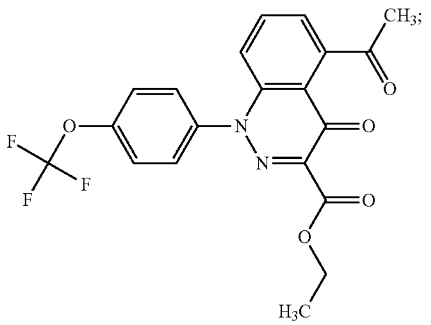
P31
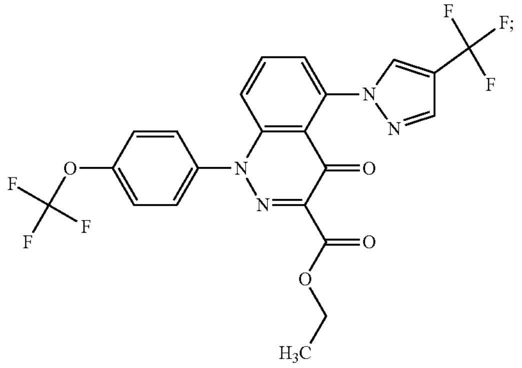
P32
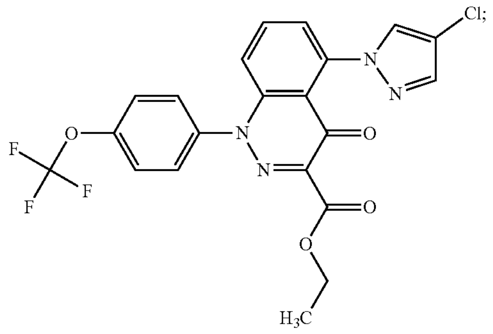
-continued
P33
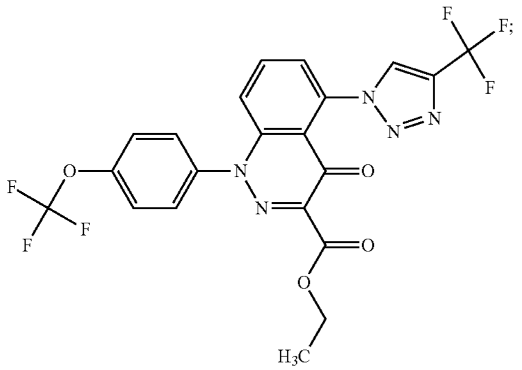
P34
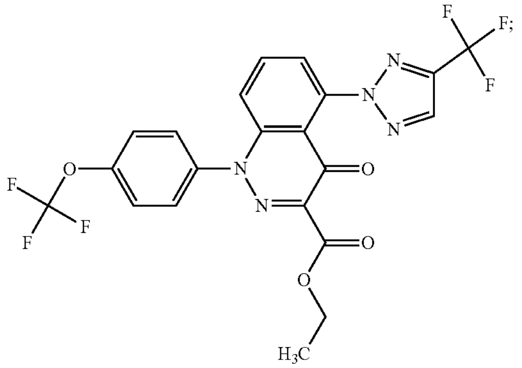
P35
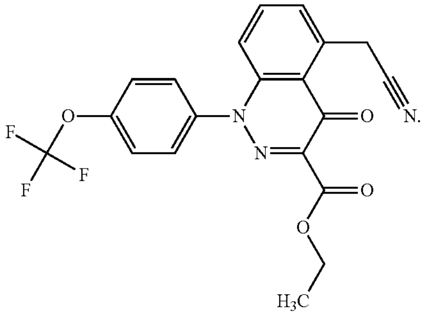
20. The compound of claim 19, wherein the compound is selected from P25-P35.
* * * * *